US011357839B2

(12) United States Patent
Schlom et al.

(10) Patent No.: US 11,357,839 B2
(45) Date of Patent: Jun. 14, 2022

(54) BRACHYURY PROTEIN, NON-POXVIRUS NON-YEAST VECTORS ENCODING BRACHYURY PROTEIN, AND THEIR USE

(71) Applicant: The United States of America, as represented by the Secretary, Department of Health and Human Services, Bethesda, MD (US)

(72) Inventors: **Jeff

(56) References Cited

OTHER PUBLICATIONS

Edwards et al., "The human homolog T of the mouse T(Brachyury) gene; gene structure, cDNA sequence, and assignment to chromosome 6q27," *Genome Res.* 6(3), 226-233 (1996).
Fan et al., "TBX3 and its isoform TBX3+2a are functionally distinctive in inhibition of senescence and are overexpressed in a subset of breast cancer cell lines," *Cancer Res.*, 64 (15), 5132-5139 (2004).
Federal Register, Daily Journal of the United States Government, Public Telephone Conference Regarding Licensing and Collaborative Research Opportunities for TRICOM-A Synergistic Triad of Costimulatory Molecules Used in Cancer Vaccines for the Prevention and Treatment of Cancer, May 6, 2009.
Fernando et al., "The T-box transcription factor Brachyury promotes epithelial-mesenchymal transition in human tumor cells," *J. Clin. Invest.*, 120 (2), 533-544 (2010).
Genbank Accession No. AF012131 (printed Jan. 1, 1998).
Genbank Accession No. NP_003172 (printed Jun. 25, 2015.
Genbank Accession No. NM_003181 (printed Jun. 25, 2015).
Genbank Accession No. NM_009309 (printed Feb. 15, 2015).
Gokhale et al., "Brachyury is expressed by human teratocarcinoma cells in the absence of mesodermal differentiation," *Cell Growth Differ.*, 11 (3), 157-162 (2000).
Hamilton et al., "Cancer vaccines targeting the epithelial-mesenchymal transition: tissue distribution of brachyury and other drivers of the mesenchymal-like phenotype of carcinomas," *Semin. Oncol.*, 39 (3), 358-366 (2012).
Herrmann et al., "Cloning of the T gene required in mesoderm formation in the mouse," *Nature*, 343 (6259), 617-622 (1990).
Huber et al., "Molecular requirements for epithelial-mesenchymal transition during tumor progression," *Curr. Opin. Cell Biol.*, 17 (5), 548-558 (2005).
International Preliminary Report on Patentability, Application No. PCT/US2013/059737, dated Mar. 17, 2015.
International Search Report, Application No. PCT/US2013/059737, dated Nov. 25, 2013.
Kispert et al., "The Brachyury gene encodes a novel DNA binding protein," *Embo J.*, 12 (8), 3211-3220 (1993).
Kovesdi et al., "Adenoviral producer cells," *Viruses*, 2 (8), 1681-1703 (2010).
Krukovskaia et al., "Investigation of transcription factor Brachyury (T) expression in human normal and tumor tissues," *Vopr. Onkol.*, 54 (6), 739-743 (2008) (article in Russian).
Mahlamäki et al., "Frequent amplification of 8q24, 11 q, 17q, and 20q-specific genes in pancreatic cancer," *Genes Chromosomes Cancer*, 35 (4), 353-358 (2002).
Naruse et al., "A novel gene trapping for identifying genes expressed under the control of specific transcription factors," *Biochem. Biophys. Res. Commun.*, 361 (1), 109-115 (2007).
Nishiwaki et al., "The overexpression of TBX1 gene in endometrioid carcinoma cells," *Proc. Amer. Assoc. Cancer Res.*, 47, AACR meting abstracts online (2006).
Palena et al., "The human T-box mesodermal transcription factor Brachyury is a candidate target for T-cell-mediated cancer immunotherapy," *Clin. Cancer Res.*, 13 (8), 2471-2478 (2007).
Palena et al., "Vaccines against human carcinomas: strategies to improve antitumor immune responses," *J. Biomed. Biotech.*, Article ID 380697, 12 pages (2010).
Papaioannou et al., "The T-box gene family," *Bioessays*, 20 (1), 9-19 (1998).
Paterson et al.," Listeria and *Salmonella* bacterial vectors of tumor-associated antigens for cancer immunotherapy," *Seminars in Immunology*, 22 (3), 183-189 (2010).
Pisarev et al., "Full-length dominant-negative survivin for cancer immunotherapy," *Clin. Cancer Rev.*, 9 (17), 6523-6533 (2003).
Presneau et al., "Potential therapeutic targets for chordoma: PI3K/AKT/TSC1/TSC2/mTOR pathway," *Br. J. Cancer*, 100 (9), 1406-1414 (2009).
Ruppert et al., "Prominent role of secondary anchor residues in peptide binding to HLA-A2.1 molecules," *Cell*, 74 (5), 929-937 (1993).
Scheibenbogen et al., "Rational peptide-based tumour vaccine development and T cell monitoring," *Semin. Cancer Biol.*, 13 (6), 423-429 (2003).
Schlom, "Therapeutic Cancer Vaccines: Current Status and Moving Forward," *J. Natl. Cancer.*, 104 (8), 599-613 (2012).
Sinclair et al., "TBX2 is preferentially amplified in BRCA1- and BRCA2-related breast tumors," *Cancer Res.*, 62 (13), 3587-3599 (2002).
Smith et al., "Expression of a Xenopus homolog of Brachyury (T) is an immediate-early response to mesoderm induction," *Cell*, 67 (1), 79-87 (1991).
Tatsis et al., "Adenoviruses as vaccine vectors," *Mol. Ther.*, 10 (4), 616-629 (2004).
Thiery, "Epithelial-mesenchymal transitions in tumour progression," *Nat. Rev. Cancer*, 2 (6), 442-454 (2002).
Tirabosco et al., "Brachyury expression in extra-axial skeletal and soft tissue chordomas: a marker that distinguishes chordoma from mixed tumor/myoepithelioma/parachordoma in soft tissue," *Am. J. Surg. Path.*, 32 (4), 572-580 (2008) (abstract only).
Vidricaire et al., "Expression of the Brachyury gene during mesoderm development in differentiating embryonal carcinoma cell cultures," *Development*, 120 (1), 115-122 (1994).
Vujovic et al., "Brachyury, a crucial regulator of notochordal development, is a novel biomarker for chordomas," *J. Pathol.*, 209 (2), 157-165 (2006).
Wansley et al., "Vaccination with a recombinant *Saccharomyces cerevisiae* expressing a tumor antigen breaks immune tolerance and elicits therapeutic antitumor responses," *Clin. Cancer Res.*, 14 (13), 4316-4325 (2008).
Wen et al., "Chitosan nanoparticles act as an adjuvant to promote both Th1 and Th2 immune responses induced by ovalbumin in mice," *Marine Drugs*, 9 (6), 1038-1055 (2011).
Written Opinion of the International Searching Authority, Application No. PCT/US2013/059737, dated Nov. 25, 2013.
Yang et al., "Twist, a master regulator of morphogenesis, plays an essential role in tumor metastasis," *Cell*, 117 (7), 927-939 (2004).
Zaharoff et al., "Intratumoral immunotherapy of established solid tumors with chitosan/IL-12," *J. Immunother.*, 33 (7), 697-705 (2010).
Zuniga et al., "Attenuated measles virus as a vaccine vector," *Vaccine*, 25 (16), 2974-2983 (2007).

\* cited by examiner

FIG. 2

| Peptide | IL-2 | IL-8 | IL12p70 | IL-1b | GM-CSF | IFNγ | IL-6 | IL-10 | TNFα |
|---|---|---|---|---|---|---|---|---|---|
| Brachyury class II B | 223 | 586 | 3.0 | 4.0 | 4720 | 306 | 11.0 | 4058 | 817 |
| Brachyury Class II A | 1.7 | 4.3 | 7.6 | 4.1 | 13 | 55.6 | 2.7 | 21.7 | 14.4 |

CD4 T cell line is T-/BRA specific to epitope QWGWLLPGTSTLCPP (Brachyury class II B).

Brachyury class II A = RPMFPVLKVNVSGLD; Brachyury class II B = QWGWLLPGTSTLCPP.

FIG. 7A
| IgG titer | Normal donors | Breast cancer patients | p value |
|---|---|---|---|
| ≤1:100 (negative) | 17/20 | 6/19 | 0.0004 |
| 1:100-1:400 | 2/20 | 5/19 | 0.1940 |
| ≥ 1:400 | 1/20 | 8/19 | 0.0050 |
FIG. 7B
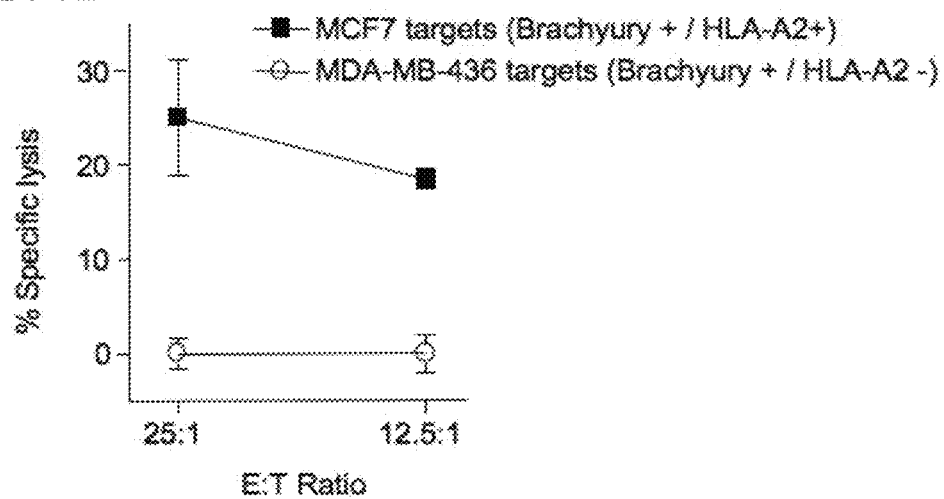
FIG. 7C
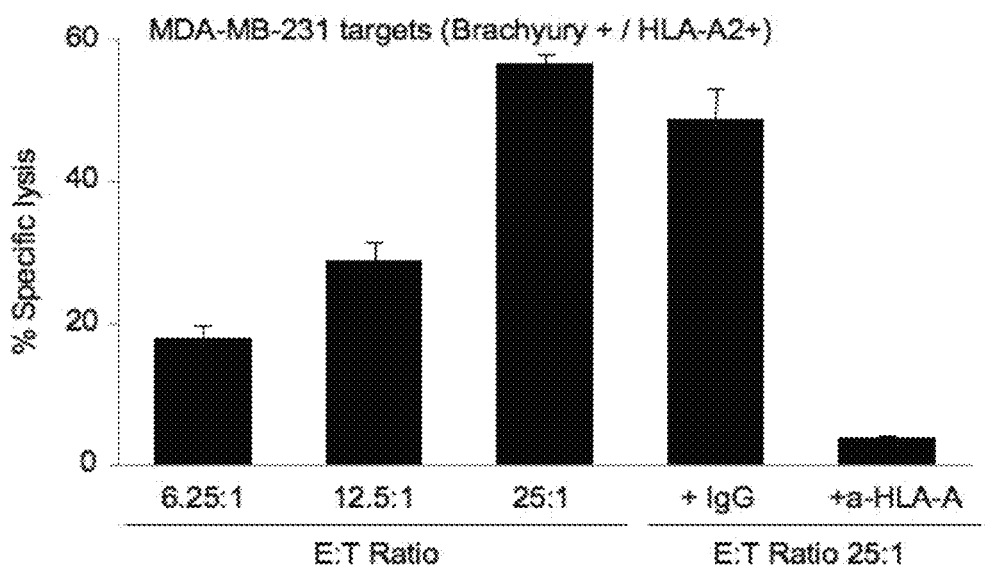

BRACHYURY PROTEIN, NON-POXVIRUS NON-YEAST VECTORS ENCODING BRACHYURY PROTEIN, AND THEIR USE

CROSS-REFERENCE TO RELATED APPLICATIONS

This patent application is a divisional application of U.S. patent application Ser. No. 14/428,308, filed Mar. 13, 2015, now abandoned, which claims the benefit of U.S. national phase of International Patent Application No. PCT/US2013/059737, filed Sep. 13, 2013, which claims the benefit of U.S. Provisional Patent Application No. 61/701,525, filed Sep. 14, 2012, each of which is incorporated by reference in its entirety herein.

SEQUENCE LISTING

Incorporated by reference in its entirety herein is a nucleotide/amino acid sequence listing submitted concurrently herewith and identified as follows: One 14,638 Byte ASCII (Text) file named "740352_ST25.TXT," created on Aug. 21, 2018.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is an amino acid sequence of a human Brachyury protein.

SEQ ID NO: 2 is a nucleic acid sequence encoding a human Brachyury protein.

SEQ ID NO: 3 is an amino acid sequence of a murine Brachyury protein.

SEQ ID NO: 4 is a nucleic acid sequence encoding a murine Brachyury protein.

SEQ ID NO: 5 is a Brachyury class IIA epitope.

SEQ ID NO: 6 is a Brachyury class IIB epitope.

FIELD

This application relates to the field of cancer therapeutics, specifically to the use of a Brachyury protein and non-poxvirus, non-yeast vectors encoding a Brachyury protein for the treatment of cancer.

BACKGROUND

The Brachyury gene was initially cloned from mouse developmental mutants characterized by an arrest in mesoderm formation (Hermann et al, *Nature* 1990; 343:617-22) has been recognized as gene that is important in mesoderm development during gastrulation. Brachyury is a member of a family of transcription factors, designated T-box transcription factors, these factors are characterized by a conserved DNA-binding domain (Papaioannou et al., *Bioessays* 1998; 20:9-19). These transcription factors play an essential role in the formation and organization of mesoderm in vertebrates (see, for example, Edwards et al., *Genome Res* 1996; 6:226-33). In addition to the important role of the T-box proteins in the control of developmental processes, several members of this family are deregulated in cancer. For example, the human Tbx2 gene has been reported to be amplified in pancreatic cancer cell lines (Mahlamaki et al., *Genes Chromosomes Cancer* 2002, 35:353-8) and is overexpressed in BRCA-1- and BRCA-2-mutated breast tumors (Sinclair et al., *Cancer Res* 2002; 62:3587-91). In addition, Tbx3 expression has been shown to be augmented in certain human breast cancer cell lines (Fan et al., *Cancer Res* 2004; 64:5132-9). Expression of Brachyury has also been documented in human teratocarcinoma lines: a subset of germ cell tumors, teratocarcinomas are embryonal carcinoma cells with competence for mesoderm differentiation (Gokhale et al., *Cell Growth Differ* 2000; 11:157-62) and in chordomas (see, for example, Vojovic et al., *J Pathol* 2006; 209:157-65).

Immunotherapeutic interventions against cancer depend on the identification of tumor antigens able to elicit a host immune response against the tumor cells. Good targets are molecules that are selectively expressed by malignant cells and that are also essential for malignant transformation and/or tumor progression. The epithelial-mesenchymal transition (EMT) has been recognized as a key step during the progression of primary tumors into metastases (Thiery et al., *Nat Rev Cancer* 2002; 2:442-54). Several molecules have been identified that play a key role in EMT during tumor progression (Huber et al., *Curr Opin Cell Biol* 2005; 17:548-58), among them the transcription factors Twist, Snail, and Slug (Yang et al., *Cell* 2004; 117:927-39; Cano et al., *Nat Cell Biol* 2000; 2: 76-83). Molecules that trigger EMT could function to prevent tumor invasion and metastasis. However, a need remains for reagents that induce an effective immune response to cancer, including a CD4 and a CD8 T cell response.

SUMMARY

It is disclosed herein that Brachyury protein or a Brachyury polypeptide can be used to induce Brachyury-specific CD4+ T cells in vivo and ex vivo. It is also disclosed that Brachyury protein and Brachyury polypeptides can be used to stimulate the production of both Brachyury-specific CD4+ T cells and Brachyury-specific CD8+ T cells. Brachyury is expressed in numerous human cancers, such as in cancer of the small intestine, stomach, kidney bladder, uterus, ovary, testes, lung, colon, prostate, bronchial tube, chronic lymphocytic leukemia (CLL), other B cell-based malignancies, and breast cancer, such as infiltrating ductal carcinomas of the breast. Thus, Brachyury protein, Brachyury polypeptides, and nucleic acids encoding Brachyury protein and/or polypeptides, can be used to produce Brachyury specific CD4+ T cells, and CD8+ T cells, that can be used for the treatment or prevention of cancer.

In some embodiments, methods are disclosed for inducing CD4+ Brachyury-specific T cells and/or CD8+ Brachyury specific T cells. The methods include the use of a Brachyury protein, a Brachyury polypeptide, nucleic acids encoding the Brachyury protein and/or Brachyury polypeptides, or host cells expressing the Brachyury protein or polypeptide, such as such as a *Salmonella* or *Listeria* host cells. These agents can be administered either alone or in conjunction with another agent, such as a cytokine and/or another cancer therapy. In some embodiments, methods are disclosed for treating a subject with a cancer, such as a breast cancer, cancer of the small intestine, stomach, kidney, bladder, uterus, ovaries, testes lung, colon or prostate, or a tumor of B cell origin, or for preventing these cancers in a subject. In some embodiments, the methods include measuring Brachyury-specific CD4+ T cells. In further embodiments, the methods also induce CD8+ Brachyury specific T cells.

Non-pox non-yeast vectors encoding a Brachyury protein are disclosed that can be used to induce CD4+ Brachyury-specific T cells and/or CD8+ Brachyury-specific T cells. In some non-limiting examples, the vector is an alphavirus, a lentivirus, an adenovirus, a measles virus or a poliovirus vector. In additional embodiments, host cells transformed with these vectors, such as *Salmonella* and *Listeria* host cells are provided.

In additional embodiments, methods are provided for inhibiting the growth of a cancer cell in a subject. These methods include contacting a dendritic cell with a protein comprising an amino acid sequence at least 90% identical to the amino acid sequence set forth as SEQ ID NO: 1, a polypeptide comprising at least 15 consecutive amino acids of the amino acid sequence set forth at SEQ ID NO: 1 that specifically binds a Major Histocompatibility Class (MHC class II) molecule, or a *Listeria* or *Salmonella* host cell expressing the protein or the polypeptide thereby preparing a specific antigen presenting cell. These methods also include administering the antigen presenting cell to the subject, thereby inducing an immune response and inhibiting the growth of the cancer cell.

The foregoing and other features and advantages will become more apparent from the following detailed description of several embodiments, which proceeds with reference to the accompanying figures.

BRIEF DESCRIPTION OF THE DRAWINGS

FIG. 2. A Brachyury-specific CD4 T cell line releases cytokines and chemokines when stimulated with a class-II DRB1*0401 binding Brachyury peptide. Brachyury class IIA epitope (SEQ ID NO: 5) and Brachyury class IIB epitope (SEQ ID NO: 6).

FIG. 7A-7C. Immunogenicity of Brachyury. (A) Detection of IgG antibodies against Brachyury in the serum of normal donors and metastatic breast cancer patients. Shown is the number of positive cases in each group, stratified by titer of IgG as determined by ELISA assay. Statistical analysis was performed, comparing breast vs. normal donors. Brachyury-specific CTLs were generated from the peripheral blood of a prostate cancer patient via stimulation with a Brachyury-derived peptide. Cytotoxic activity was assessed in a 16-h assay against (B) HLA-A2$^+$/Brachyury$^+$ MCF7 cells or HLA-A2$^-$/Brachyury$^+$ MDA-MB-436 cells, and (C) HLA-A2$^+$/Brachyury$^+$ MDA-MB-231 cells. The effector-to-target (E:T) ratios are indicated; major histocompatibility complex (MHC)—restriction was analyzed by pre-incubation of the targets with control IgG or a HLA-A specific antibody.

DETAILED DESCRIPTION

Figure 1:
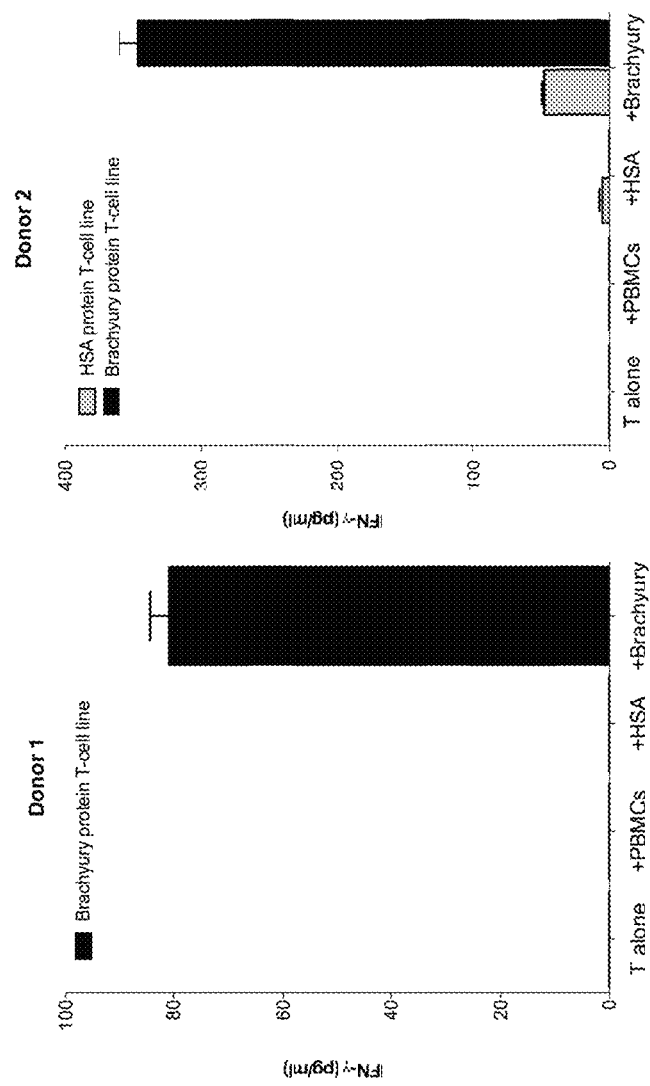
FIG. 1. Brachyury-specific CD4+ T cells can be expanded from PBMCs of normal donors by culture in the presence of purified recombinant Brachyury protein. Dendritic cells (DCs) from 2 normal donors were prepared by culture in the presence of GM-CSF and IL-4. On day 5, a purified recombinant Brachyury protein was added (10 g/ml) for 48 hours. For donor 2, an additional culture was set up using purified HSA (human serum albumin) control protein (10 µg/ml). On day 7, protein-pulsed DCs were harvested, irradiated (20 Gy) and used as antigen-presenting cells (APCs) to stimulate autologous PBMCs (ratio DC:PBMCs equal to 1:10). On days 3 and 5, IL-2 (20 U/ml) was added to the cultures. T cells were harvested on day 7 and CD4+ T cells were isolated by negative selection with magnetic beads. CD4+ T cells were stimulated in similar manner for an additional 7-day cycle. On day 7, CD4+ T cells were re-isolated by using magnetic beads and evaluated for IFN-gamma production in response to autologous, irradiated PBMCs (ratio PBMCs:T cells equal to 3:1) alone or pulsed with control HSA protein vs. Brachyury protein (10 µg/ml). Culture supernatants were collected at 96 hours and evaluated for IFN-gamma by ELISA.
Figure 3A:
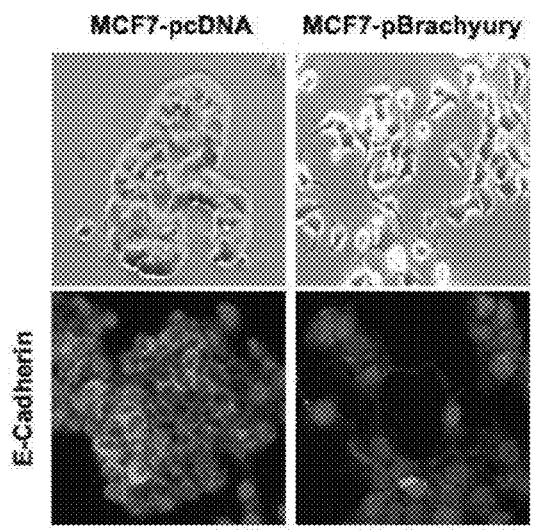
FIG. 3A-3E. Brachyury induces an epithelial-to-mesenchymal transition (EMT) in breast carcinoma cells. (A) MCF7-pcDNA and MCF7-phBrachyury stable transfectants grown on plastic surface for bright field images (top panels) and grown immunofluorescence analysis of E-cadherin expression (green signal); blue signal represents DAPI-stained nuclei (bottom panels). (B) Membrane images from in vitro cell migration (top panels) and ECM invasion assays (bottom panels) for MCF7-pcDNA and MCF7-pBrachyury cells. Results are representative of three experiments. (C, D) Real-time PCR was performed on indicated cell pairs for Brachyury, Fibronectin, and Vimentin. Values (mean±SEM) are expressed as a ratio to the endogenous control GAPDH. (E) Immunofluorescent analysis of Fibronectin expression in MDA-MB-436-con.shRNA and MDA-MB-436-Br.shRNA stable transfectants (original magnification 20×). The green signal represents staining for Fibronectin; the blue signal represents the DAPI-stained nuclei.
Figure 3B:
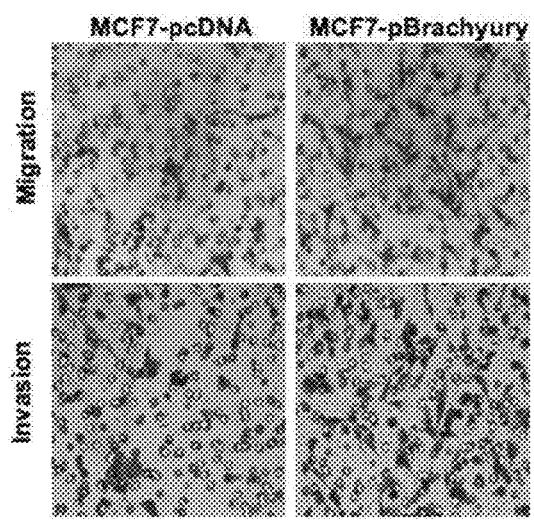
Figure 3C:
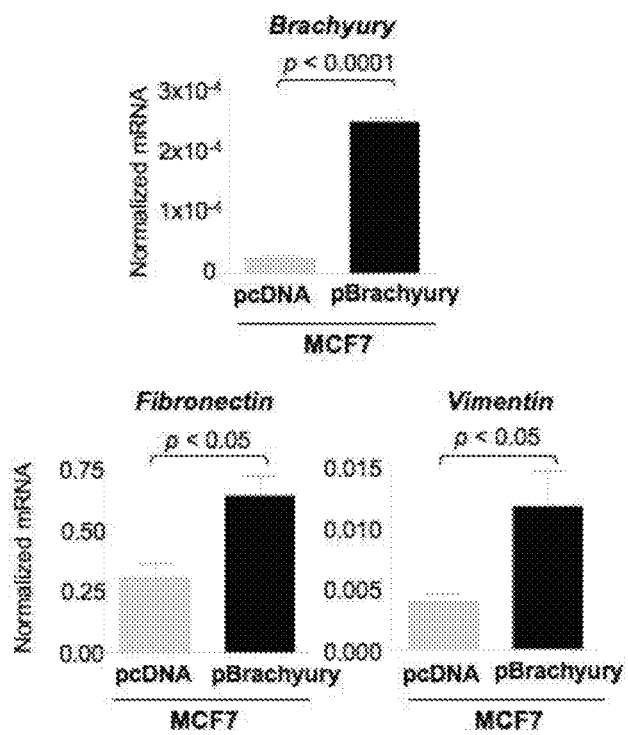
Figure 3D:
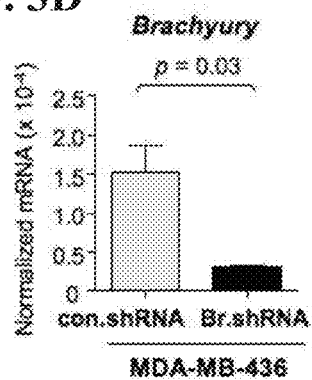
Figure 3E:
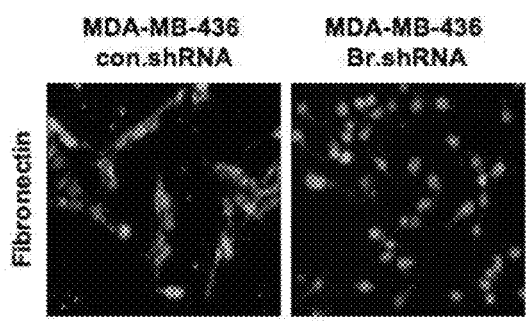
Figures 4A, 4C:
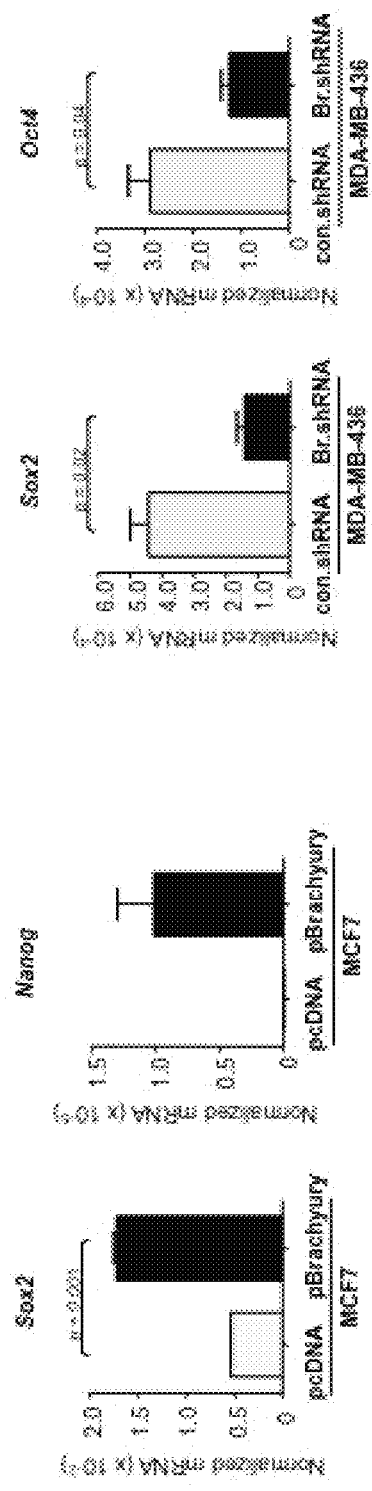
FIGS. 4A-4D. Effect of Brachyury expression on stem cell marker expression and mammosphere growth of tumor cells. Real-time PCR was performed for indicated genes on cDNA from (A) MCF7-pcDNA and MCF7-phBrachyury cells and (C) MDA-MB-436-con.shRNA and MDA-MB-436-Br.shRNA cells. Values (mean±SEM) are expressed as a ratio to the endogenous control GAPDH. Mammospheres were grown from the MCF7 (B) or the MDA-MB-436 (D) tumor cell pairs on ultra-low-attachment plates. Primary mammospheres were dissociated and re-plated for secondary cultures. Bright field images of mammospheres at 10× magnification and mean number of mammospheres per 10× microscope field are shown for secondary cultures in the left and right panels, respectively. Error bars indicate SEM of 8-10 measurements.
Figures 4B, 4D:
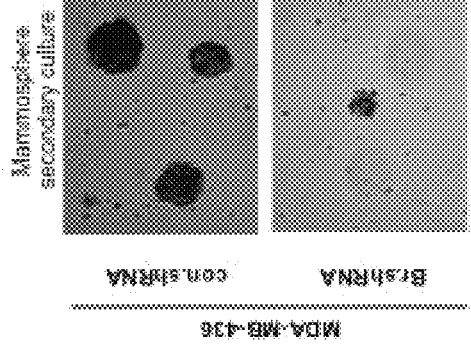
Figure 5A:
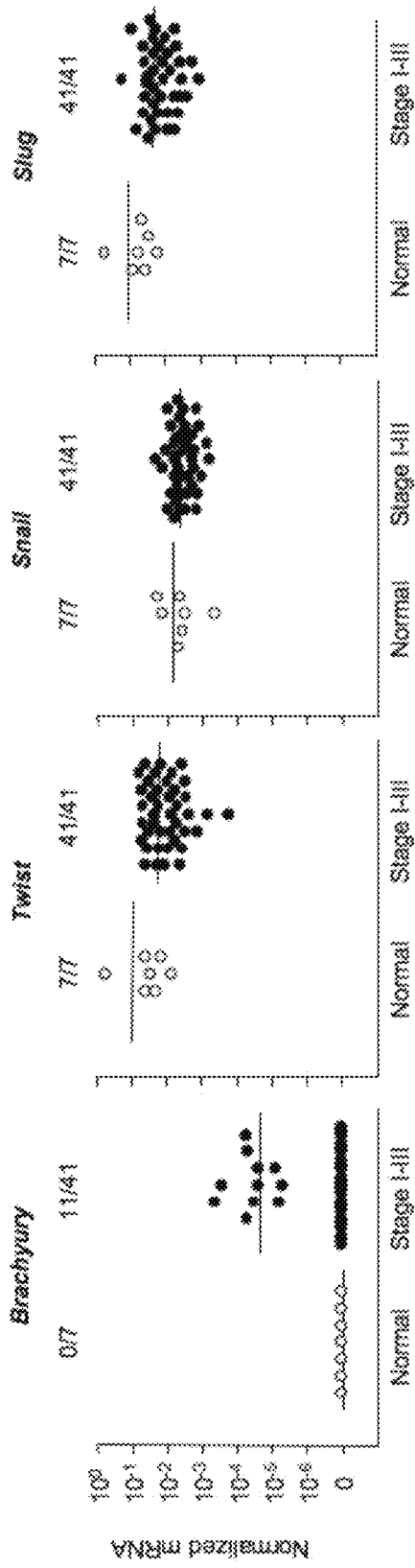
FIGS. 5A-5D. Expression of Brachyury mRNA in breast carcinoma tissues. (A) Real-time PCR was performed for Brachyury, Twist, Snail, and Slug on human breast primary tumor tissue cDNA from 41 breast cancer patients. As controls, 7 samples of normal breast cDNA were also analyzed, each obtained from a histologically normal section of breast from a patient with cancer or fibrocystic disease. (B) Real-time PCR was performed for Brachyury on human primary breast tumor tissue cDNA from 107 invasive ductal adenocarcinomas, 6 invasive lobular adenocarcinomas, and 5 mixed ductal/lobular adenocarcinomas. As controls, 7 samples of normal breast cDNA were also analyzed, each obtained from a histologically normal section of breast from a patient with cancer or fibrocystic disease. All values and the means for each group are expressed as a ratio to the endogenous control GAPDH. Brachyury expression is shown for (B) breast primary tumor tissues from stages I-III grouped together, (C) breast primary tumor tissues grouped by histological tumor grade (Nottingham grading), (D) breast primary tumor tissues grouped by ER and PR expression (ER+PR+ versus ER−PR−).
Figure 5B:
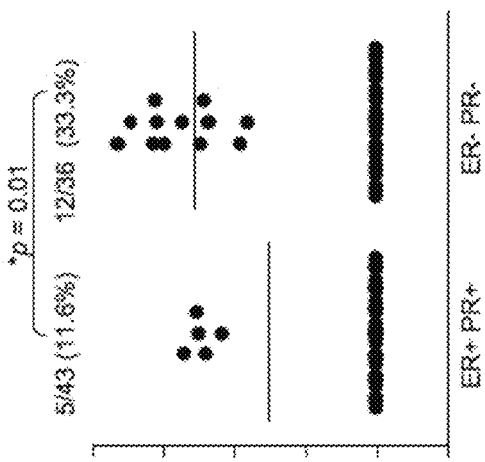
Figure 5C:
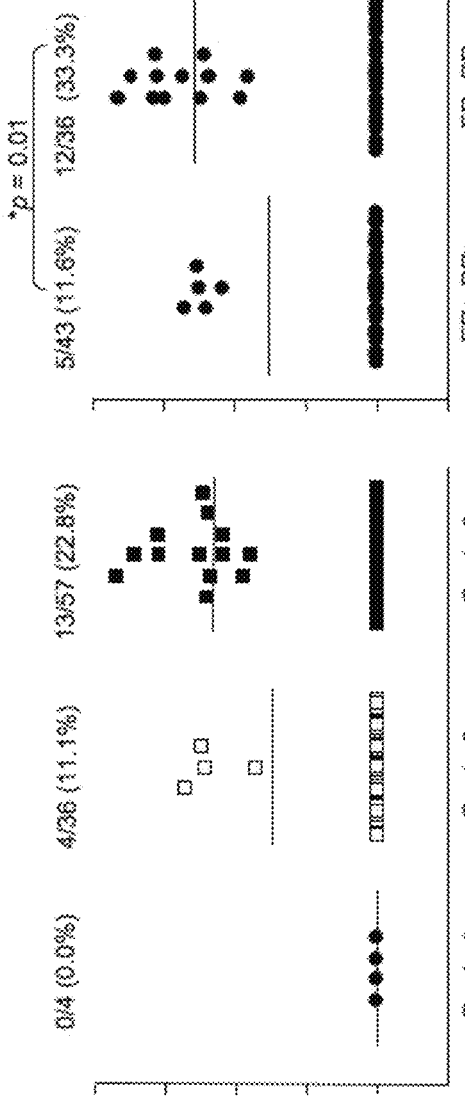
Figure 5D:
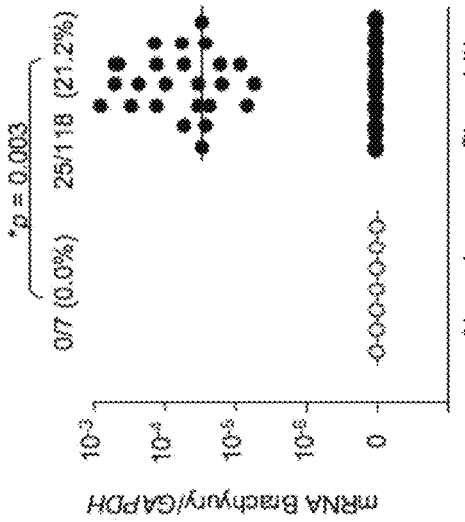
Figures 6A, 6B, 6C:
FIGS. 6A-6F. Immunohistochemical detection of Brachyury in primary breast carcinoma and metastatic tissues. Transmitted light photomicrographs of tissue sections stained for Brachyury expression in (A) a primary infiltrating ductal carcinoma, Grade 3 (patient 11); (B) a primary infiltrating ductal carcinoma, Grade 3 and (C) corresponding lymph node metastasis from the same patient (patient 6); (D, E) bone metastatic lesions from two different breast cancer patients (patients 22 and 23); (F) brain metastatic lesion from a breast cancer patient (patient 24). The brown signal represents staining for Brachyury. Magnification 20× (A-F).
Figures 6D, 6E, 6F:
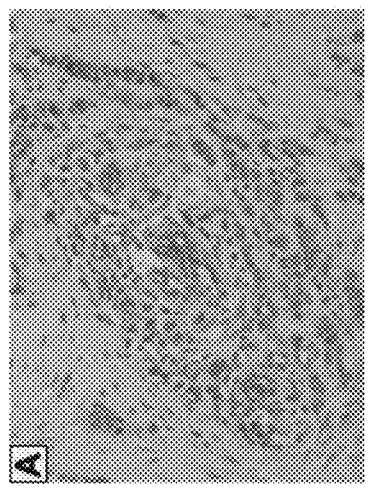

It is disclosed herein that Brachyury protein and Brachyury polypeptides of greater than 15 amino acids in length can be used to induce Brachyury-specific CD4+ T cells in vivo and ex vivo. It is also disclosed that Brachyury protein and Brachyury polypeptides can be used to stimulate the production of both Brachyury-specific CD4+ T cells and Brachyury-specific CD8+ T cells. Brachyury protein is expressed in numerous human cancers, such as cancer of the small intestine, stomach, kidney bladder, uterus, ovary, testes, lung, colon, prostate, bronchial tube, chronic lymphocytic leukemia (CLL), other B cell-based malignancies and breast cancer, such as infiltrating ductal carcinomas of the breast and thus the method disclosed herein can be used to treat or prevent these cancers. In specific non-limiting examples, the breast cancer is an estrogen receptor negative and progesterone receptor negative breast cancer. In additional non-limiting examples, the cancer is any cancer that is radiation resistant and/or chemotherapy resistant. The cancer can express Brachyury or have the potential to express Brachyury.

Non-pox non-yeast vectors encoding a Brachyury protein or a Brachyury polypeptide, and host cells expressing Brachyury are disclosed, these vectors and host cells can be used to induce CD4+ Brachyury-specific T cells and/or CD8+ T cells. In some non-limiting examples, these vectors are adenovirus vectors, alphavirus vectors, lentivirus vectors, poliovirus vectors, *Listeria* vectors, *Salmonella* vectors or measles virus vectors. In additional embodiments, host cells transformed with these vectors, and methods of using these proteins, polynucleotides, vectors, and host cells are provided. In some examples the host cells are *Salmonella* or *Listeria* host cells.

Thus, methods are provided for inducing CD4+ Brachyury-specific T cells and/or CD8+ T cells. The methods include the use of a Brachyury protein, Brachyury polypeptide, dendritic cells expressing Brachyury epitopes, nucleic acids encoding Brachyury protein and/or polypeptides, including non-pox non-yeast vectors encoding the Brachyury protein and/or the Brachyury polypeptide to induce the production of CD4+ Brachyury specific T cells. In some embodiments, methods are disclosed for treating a subject having cancer, such as, but not limited to, a cancer of the small intestine, stomach, kidney bladder, uterus, ovary, testes, lung, colon, prostate, bronchial tube, chronic lymphocytic leukemia (CLL), other B cell-based malignancies, or breast cancer, such as an infiltrating ductal carcinoma or estrogen receptor negative and progesterone receptor negative breast cancers. Any of these cancers can be chemotherapy resistant and/or radiation resistant. The cancer can express Brachyury or have the potential to express Brachyury. Methods are also disclosed for preventing these cancers.

These methods include inducing CD4+ Brachyury-specific T cells; the method can also include inducing CD8+ Brachyury-specific T cells. The Brachyury protein, Brachyury polypeptide, dendritic cells, nucleic acid, or non-pox non-yeast vector encoding the Brachyury protein can be administered to the subject either alone or in conjunction with a second agent, such as radiation therapy and/or chemotherapy.

In some embodiments, the Brachyury protein comprises an amino acid sequence at least 90% identical, or at least 95% identical, to the amino acid sequence set forth as SEQ ID NO: 1. In other embodiments, the Brachyury protein comprises, or consists of, the amino acid sequence set forth as SEQ ID NO: 1, the amino acid sequence set forth as SEQ ID NO: 1 without the N-terminal methionine, or the amino acid sequence set forth as SEQ ID NO: 1, with substitutions at position 177 (Asp vs. Gly, respectively), position 368 (Thr vs. Ser, respectively) and position 409 (Asn vs. Asp, respectively).

In further embodiments, a Brachyury polypeptide comprises at least 15 amino acids of the amino acid sequence set forth as SEQ ID NO: 1, such as at least 20, at least 30, at least 40, at least 50, at least 60, at least 70, at least 80, at least 90, at least 100, at least 200 amino acids of the amino acid sequence set forth as SEQ ID NO: 1, wherein the entirety of SEQ ID NO: 1 is not included in the polypeptide. In additional embodiments, a Brachyury polypeptide is 15 to 100 amino acids of SEQ ID NO: 1, such as 15 to 200 amino acids, 15 to 300 amino acids, 15 to 400 amino acids, or 15 to 435 amino acids of SEQ ID NO: 1.

In additional embodiments, methods are provided for inhibiting the growth of a cancer cell in a subject. These methods include contacting a dendritic cell with a protein comprising an amino acid sequence at least 90% identical to the amino acid sequence set forth as SEQ ID NO: 1, a polypeptide comprising at least 15 consecutive amino acids of the amino acid sequence set forth at SEQ ID NO: 1 that specifically binds a Major Histocompatibility Class (MHC class II) molecule, or a *Listeria* or *Salmonella* host cell expressing the protein, thereby preparing a specific antigen presenting cell. These methods also include administering the antigen presenting cell to the subject, thereby inducing an immune response and inhibiting the growth of the cancer cell.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Adenovirus: A virus of the family Adenoviridae, which are medium-sized (90-100 nm), nonenveloped icosahedral viruses composed of a nucleocapsid and a double-stranded linear DNA genome. The adenovirus genome is linear, non-segmented double-stranded (ds) DNA that is between 26 and 45 kb. This allows the virus to theoretically carry 22 to 40 genes. The linear dsDNA genome is able to replicate in the nucleus of mammalian cells using the host's replication machinery. However, adenoviral DNA does not integrate into the genome and is not replicated during cell division.

Adeno-associated Virus: Adeno-associated virus (AAV) is a small virus that infects humans and some other primate species. AAV is not currently known to cause disease and consequently the virus causes a very mild immune response.

AAV can infect both dividing and non-dividing cells and may incorporate its genome into that of the host cell. The AAV genome is built of single-stranded deoxyribonucleic acid (ssDNA), either positive- or negative-sensed, which is about 4.7 kilobase long. The genome comprises inverted terminal repeats (ITRs) at both ends of the DNA strand, and two open reading frames (ORFs): rep and cap. Rep is composed of four overlapping genes encoding Rep proteins required for the AAV life cycle, and Cap contains overlapping nucleotide sequences of capsid proteins: VP1, VP2 and VP3, which interact together to form a capsid of an icosahedral symmetry. For gene therapy, ITRs seem to be the only sequences required in cis next to the therapeutic gene: structural (cap) and packaging (rep) genes can be delivered in trans.

Adjuvant: A vehicle used to enhance antigenicity. Adjuvants include a suspension of minerals (alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants (for example see U.S. Pat. Nos. 6,194,388; 6,207,646; 6,214,806; 6,218,371; 6,239,116; 6,339,068; 6,406,705; and 6,429,199). Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L and 4-1 BBL. Another exemplary adjuvant is chitosan. Another adjuvant is *Bacillus*-Calmette-Guerin adjuvant.

Alphavirus: A virus that belongs to the group IV Togaviridae family of viruses. The alphaviruses are small, spherical, enveloped viruses with a genome of a single positive sense strand RNA. The total genome length ranges between 11,000 and 12,000 nucleotides, and has a 5' cap, and 3' poly-A tail. The four non-structural protein genes are encoded in the 5' two-thirds of the genome, while the three structural proteins are translated from a subgenomic mRNA colinear with the 3' one-third of the genome. The alphaviruses include the Ross River virus, Sindbis virus, Semliki Forest virus, and Venezuelan equine encephalitis virus.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation, but is generally not more than 20 amino acids in length. Methods of determining spatial conformation of epitopes include, for example, x-ray crystallography and 2-dimensional nuclear magnetic resonance.

An antigen can be a tissue-specific antigen, or a disease-specific antigen. These terms are not exclusive, as a tissue-specific antigen can also be a disease specific antigen. A tissue-specific antigen is expressed in a limited number of tissues, such as a single tissue. Specific, non-limiting examples of a tissue specific antigen are a prostate specific antigen, a uterine specific antigen, and/or a testes specific antigen. A tissue specific antigen may be expressed by more than one tissue, such as, but not limited to, an antigen that is expressed in more than one reproductive tissue, such as in both prostate and uterine tissue. A disease-specific antigen is expressed coincidentally with a disease process. Specific non-limiting examples of a disease-specific antigen are an antigen whose expression correlates with, or is predictive of, tumor formation, such as prostate cancer and/or uterine cancer and/or testicular cancer. A disease-specific antigen can be an antigen recognized by T cells or B cells.

Amplification: Of a nucleic acid molecule (e.g., a DNA or RNA molecule) refers to use of a technique that increases the number of copies of a nucleic acid molecule in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Antibody: Immunoglobulin molecules and immunologically active portions of immunoglobulin molecules, i.e., molecules that contain an antigen binding site that specifically binds (immunoreacts with) an antigen, such as Brachyury protein.

A naturally occurring antibody (e.g., IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the $V_L$, $V_H$, $C_L$ and $C_{H1}$ domains; (ii) an $F_d$ fragment consisting of the $V_H$ and $C_{H1}$ domains; (iii) an Fv fragment consisting of the VL and VH domains of a single arm of an antibody, (iv) a dAb fragment (Ward et al., *Nature* 341:544-546, 1989) which consists of a $V_H$ domain; (v) an isolated complementarity determining region (CDR); and (vi) a F(ab')$_2$ fragment, a bivalent fragment comprising two Fab fragments linked by a disulfide bridge at the hinge region.

Immunoglobulins and certain variants thereof are known and many have been prepared in recombinant cell culture (e.g., see U.S. Pat. Nos. 4,745,055; 4,444,487; WO 88/03565; EP 256,654; EP 120,694; EP 125,023; Faoulkner et al., *Nature* 298:286, 1982; Morrison, *J. Immunol.* 123: 793, 1979; Morrison et al., *Ann Rev. Immunol* 2:239, 1984). Humanized antibodies and fully human antibodies are also known in the art.

Animal: Living multi-cellular vertebrate organisms, a category that includes, for example, mammals and birds. The term mammal includes both human and non-human mammals. Similarly, the term "subject" includes both human and veterinary subjects.

Brachyury: The Brachyury gene is known to be important for the development of mesoderm during gastrulation. Brachyury is the founding member of a family of transcription factors, designated T-box transcription factors, characterized by a conserved DNA-binding domain (Papaioannou and Silver, *Bioessays* 20(1):9-19, 1998), that has an essential role in the formation and organization of mesoderm in vertebrates (see, for example, Kispert and Herrmann, *Embo J* 12(8):3211-20, 1993). For example, in *Xenopus*, Brachyury is an early-immediate response gene of mesoderm inducers, such as activin or TGF-β, and injection of Brachyury mRNA in embryos is sufficient to induce ectopic mesoderm development (Smith et al., *Cell* 67(1):79-87, 1991). In addition to the fundamental role of the T-box proteins in the control of developmental processes, several members of this family appear to be deregulated in cancer. The human Tbx2 gene has been reported to be amplified in pancreatic cancer cell lines (Mahlamaki et al., *Genes Chromosomes Cancer* 35(4):353-8, 2002) and over-expressed in BRCA-1- and BRCA-2-mutated breast tumors (Sinclair et al., *Cancer Res* 62(13):3587-9, 2002). Brachyury expression has been reported in human teratocarcinoma lines and chordomas (Vujovic et al, *J Pathol* 209(2): 157-65, 2006). Exemplary human brachyury amino acid and nucleic acid sequences are set forth in GENBANK® Accession No NP_003172 and GENBANK® Accession No. NM_003181, as available on Feb. 23, 2007, incorporated herein by reference, and are provided below.

Breast cancer: A neoplastic condition of breast tissue that can be benign or malignant. The most common type of breast cancer is ductal carcinoma. Ductal carcinoma in situ is a non-invasive neoplastic condition of the ducts. Lobular carcinoma is not an invasive disease but is an indicator that a carcinoma may develop. Infiltrating (malignant) carcinoma of the breast can be divided into stages (I IIA, IIB, IIIA, IIIB, and IV). Tumor size staging and node involvement staging can be combined into a single clinical staging number, as exemplified below.

| Tumor size staging | Node involvement staging | Clinical stage |
|---|---|---|
| T1 | N0 | I |
| T1 | N1 | IIA |
| T2 | N0 | IIA |
| T2 | N1 | IIB |
| T3 | N0 | IIB |
| T1-T2 | N2 | IIIA |
| T3 | N1 | IIIA |
| T3 | N2 | IIIA |
| T4 | N0-N2 | IIIB |

Breast carcinomas lose the typical histology and architecture of normal breast glands. Generally, carcinoma cells overgrow the normal cells and lose their ability to differentiate into glandular like structures. The degree of loss of differentiation in general is related to the aggressiveness of the tumor. For example, "in situ" carcinoma by definition retains the basement membrane intact, whereas as it progresses to "invasive", the tumor shows breakout of basement membranes. Thus one would not expect to see, within breast carcinomas, staining of a discrete layer of basal cells as seen in normal breast tissue. For a discussion of the physiology and histology of normal breast and breast carcinoma, see Ronnov-Jessen, L., Petersen, O. W. & Bissell, M. J. Cellular changes involved in conversion of normal to malignant breast: importance of the stromal reaction. Physiol Rev 76, 69-125 (1996).

Breast cancers can be divided into groups based on their expression profiles. Basal-type carcinomas usually are negative for expression of estrogen receptor (ER) and negative for expression of HER2 (erbB2) and progesterone receptor (PR), and thus are referred to as "triple-negative breast cancers" or "TNBC." This type of breast cancer is also denoted $ER^-/HER2^-/PR^-$ and represents about 15-20% of all breast cancer, and generally cannot be treated using Her2 targeted or estrogen targeted therapies. It is believed that the aggressive nature of this cancer is correlated with an enrichment for cancer stem cells (CSC) with a $CD44^+CD24^{-/lo}$ phenotype. In some embodiments, basal carcinomas are negative for expression of progesterone receptor (PR), positive for expression of epidermal growth factor receptor (EGFR), and positive for expression of cytokeratin 5 (CK5). This phenotype is denoted as follows: $ER^-/PR^-/HER2^-/CK5^+/EGFR^+$.

Cancer or Tumor: A malignant neoplasm that has undergone characteristic anaplasia with loss of differentiation, increased rate of growth, invasion of surrounding tissue, and is capable of metastasis. For example, prostate cancer is a malignant neoplasm that arises in or from prostate tissue, ovarian cancer is a malignant neoplasm that arises in or from ovarian tissue, colon cancer is a malignant neoplasm that arises in or from colon tissue, and lung cancer is a malignant neoplasm that arises in the lungs. Residual cancer is cancer that remains in a subject after any form of treatment given to the subject to reduce or eradicate the cancer. Metastatic cancer is a cancer at one or more sites in the body other than the site of origin of the original (primary) cancer from which the metastatic cancer is derived. Cancer includes, but is not limited to, sarcomas and carcinomas. Prostate cancer is a malignant tumor, generally of glandular origin, of the prostate. Prostate cancers include adenocarcinomas and small cell carcinomas.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Chemotherapeutic agents: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating breast and/or prostate cancer. In one embodiment, a chemotherapeutic agent is radioactive compound. One of skill in the art can readily identify a chemotherapeutic agent of use (e.g. see Slapak and Kufe, *Principles of Cancer Therapy*, Chapter 86 in Harrison's Principles of Internal Medicine, 14th edition, Perry et al., *Chemotherapy*, Ch. 17 in Abeloff, Clinical Oncology $2^{nd}$ ed., © 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). Combination chemotherapy is the administration of more than one agent to treat cancer, such as the administration of a non-pox non-yeast vector encoding Brachyury in combination with a radioactive or chemical compound to a subject.

Conservative variants: "Conservative" amino acid substitutions are those substitutions that do not substantially affect or decrease an activity or antigenicity of an antigenic epitope of Brachyury. Specific, non-limiting examples of a conservative substitution include the following examples:

| Original Residue | Conservative Substitutions |
|---|---|
| Al | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variant also includes the use of a substituted amino acid in place of an unsubstituted parent amino acid, provided that antibodies raised to the substituted polypeptide also immunoreact with the unsubstituted polypeptide, and/or that the substituted polypeptide retains the function of the unsubstituted polypeptide. Non-conservative substitutions are those that reduce an activity or antigenicity.

CD4: Cluster of differentiation factor 4, a T cell surface protein that mediates interaction with the MHC Class II molecule. CD4 also serves as the primary receptor site for HIV on T cells during HIV infection. Cells that express CD4 are often helper T cells.

CD8: Cluster of differentiation factor 8, a T cell surface protein that mediates interaction with the MHC Class I molecule. Cells that express CD8 are often cytotoxic T cells.

Consists Essentially Of/Consists Of: With regard to a polypeptide or protein, a polypeptide (or protein) that consists essentially of a specified amino acid sequence if it does not include any additional amino acid residues. However, the polypeptide (or protein) can include additional non-peptide components, such as labels (for example, fluorescent, radioactive, or solid particle labels), sugars or lipids. With regard to a polypeptide or protein, a polypeptide or protein that consists of a specified amino acid sequence does not include any additional amino acid residues, nor does it include additional non-peptide components, such as lipids, sugars or labels.

Costimulatory molecule: Although engagement of the TCR with peptide-MHC delivers one signal to the T cell, this signal alone can be insufficient to activate the T cell. Costimulatory molecules are molecules that, when bound to their ligand, deliver a second signal required for the T cell to become activated. The most well-known costimulatory molecule on the T cell is CD28, which binds to either B7-1 (also called CD80) or B7-2 (also known as CD86). An additional costimulatory molecule is B7-3. Accessory molecules that also provide a second signal for the activation of T cells include intracellular adhesion molecule (ICAM-1 and ICAM-2), leukocyte function associated antigen (LFA-1, LFA-2 and LFA-3). Integrins and tumor necrosis factor (TNF) superfamily members can also serve as co-stimulatory molecules.

Degenerate variant: A polynucleotide encoding an epitope of Brachyury that includes a sequence that is degenerate as a result of the genetic code. There are 20 natural amino acids, most of which are specified by more than one codon. Therefore, all degenerate nucleotide sequences are included in this disclosure as long as the amino acid sequence of the Brachyury protein encoded by the nucleotide sequence is unchanged.

Dendritic cell (DC): Dendritic cells are the principle antigen presenting cells (APCs) involved in primary immune responses. Dendritic cells include plasmacytoid dendritic cells and myeloid dendritic cells. Their major function is to obtain antigen in tissues, migrate to lymphoid organs and present the antigen in order to activate T cells. Immature dendritic cells originate in the bone marrow and reside in the periphery as immature cells.

Diagnostic: Identifying the presence or nature of a pathologic condition, such as, but not limited to, a cancer, such as small intestine, stomach, kidney, bladder, uterus, ovary, testes, lung, colon or prostate cancer. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" means predicting the probability of development (for example, severity) of a pathologic condition, such as prostate cancer, or metastasis.

Epithelial-to-Mesenchymal Transition: The epithelium is the covering of internal and external surfaces of the body, including the lining of vessels and other small cavities, that consists of cells joined by biological cementing substances. Generally, fully differentiated epithelial cells express proteins characteristic of a differentiated phenotype, such as insulin, and have a limited capacity to proliferate. The mesenchyme is the meshwork of loosely organized embryonic connective tissue in the mesoderm from which are formed the connective tissues of the body, along with the blood vessels and lymphatic vessels. Vimentin is one marker of mesenchymal cells. Mesenchymal cells generally have a greater capacity to proliferate in vitro than epithelial cells and are not fully differentiated. An "epithelial-to-mesenchymal" transition is a biological process wherein a cell, or a population of cells, from an epithelial phenotype convert to a less differentiated mesenchymal phenotype. A "mesenchymal-to-epithelial" transition is a biological process wherein a cell, or a population of cells, convert from a less differentiated mesenchymal phenotype to a more differentiated epithelial phenotype.

Epitope: An antigenic determinant. These are particular chemical groups or peptide sequences on a molecule that are antigenic (that elicit a specific immune response). An antibody specifically binds a particular antigenic epitope on a polypeptide. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or 8 to 10 amino acids, and generally not more than 20 amino acids, in a unique spatial conformation. Methods of determining spatial conformation of epitopes include, for example, x-ray crystallography and 2-dimensional nuclear magnetic resonance. See, e.g., "Epitope Mapping Protocols" in *Methods in Molecular Biology*, Vol. 66, Glenn E. Morris, Ed (1996). In one embodiment, an epitope binds an MHC molecule, such as an HLA molecule or a DR molecule. These molecules bind polypeptides having the correct anchor amino acids separated by about eight to about ten amino acids, such as nine amino acids.

Estrogen Receptor (ER): A receptor that is activated by the hormone 17β-estradiol (estrogen). The main function of the estrogen receptor is as a DNA binding transcription factor that regulates gene expression. Estrogen receptors are over-expressed in around 70% of breast cancer cases, referred to as "ER positive" or "ER$^+$." Therapy for ER$^+$ breast cancer involves selective estrogen receptor modulators (SERMS) which behave as ER antagonists in breast tissue or aromatase inhibitors. ER status is also used to determine sensitivity of breast cancer lesions to tamoxifen and aromatase inhibitors.

Expression Control Sequences: Nucleic acid sequences that regulate the expression of a heterologous nucleic acid sequence to which they are operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like can be used. In one embodiment, when cloning in mammalian cell systems, promoters derived from the genome of mammalian cells (such as the metallothionein promoter) or from mammalian viruses (such as the retrovirus long terminal repeat; the adenovirus late promoter; the vaccinia virus 7.5K promoter) can be used. Promoters are also disclosed herein that are effective when included in a poxviral vector. Promoters produced by recombinant DNA or synthetic techniques can also be used to provide for transcription of the nucleic acid sequences.

HER2: Human Epidermal growth factor Receptor 2 (Her2) is also known as Her 2/neu (or ErbB-2, ERBB2). It is a member of the ErbB protein family (also known as the epidermal growth factor receptor family). HER2 has also been designated as CD340 (cluster of differentiation 340) and p185. HER2 is notable for its role in the pathogenesis of breast cancer and as a target of treatment. It is a cell membrane surface-bound receptor tyrosine kinase and is normally involved in the signal transduction pathways leading to cell growth and differentiation.

Approximately 15-20 percent of breast cancers have an amplification of the HER2 gene or overexpression of its protein product. Overexpression of this receptor in breast cancer has been associated with increased disease recurrence and worse prognosis. Because of its prognostic role, breast tumors are routinely checked for overexpression of HER2. Overexpression also occurs in other cancer such as ovarian cancer, stomach cancer, and biologically aggressive forms of uterine cancer, such as uterine serous endometrial carcinoma.

Heterologous: Originating from separate genetic sources or species. A polypeptide that is heterologous to Brachyury originates from a nucleic acid that does not encode Brachyury. In specific, non-limiting examples, with regard to a polypeptide comprising Brachyury, a heterologous amino acid sequence includes a 3-galactosidase, a maltose binding protein, and albumin, hepatitis B surface antigen, or an immunoglobulin amino acid sequence. Generally, an antibody that specifically binds to a protein of interest, such as Brachyury, will not specifically bind to a heterologous protein.

Host cells: Cells in which a vector can be propagated and its DNA expressed. The cell may be prokaryotic or eukaryotic. The cell can be mammalian, such as a human cell. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunogenic polypeptide and Immunogenic Protein: A protein or peptide which comprises an allele-specific motif or other sequence such that the peptide will bind an MHC molecule and induce a T cell response, or a B cell response (e.g. antibody production) against the antigen.

Immunogenic peptides are generally 7 to 20 amino acids in length, such as 9 to 12 amino acids in length. In one example, an immunogenic polypeptide includes an allele-specific motif or other sequence such that the peptide will bind an MHC molecule and induce a T cell response against the antigen (protein) from which the immunogenic polypeptide is derived. In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide. In one example, an immunogenic "Brachyury polypeptide" is a series of contiguous amino acid residues from the Brachyury protein generally between 7 and 20 amino acids in length, such as about 8 to 11 residues in length. Specific immunogenic Brachyury polypeptides are 9 or 10 amino acid residues in length, or at most 12 amino acids in length.

Immunogenic peptides and proteins can also be identified by measuring their binding to a specific MHC protein (Class I or Class II) and by their ability to stimulate CD4 and/or CD8 when presented in the context of the MHC protein. The characteristics of immunogenic polypeptides, are disclosed, for example, in PCT Publication No. WO 00/12706, which is incorporated herein by reference.

Generally, an immunogenic Brachyury protein includes a number of immunogenic polypeptides, and can be used to induce an immune response in a subject, such as a CD4+ T cell response. In one example, an immunogenic Brachyury protein, when bound to a Major Histocompatibility Complex Class II molecule, activates CD4+ T cells against cells expressing wild-type Brachyury protein, and/or when bound to a Major Histocompatibility Complex Class I molecule, activates cytotoxic T lymphocytes (CTLs) against cells expressing wild-type Brachyury protein. Induction of CTLs using synthetic peptides and CTL cytotoxicity assays are known in the art, see U.S. Pat. No. 5,662,907, which is incorporated herein by reference.

Immunogenic composition: A composition, such as a composition comprising a Brachyury protein or a nucleic acid encoding the Brachyury protein, that induces a measurable T cell response against cells expressing Brachyury protein, or induces a measurable B cell response (such as production of antibodies that specifically bind Brachyury) against a Brachyury protein. For in vitro use, the immunogenic composition can consist of the isolated nucleic acid, vector including the nucleic acid/or immunogenic protein. For in vivo use, the immunogenic composition will typically comprise the nucleic acid, vector including the nucleic acid, and or immunogenic protein, in pharmaceutically acceptable carriers, and/or other agents. An immunogenic composition can optionally include an adjuvant, a costimulatory molecule, or a nucleic acid encoding a costimulatory molecule.

Immunostimulatory molecule: Molecules that stimulate the cells of the immune system including costimulatory molecules, cytokines and immunostimulatory nucleic acids, such as those that include a CpG motif.

Inhibiting or treating a disease: Inhibiting a disease, such as cancer growth, refers to inhibiting the full development of a disease. In several examples, inhibiting a disease refers to lessening symptoms of a cancer, such as preventing the development of paraneoplastic syndrome in a person who is known to have a cancer, or lessening a sign or symptom of the cancer or reducing cancer volume. "Treatment" refers to a therapeutic intervention that ameliorates a sign or symptom of a disease or pathological condition related to the disease, such as the cancer.

Isolated: An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule to facilitate detection of that molecule. Specific, non-limiting examples of labels include fluorescent tags, enzymatic linkages, and radioactive isotopes.

Lentiviral vector: Lentiviruses are a subclass of Retroviruses. Lentiviral vectors can integrate into the genome of non-dividing cells. This feature of Lentiviruses is unique, as other Retroviruses can infect only dividing cells. The viral genome in the form of RNA is reverse-transcribed when the virus enters the cell to produce DNA, which is then inserted into the genome at a random position by the viral integrase enzyme. The vector, now called a provirus, remains in the genome and is passed on to the progeny of the cell when it divides. Lentiviral vectors include HIV-1, HIV-2, SIV (simian immunodeficiency virus), EIAV (equine infectious anaemia virus), FIV (feline immunodeficiency virus), CAEV (Caprine arthritis encephalitis virus), and VMV (Visna/maedi virus) vectors. Lentiviral vectors also encompass chimeric lentiviruses derived from at least two different lentiviruses.

Linker sequence: A linker sequence is an amino acid sequence that covalently links two polypeptide domains. Linker sequences can be included in the between the Brachyury proteins disclosed herein to provide rotational freedom to the linked polypeptide domains. By way of example, in a recombinant molecule comprising two Brachyury proteins, linker sequences can be provided between them, so that the proteins comprises Brachyury protein-linker-Brachyury protein. Linker sequences, which are generally between 2 and 25 amino acids in length, are well known in the art and include, but are not limited to, four glycines and a serine spacer described by Chaudhary et al., *Nature* 339:394-397, 1989.

*Listeria*: A Gram-positive bacilli. The genus *Listeria* currently contains seven species: *L. grayi. L. innocua, L. ivanovii, L. monocytogenes, L. murrayi, L. seeligeri*, and *L. welshimeri*. *L. monocytogenes* is an intracellular bacterium that has been used as a vector to deliver genes in vitro.

Lymphocytes: A type of white blood cell that is involved in the immune defenses of the body. There are two main types of lymphocytes: B cells and T cells.

Major Histocompatibility Complex (MHC): A generic designation meant to encompass the histocompatability antigen systems described in different species, including the human leukocyte antigens ("HLA").

Mammal: This term includes both human and non-human mammals. Similarly, the term "subject" includes both human and veterinary subjects.

Neoplasm: An abnormal cellular proliferation, which includes benign and malignant tumors, as well as other proliferative disorders.

Oligonucleotide: A linear polynucleotide sequence of up to about 100 nucleotide bases in length.

Open reading frame (ORF): A series of nucleotide triplets (codons) coding for amino acids without any internal termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence, such as a sequence that encodes a Brachyury protein. Generally, operably linked DNA sequences are contiguous and, where necessary to join two protein-coding regions, in the same reading frame.

Peptide Modifications: Brachyury proteins include synthetic embodiments of peptides described herein. In addition, analogs (non-peptide organic molecules), derivatives (chemically functionalized peptide molecules obtained starting with the disclosed peptide sequences) and variants (homologs) of these proteins can be utilized in the methods described herein. Each protein or polypeptide of this disclosure is comprised of a sequence of amino acids, which may be either L- and/or D-amino acids, naturally occurring and otherwise.

Protein and polypeptides can be modified by a variety of chemical techniques to produce derivatives having essentially the same activity as the unmodified peptides, and optionally having other desirable properties. For example, carboxylic acid groups of the protein, whether carboxyl-terminal or side chain, can be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, can be in the form of a pharmaceutically-acceptable acid addition salt, such as the HCl, HBr, acetic, benzoic, toluene sulfonic, maleic, tartaric and other organic salts, or can be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into proteins and polypeptides to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of a Brachyury protein having measurable or enhanced ability to generate an immune response. For computer modeling applications, a pharmacophore is an idealized three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs," in Klegerman & Groves, eds., 1993, *Pharmaceutical Biotechnology*, Interpharm Press: Buffalo Grove, Ill., pp. 165-174 and *Principles of Pharmacology*, Munson (ed.) 1995, Ch. 102, for descriptions of techniques used in CADD. Also included are mimetics prepared using such techniques.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

A "therapeutically effective amount" is a quantity of a composition or a cell to achieve a desired effect in a subject being treated. For instance, this can be the amount of Brachyury protein or a vector encoding a Brachyury protein necessary to induce an immune response, inhibit cancer growth, reduce cancer volume, prevent cancer, or to measurably alter outward symptoms of the cancer. When administered to a subject, a dosage will generally be used that will achieve target tissue concentrations (for example, in lymphocytes) that has been shown to achieve an in vitro effect.

Plasmid: A DNA molecule that is separate from, and can replicate independently of, the chromosomal DNA. They are double-stranded and, in many cases, circular. Generally, a gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location.

Poliovirus: A human enterovirus and member of the family of Picornaviridae; the wild-type poliovirus causes poliomyelitis. Poliovirus is composed of an RNA genome and a protein capsid. The wild-type genome is a single-stranded positive-sense RNA genome that is about 7500 nucleotides long. The viral particle is about 30 nanometres in diameter with icosahedral symmetry.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Polypeptide: A chain of amino acids, generally greater than eight amino acids in length, such as greater than fifteen amino acids in length, which can be post-translationally modified (e.g., glycosylation or phosphorylation) that is not the complete wild-type protein. A polypeptide can be at least 15, at least 20, at least 30, at least 40, at least 50, at least 60, at least 70, at least 80, at least 90, at least 100, at least 200 amino acids in length. Thus, a polypeptide can be, for example, 20-300, 30-300, 40-300, 50-300, 60-300, 70-300, 80-300, 90-300, 100-300, or 200-300 amino acids in length. In additional embodiments, a polypeptide is 15 to 10-, 20-100, 25-100, 30-100, 35-100, 40-100, 45-100, 50-100, 55-100, 60-100, 65-100, 70-100, 75-100, 80-100, 85-100, 90-100 or 95-100 amino acids in length. In further embodiments a polypeptide is up to 433, 434 or 435 amino acids in length.

Protein: A chain of amino acids, generally greater than 100 amino acids in length, that has a specific function in a cell and is a complete wild-type protein or the complete wild type protein without the N-terminal methionine. A protein can be post-translationally modified. In one embodiment, the protein is a Brachyury protein.

Measles virus (Morbillivirus): A negative strand RNA virus belonging the Paramyxoviridae family that causes measles. Heterologous genes can be inserted into the viral genome. The non segmented genome of measles virus has an anti-message polarity which results in a genomic RNA which, when purified, is not translated either in vivo or in vitro and is not infectious.

Poxvirus: Four genera of poxviruses infect humans: orthopox, parapox, yatapox, molluscipox. Orthopox includes smallpox virus (variola), vaccinia virus, cowpox virus, and monkeypox virus. Parapox includes the orf virus, pseudocowpox, and bovine papular stomatitis virus. Yatapox includes tanapox virus, and yaba monkey tumor virus. Molluscipox includes molluscum contagiosum virus (MCV). Poxviridae viral particles (virions) are generally enveloped (external enveloped virion—EEV), though the intracellular mature virion (IMV) form of the virus, which contains different envelope, is also infectious.

Vaccinia virus is used as an effective tool for heterologous protein expression. Vaccinia virus enters cells mainly by cell fusion. This virus contains three classes of genes, early, intermediate and late, that are transcribed by viral RNA polymerase and associated transcription factors. Vaccinia virus replicates its genome in cytoplasm of the infected cells and after late gene expression virion morphogenesis produces intracellular mature virion (IMV) that contains envelope, although the origin of the envelope membrane is still unknown. IMV is transported to Golgi, wherein the intracellular enveloped virus (IEV) is formed. IEV transports along microtubules to reach cell periphery and fuse with plasma membrane to become cell-associated enveloped virus (CEV) that triggers actin tails on cell surfaces or forms the extracellular enveloped virion (EEV), which is believed to be important for long range dissemination within the host organism.

A "non-poxviral vector" is a vector that is not included in the four genera of poxviruses.

Progesterone receptor (PR): A receptor, also known as NR3C3 (nuclear receptor subfamily 3, group C, member 3), that is a steroid receptor that specifically binds progesterone. The progesterone receptor is not expressed on triple negative basal breast cancer cells.

Probes and primers: A probe comprises an isolated nucleic acid attached to a detectable label or reporter molecule. Primers are short nucleic acids, preferably DNA oligonucleotides, of about 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, for example by polymerase chain reaction (PCR) or other nucleic-acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers can be selected that comprise about 20, 25, 30, 35, 40, 50 or more consecutive nucleotides.

Purified: Brachyury proteins and nucleic acids as disclosed herein can be purified (and/or synthesized) by any of the means known in the art (see, e.g., *Guide to Protein Purification*, ed. Deutscher, *Meth. Enzymol.* 185, Academic Press, San Diego, 1990; and Scopes, *Protein Purification: Principles and Practice*, Springer Verlag, New York, 1982). Substantial purification denotes purification from other proteins, nucleic acids, or cellular components. The term purified does not require absolute purity; rather, it is intended as a relative term. A substantially purified protein is at least about 60%, 70%, 80%, 90%, 95%, 98% or 99% pure. Thus, in one specific, non-limiting example, a substantially purified protein is at least 90% free of other proteins or cellular components. In additional embodiments, a nucleic acid or cell preparation is purified such that the nucleic acid or cell represents at least about 60% (such as, but not limited to, 70%, 80%, 90%, 95%, 98% or 99%) of the total nucleic acid or cell content of the preparation, respectively. Thus, in one specific, non-limiting example, a substantially purified nucleic acid is at least 90% free of other nucleic acids or cellular components.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Replication defective: A viral vector that cannot further replicate and package its genomes. In one non-limiting example, when the cells of a subject are infected with a vector, a heterologous in the vector is expressed in the subject's cells, however, due to the fact that the patient's cells lack essential genes. Examples are the rev and cap genes for AAV, or gag, pol and env for a lentivirus. Generally, the genes necessary to replicate and package are not present, such that and wild-type virus cannot be formed in the subject's cells.

*Salmonella*: A genus of rod-shaped, Gram-negative, non-spore-forming, predominantly motile enterobacteria with diameters around 0.7 to 1.5 μm, lengths from 2 to 5 μm, and flagella which grade in all directions (i.e. peritrichous). They are chemoorganotrophs, obtaining their energy from oxidation and reduction reactions using organic sources, and are facultative anaerobes. *Salmonella* can be used as delivery vector for therapeutic proteins, by including plasmids, such as those with truncated tetA genes in the host cell. Attenuated *S. typhimurium* can be transformed with DNA plasmids, such as, but not limited to, pIRES (Invitrogen) and used as a carrier for delivery of polypeptides and proteins.

Selectively hybridize: Hybridization under moderately or highly stringent conditions that excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (for example, GC v. AT content), and nucleic acid type (for example, RNA versus DNA) of the hybridizing regions of the nucleic acids can be considered in selecting hybridization conditions. An additional consideration is whether one of the nucleic acids is immobilized, for example, on a filter.

A specific example of progressively higher stringency conditions is as follows: 2×SSC/0.1% SDS at about room temperature (hybridization conditions); 0.2×SSC/0.1%/SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (e.g., *Molecular Cloning: A Laboratory Manual,* 2nd ed., vol. 1-3, ed. Sambrook et al., Cold Spring Harbor Laboratory Press, Cold Spring Harbor, N.Y., 1989). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a Brachyury protein will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a Brachyury protein are typically characterized by possession of at least 75%, for example at least 80%, sequence identity, or at least 90% sequence identity, counted over the full length alignment with the amino acid sequence of Brachyury using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and can possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Specific binding agent: An agent that binds substantially only to a defined target. Thus a Brachyury specific binding agent is an agent that binds substantially to a Brachyury protein. In one embodiment, the specific binding agent is a monoclonal or polyclonal antibody that specifically binds Brachyury protein.

T Cell: A white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4) and is MHC Class II restricted. These cells, often called helper T cells, help orchestrate the immune response, including antibody responses as well as killer T cell responses. $CD8^+$ T cells carry the "cluster of differentiation 8" (CD8) marker and are MHC Class I restricted. In one embodiment, a CD8 T cell is a cytotoxic T lymphocyte. In another embodiment, a CD8 cell is a suppressor T cell.

Therapeutically active protein: An agent composed of amino acids, such as a Brachyury protein, that causes induction of an immune response, as measured by clinical response (for example increase in a population of immune cells, increased cytolytic activity against cells that express Brachyury, or measurable reduction of tumor burden). Therapeutically active molecules can also be made from nucleic acids. Examples of a nucleic acid based therapeutically active molecule is a nucleic acid sequence that encodes a Brachyury protein, wherein the nucleic acid sequence is operably linked to a control element such as a promoter.

In one embodiment, a therapeutically effective amount of a composition, such as a Brachyury protein or a vector encoding the Brachyury protein, is an amount used to generate an immune response, or to treat or prevent cancer in a subject. In several examples, "treatment" refers to a therapeutic intervention that ameliorates a sign or symptom of a cancer, or a reduction in tumor burden.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker gene and other genetic elements known in the art. Vectors include plasmid vectors, including plasmids for expression in gram negative and gram positive bacterial cell. Exemplary vectors include those for expression in *E. coli* and *Salmonella*. Vectors also include poxviral vectors, such as, but are not limited to, retrovirus, orthopox, avipox, fowlpox, capripox, suipox, adenoviral, herpes virus, alpha virus, baculovirus, Sindbis virus, vaccinia virus and poliovirus vectors. Vectors also include vectors for expression in yeast cells.

Yeast: Unicellular microorganisms that belong to one of three classes: Ascomycetes, Basidiomycetes and Fungi Imperfecti. A yeast can be a non-pathogenic strain such as *Saccharomyces cerevisiae*. Yeast strains include *Saccharomyces, Candida* (which can be pathogenic), *Cryptococcus, Hansenula, Kluyveromyces, Pichia, Rhodotorula, Schizosaccharomyces* and *Yarrowia*. Yeast genera include *Saccharomyces, Candida, Hansenula. Pichia* or *Schizosaccharomyces*. Species of yeast strains include *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris. Rhodotorula rubra, Schizosaccharomyces pombe,* and *Yarrowia lipolytica*.

Yeast vehicles" include, but are not limited to, a live intact (whole) yeast microorganism (i.e., a yeast cell having all its components including a cell wall), a killed (dead) or inactivated intact yeast microorganism, or derivatives of intact yeast including: a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus and cytoplasm), a subcellular yeast membrane extract or fraction thereof (also referred to as a yeast membrane particle or a subcellular yeast particle), any other yeast particle, or a yeast cell wall preparation. A "non-yeast vector" is a composition that does not include yeast vehicles.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. The term "comprises" means "includes." Similarly, comprising "A or B" includes "A," "B," and both "A and B." It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Immunogenic Brachyury Protein and Brachyury Polypeptides

Brachyury (also known as "T-protein") is a protein which is transcribed in the mesoderm. In one embodiment, the Brachyury protein has a sequence set forth as:

(SEQ ID NO: 1)
MSSPGTESAGKSLQYRVDHLLSAVENELQAGSEKGDPTERELRVGLE

ESELWLRFKELTNEMIVTKNGRRMFPVLKVNVSGLDPNAMYSFLLDF

VAADNHRWKYVNGEWVPGGKPEPQAPSCVYIHPDSPNFGAHWMKAPV

SFSKVKLTNKLNGGGQIMLNSLHKYEPRIHIVRVGGPQRMITSHCFP

-continued

ETQFIAVTAYQNEEITALKIKYNPFAKAFLDAKERSDHKEMMEEPGD

SQQPGYSQWGWLLPGTSTLCPPANPHPQFGGALSLPSTHSCDRYPTL

RSHRSSPYPSPYAHRNNSPTYSDNSPACLSMLQSHDNWSSLGMPAHP

SMLPVSHNASPPTSSSQYPSLWSVSNGAVTPGSQAAAVSNGLGAQFF

RGSPAHYTPLTHPVSAPSSSGSPLYEGAAAATDIVDSQYDAAAQGRL

IASWTPVSPPSM
(see also GENBANK ® Accession No NP_003172 and GENBANK ® Accession No. NM_003181, as available on Feb. 23, 2007, incorporated herein by reference).

Using the genetic code, one of skill in the art can readily produce a nucleic acid sequence encoding Brachyury. In one example, Brachyury protein is encoded by a nucleic acid having a sequence set forth as:

(SEQ ID NO: 2)
tttgcttttg cttatttccg tccatttccc tctctgcgcg cggaccttcc ttttccagat ggtgagagcc gcggggacac ccgacgccgg ggcaggctga tccacgatcc tgggtgtgcg taacgccgcc tggggctccg tgggcgaggg acgtgtgggg acaggtgcac cggaaactgc cagactggag agttgaggca tcggaggcgc gagaacagca ctactactgc ggcgagacga gcgcgcgca tcccaaagcc cggccaaatg cgctcgtccc tgggagggga gggaggcgcg cctggagcgg ggacagtctt ggtccgcgcc ctcctcccgg gtctgtgccg ggacccggga cccgggagcc gtcgcaggtc tcggtccaag gggcccttt tctcggaagg gcggcggcca agagcaggga aggtggatct caggtagcga gtctgggctt cggggacggc ggggagggga gccggacggg aggatgagct cccctggcac cgagagcgcg ggaaagagcc tgcagtaccg agtggaccac ctgctgagcg ccgtggagaa tgagctgcag gcgggcagcg agaagggcga ccccacagag cgcgaactgc gcgtgggcct ggaggagagc gagctgtggc tgcgcttcaa ggagctcacc aatgagatga tcgtgaccaa gaacggcagg aggatgtttc cggtgctgaa ggtgaacgtg tctggcctgg accccaacgc catgtactcc ttcctgctgg acttcgtggc ggcggacaac caccgctgga agtacgtgaa cggggaatgg gtgccggggg gcaagccgga gccgcaggcg cccagctgcg tctacatcca cccccgactcg cccaacttcg gggcccactg gatgaaggct cccgtctcct tcagcaaagt caagctcacc aacaagctca acggaggggg ccagatcatg ctgaactcct tgcataagta tgagcctcga atccacatag tgagagttgg gggtccacag cgcatgatca ccagccactg cttccctgag acccagttca tagcggtgac tgcttatcag aacgaggaga tcacagctct taaaattaag

```
tacaatccat ttgcaaaagc tttccttgat gcaaaggaaa gaagtgatca caaagagatg atggaggaac ccggagacag ccagcaacct gggtactccc aatgggggtg gcttcttcct ggaaccagca ccctgtgtcc acctgcaaat cctcatcctc agtttggagg tgccctctcc ctcccctcca cgcacagctg tgacaggtac ccaaccctga ggagccaccg gtcctcaccc tacccagcc cctatgctca tcggaacaat tctccaacct attctgacaa ctcacctgca tgtttatcca tgctgcaatc ccatgacaat tggtccagcc ttggaatgcc tgcccatccc agcatgctcc ccgtgagcca caatgccagc ccacctacca gctccagtca gtacccagc ctgtggtctg tgagcaacgg cgccgtcacc ccgggctccc aggcagcagc cgtgtccaac gggctggggg cccagttctt ccggggctcc cccgcgcact acacacccct cacccatccg gtctcggcgc cctcttcctc gggatcccca ctgtacgaag gggcggccgc ggccacagac atcgtggaca gccagtacga cgccgcagcc caaggccgcc tcatagcctc atggacacct gtgtcgccac cttccatgtg aagcagcaag gcccaggtcc cgaaagatgc agtgactttt tgtcgtggca gccagtggtg actggattga cctactaggt acccagtggc agtctcaggt taagaaggaa atgcagcctc agtaacttcc ttttcaaagc agtggaggag cacacggcac cttttccccag agcccagca tcccttgctc acacctgcag tagcggtgct gtcccaggtg gcttacagat gaacccaact gtggagatga tgcagttggc ccaacctcac tgacggtgaa aaaatgtttg ccagggtcca gaaacttttt ttggtttatt tctcatacag tgtattggca actttggcac accagaattt gtaaactcca ccagtcctac tttagtgaga taaaaagcac actcttaatc ttcttccttg ttgctttcaa gtagttagag ttgagctgtt aaggacagaa taaaatcata gttgaggaca gcaggtttta gttgaattga aaatttgact gctctgcccc ctagaatgtg tgtattttaa gcatatgtag ctaatctctt gtgttgttaa actataactg tttcatattt ttcttttgac aaagtagcca aagacaatca gcagaaagca ttttctgcaa aataaacgca atatgcaaaa tgtgattcgt ccagttatta gtgaagcccc tcctttttgtg agtatttact gtttattg.
```

In other embodiments, Brachyury protein has an amino acid sequence at least 90% identical to SEQ ID NO: 1, for example a polypeptide that is at least or about 91%, 92%, 93%, 94%, 95%, 96%, 97%, 98% or 99% identical to SEQ ID NO: 1. Brachyury proteins are disclosed herein that can be used to induce an immune response (are immunogenic), wherein the Brachyury protein can produce a Brachyury-specific CD4+ T cell response. In some embodiments, the Brachyury protein produces a Brachyury specific CD4+ T cell response and a Brachyury Specific CD8+ T cell response.

SEQ ID NO: 1 provides an exemplary sequence for the full-length Brachyury; another full length Brachyury is this amino acid sequence with the N-terminal methionine removed. In some examples, the Brachyury protein includes the amino acid sequence set forth as SEQ ID NO: 1, with substitutions at position 177 (Asp vs. Gly, respectively), position 368 (Thr vs. Ser, respectively) and position 409 (Asn vs. Asp, respectively). Thus, these sequences can be used to induce a Brachyury specific CD4+ T cell response.

Positions 41 to 223 of the amino acid sequence set forth as SEQ ID NO: 1 represents the T-box DNA binding domain of human Brachyury, and the T-box domain in other Brachyury sequences, including Brachyury sequences from other species, can be readily identified by comparison to these sequences. As used herein, reference to a T-box domain of a Brachyury protein can include an additional 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 consecutive amino acids of the Brachyury sequence on the N-terminal and/or the C-terminal end of the defined T-box domain (e.g., on either side of positions 41-223 of SEQ ID NO: 1). In some embodiments, the Brachyury protein comprises the T-box domain of SEQ ID NO: 1 and induces a Brachyury specific CD4+ T cell response. In some embodiment, the polypeptide includes the T-box DNA binding domain or a portion thereof.

Human Brachyury has very high homology with Brachyury from other animal species and therefore, the sequences of Brachyury from other organisms can be utilized, particularly where these sequences are identical, substantially homologous, and elicit an effective immune response against the target antigen (e.g., native Brachyury expressed by a tumor cell). For example, murine Brachyury, which was cloned by Hermann and colleagues in 1990 (Hermann et al., supra), and is approximately 85% identical to human Brachyury at the nucleotide level. Murine Brachyury is approximately 91% identical to human Brachyury at the amino acid level. With respect to Brachyury from other animals, at the amino acid level, human Brachyury is 99.5% identical to Brachyury from *Pan troglodytes,* 90.1% identical to Brachyury from *Canis lupus familiaris,* 88.5% identical to Brachyury from *Bos Taurus,* 92.2% identical to Brachyury from *Rattus norvegicus,* and 80.9% identical to Brachyury from *Gallus gallus.* Nucleic acids encoding these Brachyury proteins can be used in the poxviral vectors and methods disclosed herein. Generally, the T-box domain of these Brachyury proteins is included in the region of amino acids 1-223. These polypeptides can be used to induce a Brachyury specific CD4+ T cell response.

Mouse and human Brachyury differ by two amino acids (at positions 26 and 96) in the T-box region. The murine Brachyury has the amino acid sequence set forth as:

```
(SEQ ID NO: 3, 436 amino acids)
MSSPGTESAGKSLQYRVDHLLSAVESELQAGSEKGDPTERELRVGLE

ESELWLRFKELTNEMIVTKNGRRMFPVLKVNVSGLDPNAMYSFLLDF

VTADNHRWKYVNGEWVPGGKPEPQAPSCVYIHPDSPNFGAHWMKAPV

SFSKVKLTNKLNGGGQIMLNSLHKYEPRIHIVRVGGPQRMITSHCFP

ETQFIAVTAYQNEEITALKIKYNPFAKAFLDAKERNDHKDVMEEPGD
```

CQQPGYSQWGWLVPGAGTLCPPASSHPQFGGSLSLPSTHGCERYPAL

RNHRSSPYPSPYAHRNSSPTYADNSSACLSMLQSHDNWSSLGVPGHT

SMLPVSHNASPPTGSSQYPSLWSVSNGTITPGSQTAGVSNGLGAQFF

RGSPAHYTPLTHTVSAATSSSSGSPMYEGAATVTDISDSQYDTAQSL

LIASWTPVSPPSM

A nucleotide sequence encoding murine Brachyury is:

(SEQ ID NO: 4)
```
ggctccgcag agtgacccct tttcttggaa aagcggtggc gagagaagtg aaggtggctg ttgggtaggg agtcaagact cctggaaggt ggagagggtg gcgggaggat gagctcgccg ggcacagaga gcgcagggaa gagcctgcag taccgagtgg accacctgct cagcgccgtg gagagcgagc tgcaggcggg cagcgagaag ggagacccca ccgaacgcga actgcgagtg ggcctggagg agagcgagct gtggctgcgc ttcaaggagc taactaacga gatgattgtg accaagaacg gcaggaggat gttcccggtg ctgaaggtaa atgtgtcagg cctggacccc aatgccatgt actctttctt gctggacttc gtgacggctg acaaccaccg ctggaaatat gtgaacgggg agtgggtacc tgggggcaaa ccagagcctc aggcgcccag ctgcgtctac atccacccag actcgcccaa ttttggggcc cactggatga aggcgcctgt gtctttcagc aaagtcaaac tcaccaacaa gctcaatgga gggggacaga tcatgttaaa ctccttgcat aagtatgaac ctcggattca catcgtgaga gttggggggcc cgcaacgcat gatcaccagc cactgctttc ccgagaccca gttcatagct gtgactgcct accagaatga ggagattaca gcccttaaaa ttaaatacaa cccatttgct aaagccttcc ttgatgccaa agaaagaaac gaccacaaag atgtaatgga ggaaccgggg gactgccagc agccggggta ttcccaatgg gggtggcttg ttcctggtgc tggcaccctc tgcccgcctg ccagctccca ccctcagttt ggaggctcgc tctctctccc ctccacacac ggctgtgaga ggtacccagc tctaaggaac caccggtcat cgccctaccc cagcccctat gctcatcgga acagctctcc aacctatgcg gacaattcat ctgcttgtct gtccatgctg cagtcccatg ataactggtc tagcctcgga gtgcctggcc acaccagcat gctgcctgtg agtcataacg ccagcccacc tactggctct agccagtatc ccagtctctg gtctgtgagc aatggtacca tcacccaggg ctcccagaca gctggggtgt ccaacggct gggagctcag ttcttcgag gctcccctgc acattacaca ccactgacgc acacggtctc agctgccacg tcctcgtctt ctggttctcc gatgtatgaa ggggctgcta cagtcacaga catttctgac agccagtatg acacggccca aagcctcctc atagcctcgt ggacacctgt gtcaccccca tctatgtgaa ttgaactttc ctccatgtgc tgagacttgt aacaaccggt gtcaactgga tcttctaggc tcaaagtggc aggctcttgg gacaagggaa aaataaataa ataaaagcta gatactaaca actccatttt caaataagag caataataca tgtcctataa tcatgttcta cagcctcttg tttgatacct acagtagtga tatgtgtcct acattatgaa gccaaggaca gagagacggc tgtggtccag ttttttgtga ctggcagtta atcagagtcc tttgctaggt agggtcctat atcttgtgtt tctctacaac atatatgtga cttttgaaatc ctggaattcg tccaccccct gtcctacttt agtgagacac aaggtacacc tctaatgtcc tcccttgttg ccttagagta gttaactttg aggacagaaa aaagcatagc cagaagattg taactgaacc gtcaactgtt ctgcccttgg aacatgccta ctttaagcac acgtagcttt ttgtgttggg aagtcaactg tatggatact tttctgttga caaagtagcc aaagacaatc tgcagaaagt gttttctgca caataaaggc aatatatagc acctgg,
```
See also the amino acid and nucleic acid sequences set forth in GENBANK ® Accession No. NM_009309 (GI: 118130357), Oct. 29, 2011, incorporated herein by reference.

Positions 41 to 223 of SEQ ID NO:4 represent the T-box DNA binding domain of murine Brachyury. These Brachyury proteins can also be used to induce a Brachyury specific T cell response.

In one embodiment, the Brachyury protein includes, consists essentially of, or consists of, an amino acid sequence at least at least 90% identical to SEQ ID NO: 1, for example a polypeptide that is about 91%, 92%, 93%, 94%, 95%, 96%, 97%, 98% or 99% identical to SEQ ID NO: 1. In another embodiment, the Brachyury proteins do not include the first amino acid of SEQ ID NO: 1 (methionine). IN further embodiments, the Brachyury protein includes, or consists of, amino acids 2-435 of SEQ ID NO: 1. In yet another embodiment, the Brachyury protein includes, or consists of, the amino acid sequence set forth as SEQ ID NO:1, with substitutions at position 177 (Asp vs. Gly, respectively), position 368 (Thr vs. Ser, respectively) and position 409 (Asn vs. Asp, respectively).

In some examples, the Brachyury protein includes amino acids 1-15 of SEQ ID NO: 1. In yet another embodiment, the Brachyury protein includes, consists essentially of, or consists of, the amino acid sequence set forth as SEQ ID NO: 3.

Brachyury polypeptides are also of use in the methods disclosed herein. The These Brachyury polypeptides include at least 15, at least 20, at least 30, at least 40, at least 50, at least 60, at least 70, at least 80, at least 90, at least 100, at least 200, or at least 300, or at least 400 amino acids of a Brachyury protein, such as 435 amino acids of a Brachyury protein. The Brachyury protein can include 15, 20, 30, 40, 50, 60, 70, 80, 90, 100, 200, 300 or 400 amino acids of a Brachyury protein. In some embodiments, a Brachyury polypeptide is 15-400, 20-400, 30-400, 40-400, 50-400, 60-400, 70-400, 80-400, 90-400, 100-400, or 200-400 amino acids of a Brachyury protein. In other embodiments, a Brachyury polypeptide is 15-300, 20-300, 30-300, 40-300, 50-300, 60-300, 70-300, 80-300, 90-300, 100-300, or 200-300 amino acids of a Brachyury protein. In additional embodiments, the Brachyury polypeptide is 15 to 10-, 20-100, 25-100, 30-100, 35-100, 40-100, 45-100, 50-100, 55-100, 60-100, 65-100, 70-100, 75-100, 80-100, 85-100, 90-100 or 95-100 amino acids of any of the Brachyury proteins disclosed herein. The Brachyury polypeptide can be 15, 50, 100, 150, 250, 300, 350, 400, 430, 431, 432, 433 or 434 amino acids in length. The Brachyury polypeptide can be 15-430, 15-431, 15-432, 15-433, 15-434 or 15-435 amino acids in length. An exemplary polypeptide is shown in FIG. 2.

In further embodiments, a Brachyury polypeptide is 15-20 amino acids in length, such as 15-17 amino acids in length, such as 15, 16, 17, 17, 19 or 20 amino acids in length and binds MHC Class II. The MHC Class II antigen can be encoded by a HLA-DP, HLA-DR, HLA-B, HLA-DQA1 or HLA-DQB1 allele.

It is disclosed herein that Brachyury protein, Brachyury polypeptides, nucleic acids encoding Brachyury proteins and polypeptides, and non-pox non-yeast viral vectors including a polynucleotide encoding a Brachyury protein can be used to induce Brachyury specific CD4+ T cells in a subject. In additional embodiments the Brachyury protein, Brachyury polypeptide, polynucleotide encoding a Brachyury protein or polypeptide, or non-pox non-yeast vector include the polynucleotide induce a Brachyury specific CD8+ T cell response, or both a Brachyury specific CD4+ T cell response and a CD8+ T cell response.

In several embodiments, the isolated Brachyury protein or polypeptide is included in a fusion protein. Thus, the fusion protein can include the Brachyury protein or Brachyury polypeptide (see above) and a second heterologous moiety, such as a myc protein, an enzyme or a carrier (such as a hepatitis carrier protein or bovine serum albumin) covalently linked to the Brachyury protein or polypeptide. Thus, in several specific non-limiting examples, the fusion protein includes a Brachyury protein (or Brachyury polypeptide) and six sequential histidine residues, a β-galactosidase amino acid sequence, and/or an immunoglobulin amino acid sequence.

Brachyury proteins or polypeptides that are linked to a carrier are also of use in the disclosed methods. Generally, a carrier is an immunogenic macromolecule to which an antigenic molecule can be bound. When bound to a carrier, the bound Brachyury protein or Brachyury polypeptide becomes more immunogenic. Carriers are chosen to increase the immunogenicity of the bound molecule and/or to elicit higher titers of antibodies against the carrier which are diagnostically, analytically, and/or therapeutically beneficial. Covalent linking of a molecule to a carrier can confer enhanced immunogenicity and T cell dependence (see Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached. Bacterial products and viral proteins (such as hepatitis B surface antigen and core antigen) can also be used as carriers, as well as proteins from higher organisms such as keyhole limpet hemocyanin, horseshoe crab hemocyanin, edestin, mammalian serum albumins, and mammalian immunoglobulins. Suitable carriers include, but are not limited to, a hepatitis B small envelope protein HBsAg. This protein has the capacity to self-assemble into aggregates and can form viral-like particles. The preparation of HBsAg is well documented, see for example European Patent Application Publication No. EP-A-0 226 846, European Patent Application Publication No. EP-A-0 299 108 and PCT Publication No. WO 01/117554, and the amino acid sequence disclosed, for example, in Tiollais et al., Nature, 317: 489, 1985, and European Patent Publication No. EP-A-0 278 940, and PCT Publication No. WO 91/14703, all of which are incorporated herein by reference.

In other embodiments, only the Brachyury protein or polypeptide is utilized. Thus, a second heterologous moiety is non-covalently linked to the Brachyury protein or polypeptide.

Nucleic Acids Encoding Brachyury Protein and Polypeptides

Nucleic acids that encode a Brachyury protein and/or polypeptide can readily be produced. These nucleic acids include DNA, cDNA and RNA sequences which encode the Brachyury polypeptide of interest. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Stryer, 1988, Biochemistry, 3.sup.rd Edition, W.H. 5 Freeman and Co., NY).

A nucleic acid encoding a Brachyury protein can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the Brachyury protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, N Y, 1989). Polynucleotides also can be isolated by screening genomic or cDNA libraries with probes selected from the sequences of the desired polynucleotide under stringent hybridization conditions.

A polynucleotide sequence encoding a Brachyury protein or polypeptide can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. Suitable promoters include, but are not limited to, an SV40 early promoter, RSV promoter, adenovirus major late promoter, human CMV immediate early I promoter, poxvirus promoter, 30K promoter, I3 promoter, sE/L promoter, 7.5K promoter, 40K promoter, and C1 promoter. T DNA vaccines are described in U.S. Pat. Nos. 5,589,466; 5,973,972, which are each incorporated herein by reference. In addition to the delivery protocols described in those applications, alternative methods of delivering DNA are described in U.S. Pat. Nos. 4,945,050 and 5,036,006, which are both incorporated herein by reference.

Plasmids have been designed with a number of goals in mind, such as achieving regulated high copy number and avoiding potential causes of plasmid instability in bacteria, and providing means for plasmid selection that are compatible with human therapeutic use. Particular attention has been paid to the dual requirements of gene therapy plasmids. First, they are suitable for maintenance and fermentation in *E. coli*, so that large amounts of DNA can be produced and purified. Second, they are safe and suitable for use in human patients and animals. The first requirement calls for high copy number plasmids that can be selected for and stably maintained relatively easily during bacterial fermentation. The second requirement calls for attention to elements such as selectable markers and other coding sequences. In some embodiments plasmids that encode a Brachyury protein or polypeptide are composed of: (1) a high copy number replication origin, (2) a selectable marker, such as, but not limited to, the neo gene for antibiotic selection with kanamycin, (3) transcription termination sequences, and (4) a multicloning site for incorporation of various nucleic acid cassettes; and (5) a nucleic acid sequence encoding a Brachyury protein and/or a Brachyury polypeptide.

There are numerous plasmid vectors that are known in the art for inducing a nucleic acid encoding a protein. These include, but are not limited to, the vectors disclosed in U.S. Pat. Nos. 6,103,470; 7,598,364; 7,989,425; and 6,416,998, which are incorporated herein by reference.

Non-Pox Non-Yeast Vectors

Non-poxviral non-yeast vectors can be used to express the Brachyury proteins and/or polypeptides disclosed herein. These vectors are not poxvirus vectors, and thus are not an orthopox, suipox, avipox, or capripox virus vector. Orthopox include vaccinia, ectromelia, and raccoon pox. One example of an orthopox is vaccinia. Avipox includes fowlpox, canary pox and pigeon pox. Capripox include goatpox and sheeppox. An example of a suipox is swinepox vector. Exemplary pox viral vectors for expression as described for example, in U.S. Pat. No. 6,165,460, which is incorporated herein by reference. The vaccinia virus genome is known in the art. It is composed of a HIND F13L region, TK region, and an HA region. Recombinant vaccinia virus has been used to incorporate an exogenous gene for expression of the exogenous gene product (see, for example, Perkus et al. *Science* 229:981-984, 1985; Kaufman et al. *Inti J. Cancer* 48:900-907, 1991; Moss *Science* 252:1662, 1991). Baxby and Paoletti (*Vaccine* 10:8-9, 1992) disclose the construction and use as a vector, of the non-replicating poxvirus, including canarypox virus, fowlpox virus and other avian species. Sutter and Moss (*Proc. Nat'l. Acad. Sci U.S.A.* 89:10847-10851, 1992) and Sutter et al. (*Virology* 1994) disclose the construction and use as a vector, the non-replicating recombinant Ankara virus (MVA, modified vaccinia Ankara) in the construction and use of a vector. These vectors are not used in the present methods.

The vectors disclosed herein are also non-yeast vectors. Thus, the disclosed vectors are not used for expression in yeast such as *S. cerevisiae* or *Kluyveromyces lactis*. Thus, the disclosed vectors generally do not include all the required elements for expression in yeast. As examples, promoters are known to be of use in yeast expression systems such as the constitutive promoters plasma membrane H$^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). The promoters are not utilized in the presently disclosed vectors. In addition, many inducible promoters, such as GAL1-10 (induced by galactose), PHO5 (induced by low extracellular inorganic phosphate), and tandem heat shock HSE elements (induced by temperature elevation to 37° C.) are not used in the present vectors. Promoters that direct variable expression in response to a titratable inducer include the methionine-responsive MET3 and MET25 promoters and copper-dependent CUP1 promoters; these promoters are not utilized. In additional examples, the vectors do not include yeast nutritional markers (such as URA3, ADE3, HIS1, and others) for selection in yeast.

A number of non-pox non-yeast viral vectors can be utilized, including polyoma, SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992. Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. Nos. 5,091,309 and 5,2217,879), alphaviruses (S. Schlesinger, 1993, Trends Biotechnol. 11:18-22; I. Frolov et al., 1996, *Proc. Natl. Acad. Sci. USA* 93:11371-11377), human herpesvirus vectors (HHV) such as HHV-6 and HHV-7, and retroviruses of avian (Brandyopadhyay et al., 1984, Mol. Cell Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell Biol., 5:431-437; Sorge et al., 1984, Mol. Cell Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (*Autographa californica* multinuclear polyhedrosis virus; AcMNPV) vectors can be used. Vectors can be obtained from commercial sources (such as PharMingen, San Diego, Calif.; Protein Sciences Corp., Meriden, Conn.; Stratagene, La Jolla, Calif.). Suitable vectors are disclosed, for example, in U.S. Published Patent Application No. 2010/0247486, which is incorporated herein by reference. In specific non-limiting examples, the vectors are retrovirus vectors (for example, lentivirus vectors), measles virus vectors, alphavirus vectors, baculovirus vectors, Sindbis virus vectors, adenovirus and poliovirus vectors. These vectors include a polynucleotide that encodes a Brachyury protein or Brachyury polypeptide.

Non-pox non-yeast vectors that encode a Brachyury protein or Brachyury polypeptide include at least one expression control element operationally linked to the nucleic acid sequence encoding the Brachyury protein or polypeptide. The expression control elements are inserted in the vector to control and regulate the expression of the nucleic acid sequence. Examples of expression control elements of use in these vectors includes, but is not limited to, lac system, operator and promoter regions of phage lambda, promoters derived from polyoma, adenovirus, retrovirus or SV40. Additional operational elements include, but are not limited to, leader sequence, termination codons, polyadenylation signals and any other sequences necessary for the appropriate transcription and subsequent translation of the nucleic acid sequence encoding the Brachyury protein or the Brachyury polypeptide in the host system. The expression vector can contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors can be constructed using conventional methods (Ausubel et al., (1987) in "Current Protocols in Molecular Biology," John Wiley and Sons, New York, N.Y.) and are commercially available.

Optionally, the vector can encode one or more immunostimulatory molecules, such as IL-2, IL-6, IL-12, LFA (for example, LFA-1, LFA-2 and/or LFA-3), CD72, RANTES, G-CSF, GM-CSF, TNF-α, IFN-γ, ICAM-1, B7-1, B7-2, other B7 related molecules, OX-40L or 41 BBL, or combinations of these molecules. These immunostimulatory molecules can be used as biological adjuvants (see, for example, Salgaller et al., 1998, J. Surg. Oncol. 68(2):122-38; Lotze et al., 2000, Cancer J Sci. Am. 6(Suppl 1):S61-6, Cao et al., 1998, Stem Cells 16(Suppl 1):251-60; Kuiper et al., 2000, Adv. Exp. Med. Biol. 465:381-90). In several examples, the vector can encode IL-2, RANTES, GM-CSF, TNF-α, IFN-γ, G-CSF, LFA-3, CD72, B7-1, B7-2, B7-1, B7-2, OX-40L, 41 BBL and/or ICAM-1.

Basic techniques for preparing recombinant DNA viruses containing a heterologous DNA sequence encoding a Brachyury protein or Brachyury polypeptide are known in the art. Such techniques involve, for example, homologous recombination between the DNA sequences flanking the DNA sequence in a donor plasmid and homologous sequences present in a parental virus (Mackett et al., 1982, Proc. Natl. Acad. Sci. USA 79:7415-7419). In particular, recombinant viral vectors can be used in delivering the gene. The vector can be constructed, for example, by steps known in the art, including using a unique restriction endonuclease site that is naturally present or artificially inserted in the parental viral vector to insert the heterologous DNA encoding the Brachyury protein or Brachyury polypeptide.

Generally, a DNA donor vector contains the following elements: (i) a prokaryotic origin of replication, so that the vector may be amplified in a prokaryotic host; (ii) a gene encoding a marker which allows selection of prokaryotic host cells that contain the vector (e.g., a gene encoding antibiotic resistance); (iii) at least one DNA sequence encoding the Brachyury protein or Brachyury polypeptide located adjacent to a transcriptional promoter capable of directing the expression of the sequence; and (iv) DNA sequences homologous to the region of the parent virus genome where the foreign gene(s) will be inserted, flanking the construct of element (iii). Methods for constructing donor plasmids for the introduction of multiple foreign genes into viral virus are described in PCT Publication no WO 91/19803, incorporated herein by reference.

Generally, DNA fragments for construction of the donor vector, including fragments containing transcriptional promoters and fragments containing sequences homologous to the region of the parent virus genome into which foreign DNA sequences are to be inserted, can be obtained from genomic DNA or cloned DNA fragments. The donor plasmids can be mono, di-, or multivalent (i.e., can contain one or more inserted foreign DNA sequences). The donor vector can contain an additional gene that encodes a marker that will allow identification of recombinant viruses containing inserted foreign DNA. Several types of marker genes can be used to permit the identification and isolation of recombinant viruses. These include genes that encode antibiotic or chemical resistance (e.g., see Spyropoulos et al., 1988, J. Virol. 62:1046; Falkner and Moss, 1988, J. Virol. 62:1849; Franke et al., 1985, Mol. Cell. Biol. 5:1918), as well as genes such as the E. coli lacZ gene, that permit identification of recombinant viral plaques by colorimetric assay (Panicali et al., 1986, Gene 47:193-199).

The DNA gene sequence to be inserted into the virus can be placed into a donor plasmid into which DNA homologous to a section of DNA such as that of the insertion site of the virus where the DNA is to be inserted has been inserted. Separately the DNA gene sequence to be inserted is ligated to a promoter. The promoter-gene linkage is positioned in the plasmid construct so that the promoter-gene linkage is flanked on both ends by DNA homologous to a DNA sequence flanking a region of viral DNA that is the desired insertion region. With a parental adenoviral vector, an adenoviral promoter is used. Similarly, with a parental lentiviral vector, a lentivirus promoter is used. The resulting plasmid construct is then amplified by growth within *E. coli* bacteria and isolated. Next, the isolated plasmid containing the DNA gene sequence to be inserted is transfected into a cell culture, along with the parental virus. Recombination between homologous viral DNA in the plasmid and the viral genome respectively results in a recombinant virus modified by the presence of the promoter-gene construct in its genome, at a site that does not affect virus viability.

As noted above, the DNA sequence is inserted into a region (insertion region) in the virus that does not affect virus viability of the resultant recombinant virus. One of skill in the art can readily identify such regions in a virus by, for example, randomly testing segments of virus DNA for regions that allow recombinant formation without seriously affecting virus viability of the recombinant.

Homologous recombination between donor plasmid DNA and viral DNA in an infected cell can result in the formation of recombinant viruses that incorporate the desired elements. Appropriate host cells for in vivo recombination are generally eukaryotic cells that can be infected by the virus and transfected by the plasmid vector. Examples of such cells suitable for use with viral vectors are fibroblasts, HuTK143 (human) cells, and CV-1 and BSC-40 (both monkey kidney) cells. Infection of cells with a virus and transfection of these cells with plasmid vectors is accomplished by techniques standard in the art (see U.S. Pat. No. 4,603,112 and PCT Publication No. WO 89/03429). Following in vivo recombination, recombinant viral progeny can be identified. For example, co-integration of a gene encoding a marker or indicator gene with the foreign gene(s) of interest, as described above, can be used to identify recombinant progeny. One specific non-limiting example of an indicator gene is the *E. coli* lacZ gene. Recombinant viruses expressing beta-galactosidase can be selected using a chromogenic substrate for the enzyme (Panicali et al., 1986, Gene 47:193). Once a recombinant virus has been identified, a variety of well-known methods can be used to assay the expression of the Brachyury protein or Brachyury polypeptide encoded by the inserted DNA fragment. These methods include black plaque assay (an in situ enzyme immunoassay performed on viral plaques), Western blot analysis, radioimmunoprecipitation (RIPA), and enzyme immunoassay (EIA).

This disclosure encompasses a recombinant vector comprising more than one antigen of interest for the purpose of having a multivalent vaccine. For example, the recombinant vectors, such as a viral vector, can comprise the virus genome or portions thereof, the nucleic acid sequence encoding the Brachyury protein or Brachyury polypeptide and a nucleic acid sequence encoding a carrier, such as, but not limited to, hepatitis B surface antigen.

The vectors of use in the methods disclosed herein are non-yeast, non-poxviral vectors. Vectors that are useful include adenovirus, alphavirus, lentivirus, measles virus and poliovirus vectors. However, this disclosure is not limited to these types of non-yeast non-poxviral vectors. Additional vectors herpes simplex viruses, human papilloma virus, Simian immunodeficiency viruses, human T cell lymphoma virus (HTLV), human foamy virus, spumaviruses, mammalian type B retroviruses, mammalian type C retroviruses, avian type C retroviruses, mammalian type D retroviruses. Vectors also include Epstein-Barr virus vectors, Moloney murine leukemia virus vectors, Harvey murine sarcoma virus vectors, murine mammary tumor virus vectors, Rous sarcoma virus vectors and nonviral plasmid vectors. Several types of vectors of use are disclosed below. Compositions including these vectors are of use in inducing a CD4+ T cell response to Brachyury and for the treatment of cancer. These compositions also can be used to induce a CD8+ T cell response to Brachyury.

Adenovirus Vectors

Adenovirus vectors (Ad) vectors can be produced that encode a Brachyury protein or a Brachyury polypeptide and are of use in the methods disclosed herein. These vectors are of use in the methods disclosed herein, including replication competent, replication deficient, gutless forms thereof, and adeno-associated virus (AAV) vectors. Without being bound by theory, adenovirus vectors are known to exhibit strong expression in vitro, excellent titer, and the ability to transduce dividing and non-dividing cells in vivo (Hitt et al., Adv in Virus Res 55:479-505, 2000). When used in vivo these vectors lead to strong but transient gene expression due to immune responses elicited to the vector backbone.

Adenoviral vectors are often constructed by insertion of a nucleic acid encoding a Brachyury protein in place of, or in the middle of, essential viral sequences such as those found at the E1 region of adenovirus (Berkner, BioTechniques, 6:616-629, 1988; Graham et al., Methods in Molecular Biology, 7:109-128, Ed: Murcy, The Human Press Inc., 1991). Inactivation of essential viral genes by, for example, deletion or insertion, disables the adenovirus' ability to replicate. To propagate such vectors in cell culture, the deleted genes must be provided in trans (for example, the E1A and E1B proteins in the case of an E1 delete vector). These replication-defective adenoviruses are produced in packaging cells engineered to complement the replication-incompetent virus by expressing the subset of genetic elements deleted from their viral genome. Potential sites for the insertion of a nucleic acid of interest, such as a nucleic acid encoding a Brachyury protein, in recombinant adenoviral vectors include, without limitation, the E1, E2, E3 and the E4 region. In some embodiments, a recombinant adenoviral vector is produced from a human adenovirus that has the E1 region deleted and replaced with a nucleic acid encoding a Brachyury protein or Brachyury polypeptide. The resulting viral vector, with one or more of its essential genes inactivated, is replication defective (Statford-Perricaudet et al., Human Gene Therapy, 1:241-256, 1990).

The recombinant adenovirus vectors can include: (1) a packaging site enabling the vector to be incorporated into replication-defective Ad virions; and (2) the nucleic acid encoding the Brachyury protein or Brachyury polypeptide. Other elements of use for incorporation into infectious virions, include the 5' and 3' Ad ITRs; the E2 and E3 genes can be included in the vector. In some embodiments, a nucleic acid encoding a Brachyury protein or Brachyury polypeptide is inserted into adenovirus in the deleted E1A, E1B or E3 region of the virus genome. In some embodiments, the adenovirus vectors do not express one or more wild-type adenovirus gene products, such as E1a, E1b, E2, E3, E4. In some non-limiting examples, virions are typically used together with packaging cell lines that complement the functions of E1, E2A, E4 and optionally the E3 gene regions (see, for example, U.S. Pat. Nos. 5,872,005, 5,994,106, 6,133,028 and 6,127,175, incorporated by reference herein in their entirety). Adenovirus vectors can be purified and formulated using techniques known in the art.

In some embodiments, packaging cell lines such as the human embryonic kidney 293 ("HEK-293" or "293") cell line (Graham et al., J. Gen. Virol., 36:59-72, 1977) or human embryonic retinoblast ("HER-911" or "911") cell line (Fallaux et al., Hum. Gene Ther., 7:215-222, 1996), provide in trans the missing region, such as the E1 region, so that the deleted or modified adenoviral vector can replicate in such cells. Suitable adenoviral vectors are disclosed, for example, in U.S. Patent Publication No. 20080193484, which is incorporated herein by reference. Replication-defective adenovirus virions encapsulating the recombinant adenovirus vectors can be made by standard techniques known in the art using packaging cells and packaging technology. Examples of these methods can be found, for example, in U.S. Pat. No. 5,872,005, incorporated herein by reference in its entirety.

Recombinant AAV vectors are characterized in that they are capable of directing the expression and the production of the selected transgenic products in targeted cells. Thus, the recombinant vectors comprise at least all of the sequences of AAV essential for encapsidation and the physical structures for infection of target cells.

Recombinant AAV (rAAV) virions can be constructed such that they include, as operatively linked components in the direction of transcription, control sequences including transcriptional initiation and termination sequences, and the nucleic acid encoding the Brachyury protein or Brachyury polypeptide. These components are bounded on the 5' and 3' end by functional AAV inverted terminal repeat (ITR) sequences. By "functional AAV ITR sequences" is meant that the ITR sequences function as intended for the rescue, replication and packaging of the AAV virion. Hence, AAV ITRs for use in the vectors need not have a wild-type nucleotide sequence, and can be altered by the insertion, deletion or substitution of nucleotides, or the AAV ITRs can be derived from any of several AAV serotypes, provided they are functional. An AAV vector is a vector derived from an adeno-associated virus serotype, including without limitation, AAV-1, AAV-2, AAV-3, AAV-4, AAV-5, AAV-6, AAV-7, AAV-8, etc. In some embodiments, the AAV vectors have the wild type REP and CAP genes deleted in whole or part, but retain functional flanking ITR sequences. These vectors can all be used, without limitation, for the expression of a Brachyury protein.

Alphavirus

Alphaviruses encoding a Brachyury protein or Brachyury polypeptide are provided and are of use in the methods disclosed herein. Alphaviruses are a set of serologically related arthropod-borne viruses of the Togavirus family. Twenty-six known viruses and virus subtypes have been classified within the alphavirus genus utilizing the hemagglutination inhibition (HI) assay. Briefly, the HI test segregates the 26 alphaviruses into three major complexes: the Venezuelan encephalitis (VE) complex, the Semliki Forest (SF) complex, and the western encephalitis (WE) complex. In addition, four additional viruses, eastern encephalitis (EE), Barmah Forest, Middelburg, and Ndumu, receive individual classification based on the HI serological assay. Representative examples of suitable alphaviruses include Aura (American Type Culture Collection (ATCC) VR-368), Bebaru virus (ATCC VR-600, ATCC VR-1240), Cabassou (ATCC VR-922), Chikungunya virus (ATCC VR-64, ATCC VR-1241), Eastern equine encephalomyelitis virus (ATCC VR-65, ATCC VR-1242), Fort Morgan (ATCC VR-924), Getah virus (ATCC VR-369, ATCC VR-1243), Kyzylagach (ATCC VR-927), Mayaro (ATCC VR-66), Mayaro virus (ATCC VR-1277), Middleburg (ATCC VR-370), Mucambo virus (ATCC VR-580, ATCC VR-1244), Ndumu (ATCC VR-371), Pixuna virus (ATCC VR-372, ATCC VR-1245), Ross River virus (ATCC VR-373, ATCC VR-1246), Semliki Forest (ATCC VR-67, ATCC VR-1247), Sindbis virus (ATCC VR-68, ATCC VR-1248), Tonate (ATCC VR-925), Triniti (ATCC VR-469), Una (ATCC VR-374), Venezuelan equine encephalomyelitis (ATCC VR-69), Venezuelan equine encephalomyelitis virus (ATCC VR-923, ATCC VR-1250 ATCC VR-1249, ATCC VR-532), Western equine encephalomyelitis (ATCC VR-70, ATCC VR-1251, ATCC VR-622, ATCC VR-1252), Whataroa (ATCC VR-926), and Y-62-33 (ATCC VR-375), see U.S. Pat. No. 5,843,723, which is incorporated herein by reference.

In some embodiments, and alphavirus vector is a Sinbis virus. In some embodiments, recombinant alphavirus vector constructs are utilized that include a 5' sequence which is capable of initiating transcription of an alphavirus, a nucleotide sequence encoding alphavirus nonstructural proteins, a viral junction region which has been inactivated such that viral transcription of the subgenomic fragment is prevented, an alphavirus RNA polymerase recognition sequence, and a nucleic acid sequence encoding a Brachyury protein. Alphavirus vector constructs which have inactivated viral junction regions do not transcribe the subgenomic fragment, making them suitable for a wide variety of applications.

In some embodiments, the alphavirus such as Sinbis virus, constructs are provided which contain a 5' promoter which is capable of initiating the synthesis of viral RNA in vitro from cDNA. The 5' promoters include both eukaryotic and prokaryotic promoters, such as, for example, the β-galactosidase promoter, trpE promoter, lacZ promoter, T7 promoter, T3 promoter, SP6 promoter, SV40 promoter, CMV promoter, and MoMLV LTR. Representative examples of such sequences include nucleotides 1-60, and to a lesser extent nucleotides 150-210, of the wild-type Sindbis virus, nucleotides 10-75 for tRNA Asparagine (Schlesinger et al., U.S. Pat. No. 5,091,309, incorporated herein by reference), and 5' sequences from other Togaviruses which initiate transcription.

Alphavirus vectors can contain sequences which encode alphavirus nonstructural proteins (NSPs). As an example, for Sindbis virus there are four nonstructural proteins, NSP1, NSP2, NSP3 and NSP4, which encode proteins that enable the virus to self-replicate. Nonstructural proteins 1 through 3 (NSP1-NSP3) are, encoded by nucleotides 60 to 5750 of the wild-type Sindbis virus. These proteins are produced as a polyprotein and later cleaved into nonstructural proteins NSP1, NSP2, and NSP3. NSP4. The alphavirus vector constructs can also include a viral junction region which has been inactivated, such that viral transcription of the subgenomic fragment is prevented. Briefly, the alphavirus viral junction region normally controls transcription initiation of the subgenomic mRNA. In the case of the Sindbis virus, the normal viral junction region typically begins at approximately nucleotide number 7579 and continues through at least nucleotide number 7612 (and possibly beyond), see U.S. Pat. No. 5,843,723 for the complete sequence, incorporated herein by reference.

Several members of the alphavirus genus can be used as "replicon" expression vectors. Replicon vectors may be utilized in any of several formats, including DNA vector constructs, RNA replicon vectors, and recombinant replicon particles (see below). These include, for example, SIN (Xiong et al., Science 243:1188-1191, 1989; Dubensky et al., J. Virol. 70:508-519, 1996; Hariharan et al., J. Virol. 72:950-958, 1998; Polo et al., PNAS 96:4598-4603, 1999), Semliki Forest virus (Liljestrom, Bio/Technology 9:1356-1361, 1991; Berglund et al., Nat. Biotech. 16:562-565, 1998), VEE (Pushko et al. Virology 239:389-401, 1997), and chimeras of multiple alphaviruses (U.S. Pat. No. 6,376,236; PCT Publication No. WO2002099035; Perri et al., J. Virol. 77:10394-10403, 2003).

Alphavirus vector constructs are also disclosed in U.S. Pat. Nos. 5,789,245; 5,843,723; 5,814,482, and 6,015,694; PCT Publication No. WO 00/61772; and PCT Publication No. WO 02/99035. Generally, these vectors include a 5' sequence which initiates transcription of alphavirus RNA, a nucleotide sequence encoding alphavirus nonstructural proteins, a viral subgenomic junction region promoter which directs the expression of an adjacent heterologous nucleic acid sequence, an RNA polymerase recognition sequence and a polyadenylate tract.

An alphavirus can be used as a replicon (a recombinant alphavirus particle) that is a virus-like particle containing a self-replicating alphavirus vector or "replicon" nucleic acid. The replicon particle itself is generally considered to be replication incompetent or "defective," that is no progeny replicon particles will result when a host cell is infected with a replicon particle, because genes encoding one or more structural proteins necessary for packaging are deleted.

Although alphavirus vectors can be used directly for administration in vivo as RNA, or delivered as a plasmid-based cDNA (e.g., Eukaryotic Layered Vector Initiation System), often, for in vivo vaccine and therapeutic applications, the alphavirus RNA replicon vector or replicon RNA is first packaged into a virus-like particle, comprising alphavirus structural proteins (e.g., capsid protein and envelope glycoproteins). Alphavirus and replicons of use are disclosed, for example, in Published U.S. Patent Application No. 20110002958, which is incorporated herein by reference. Because of their configuration, vector replicons do not express these alphavirus structural proteins necessary for packaging into recombinant alphavirus replicon particles. Thus, to generate replicon particles, the structural proteins must be provided in trans.

Packaging can be accomplished by a variety of methods, including transient approaches such as co-transfection of in vitro transcribed replicon and defective helper RNA(s) (Liljestrom, Bio/Technology 9:1356-1361, 1991; Bredenbeek et al., I Virol. 67:6439-6446, 1993; Frolov et al., J. Virol. 71:2819-2829, 1997; Pushko et al., Virology 239:389-401, 1997; U.S. Pat. Nos. 5,789,245 and 5,842,723) or plasmid DNA-based replicon and defective helper constructs (Dubensky et al., J. Virol. 70:508-519, 1996), as well as introduction of alphavirus replicons into stable packaging cell lines (PCL) (Polo et al., PNAS 96:4598-4603, 1999; U.S. Pat. Nos. 5,789,245; 5,842,723; 6,015,694).

The trans packaging methodologies permit the modification of one or more structural protein genes (for example, to incorporate sequences of alphavirus variants such as the attenuated mutants, see U.S. Pat. Nos. 5,789,245; 5,842,723; 6,015,694), followed by the subsequent incorporation of the modified structural protein into the final replicon particles. In addition, such packaging permits the overall modification of alphavirus replicon particles by packaging of a vector construct or RNA replicon derived from a first alphavirus using structural proteins derived from a second alphavirus different from that of the vector construct.

Measles Virus

Measles viruses encoding a Brachyury protein or Brachyury polypeptide are provided and are of use in the methods disclosed herein. The nucleic acid sequences of Measles Viruses are disclosed in PCT Publication No. WO 98/13501, which provides the sequence of a DNA copy of the positive strand (antigenomic) message sense RNA of various wild-type of vaccine measles strains, including Edmonston Wild-type strain, Moraten strain and Schwarz strain. PCT Publication No. WO 97/06270, incorporated herein by reference, discloses the production of recombinant measles vectors.

An attenuated strain of measles virus can also be used to deliver a Brachyury protein or Brachyury polypeptide. The Moraten attenuated form of the virus has been used worldwide as a vaccine and has an excellent safety record (Hilleman, et al., J. Am. Med. Assoc. 206: 587-590, 1968). Accordingly, in one embodiment, the Moraten strain is used. The Moraten vaccine is commercially available from MERCK® and is provided lyophilized in a vial which when reconstituted to 0.5 ml comprises $10^3$ pfu/ml.

In a further embodiment, the Edmonston-B vaccine strain of measles virus is used (MV-Edm) (Enders and Peebles, Proc. Soc. Exp. Biol. Med. 86: 277-286, 1954). MV-Edm grows efficiently in tumor cells but its growth is severely restricted in primary cultures of human peripheral blood mononuclear cells, normal dermal fibroblasts, and vascular smooth muscle cells. A form of the Enders attenuated Edmonston strain is available commercially from Merck (ATTENUVAX®). Other attenuated measles virus strains can also be utilized, such as Leningrad-16, and Moscow-5 strains (Sinitsyna, et al., Res. Virol. 141(5): 517-31, 1990), Schwarz strain (Fourrier, et al., Pediatrie 24(1): 97-8, 1969), 9301B strain (Takeda, et al. J. VIROL. 72/11: 8690-8696), the AIK-C strain (Takehara, et al., Virus Res 26 (2): 167-75, 1992), and those described in Schneider-Shaulies, et al., PNAS 92(2): 3943-7, 1995).

In some embodiments, the recombinant measles virus nucleotide sequence comprises a replicon having a total number of nucleotides which is a multiple of six. The "rule of six" is expressed in the fact that the total number of nucleotides present in the recombinant cDNA finally amount to a total number of nucleotides which is a multiple of six, a rule which allows efficient replication of genome RNA of the measles virus.

In additional embodiments, heterologous DNA, such as a nucleic acid encoding Brachyury protein, is cloned in the measles virus within an Additional Transcription Unit (ATU) inserted in the cDNA corresponding to the antigenomic RNA of measles virus. The location of the ATU can vary along the cDNA: it is however located in such a site that it will benefit from the expression gradient of the measles virus. Therefore, the ATU can be spread along the cDNA. In one embodiment, the ATU is inserted in the N-terminal portion of the sequence and especially within the region upstream from the L-gene of the measles virus and upstream from the M gene of the virus. In other embodiments, the ATU is inserted upstream from the N gene of the virus, see U.S. Published Patent Application No. 2011/0129493, incorporated herein by reference. Particular cistrons in the measles virus genome can targeted to modify genes whose expression is associated with attenuation (Schneider-Shaulies et at. PNAS 92(2): 3943-7, 1995, Takeda, et al. J. Virol. 72/11: 8690-8696, 1998). Thus, in one embodiment, a recombinant measles virus strain is generated encoding a Brachyury protein or Brachyury polypeptide in any of an H protein, a V protein, a C protein, and combinations thereof.

Recombinant measles virus vectors include the plasmid pTM-MVSchw which contains the cDNA resulting from reverse transcription of the antigenomic RNA of measles virus and an adapted expression control sequence including a promoter and terminator for the T7 polymerase. Vectors are also disclosed, for example, in U.S. Published Patent Application No. 2006/0013826, which is incorporated herein by reference. These vectors are of use in the methods disclosed herein.

Additional attenuated strains of measles virus can be produced that express a Brachyury protein or Brachyury polypeptide. Attenuated strains of viruses are obtained by serial passage of the virus in cell culture (e.g., in non-human cells), until a virus is identified which is immunogenic but not pathogenic. While wild type virus will cause fatal infection in marmosets, vaccine strains do not. Individuals receiving an attenuated measles virus vaccine do not display classical measles symptoms. Attenuation is associated with decreased viral replication (as measured in vivo by inability to cause measles in monkeys), diminished viremia, and failure to induce cytopathological effects in tissues (e.g., cell-cell fusion, multinucleated cells). See U.S. Pat. No. 7,393,527, which is incorporated herein by reference.

In one embodiment, an effective dose of an attenuated measles virus encoding a Brachyury protein or Brachyury polypeptide is produced by infecting a primary cell or a continuous cell line with a starting innoculum of a stock comprising an attenuated Moraten strain of measles virus (or an innoculum of an MMR stock) or the MV-Edm strain or any of the other strains described above and expanding the virus after serial passage. Cells or cell lines include, but are not limited to, monkey kidney or testes cells or monkey cell lines (e.g., Vero, KB, CV-1, BSC-1, and the like). Viral replication in cells is observed as cell-cell fusion and syncytia formation.

The attenuated measles virus is expanded until a desired dose concentration is obtained in standard cell culture media. In one embodiment, the therapeutically effective dose concentration is about $10^3$ to $10^{12}$ pfu. In another embodiment of the invention, the concentration is about $10^5$ to $10^8$ pfu. Viral titer can be assayed by inoculating cells (e.g., Vero cells) in culture dishes (e.g., such as 35 mm dishes). After 2-3 hours of viral adsorption, the inoculum is removed and cells are overlaid with a mixture of cell culture medium and agarose or methylcellulose (e.g., 2 ml DMEM containing 5% FCS and 1% SeaPlaque agarose). After about 3 to about 5 days, cultures are fixed with 1 ml of 10% trifluoroacetic acid for about 1 hour, then UV cross-linked for 30 minutes. After removal of the agarose overlay, cell monolayers are stained with crystal violet and plaques are counted to determine viral titer. Virus is harvested from cell syncytia by scraping cells from the dishes, subjecting them to freeze/thawing (e.g., approximately two rounds), and centrifuging. The cleared supernatants represent "plaque purified" virus.

Viral stocks are produced by infection of cell monolayers (e.g., adsorption for about 1.5 hours at 37° C.), followed by scraping of infected cells into a suitable medium (e.g., Opti-MEM, Gibco-BRL) and freeze/thaw lysis (for example, 2 rounds). Viral stocks are aliquoted, frozen and stored at 70° C.-80° C. and can be stored at concentrations higher than the therapeutically effective dose. In one embodiment, viral stock is stored in a stabilizing solution. Stabilizing solutions are known in the art, see for example, U.S. Pat. Nos. 4,985,244, and 4,500,512.

Poliovirus

Polioviruses encoding a Brachyury protein or a Brachyury polypeptide are provided and are of use in the methods disclosed herein. The entire poliovirus genome has been cloned and sequenced and the viral proteins identified. An infectious poliovirus cDNA is also available which has allowed further genetic manipulation of the virus (Racaniello V R et al., Science 214(4542) 916-919, 1981). The wild-type genomic RNA molecule is 7433 nucleotides long, polyadenylated at the 3' end and has a small covalently attached viral protein (VPg) at the 5' terminus (Kitamura N et al., Nature 291:547-553; 1981 Racaniello V R et al., Proc. Natl. Acad. Sci. USA 78:4887-4891, 1981). Expression of the poliovirus genome occurs via the translation of a single protein (polyprotein) which is subsequently processed by virus encoded proteases (2A and 3C) to give the mature structural (capsid) and nonstructural proteins (Kitamura N et al., Nature 291:547-553, 1981; Koch F et al., The Molecular Biology of Poliovirus, Springer-Verlag, Vienna, 1985). Poliovirus replication is catalyzed by the virus-encoded RNA-dependent RNA polymerase, which copies the genomic RNA to give a complementary RNA molecule, which then serves as a template for further RNA production (Koch F et al., supra; Kuhn R J et al., in D J Rowlands et al. (ed.) Molecular Biology of Positive Strand RNA viruses, Academic Press Ltd., London, 1987). The translation and proteolytic processing of the poliovirus polyprotein is described in Nicklin M J H et al., Bio/Technology 4:33-42, 1986.

The viral RNA genome encodes the necessary proteins required for generation of new progeny RNA, as well as encapsidation of the new RNA genomes. In vitro, poliovirus is lytic, resulting in the complete destruction of permissive cells. Since the viral replication cycle does not include any DNA intermediates, there is no possibility of integration of viral DNA into the host chromosomal DNA.

Early studies identified three poliovirus types based on reactivity to antibodies (Koch F et al., supra, 1985). These three serological types, designated as type I, type II, and type III, have been further distinguished as having numerous nucleotide differences in both the non-coding regions and the protein coding regions. All three strains are suitable for use in delivering heterologous proteins. In addition, there are also available attenuated versions of all three strains of poliovirus.

Replicons can comprise deoxyribonucleic acid (DNA) or ribonucleic acid (RNA). Replicons are poliovirus-based polynucleotides that lack a wild type poliovirus nucleic acid necessary for encapsidation of the virus. Consequently, newly encapsidated replicons cannot be produced following initial cell entry in the absence of the missing nucleic acid. Replicons can lack this nucleic acid as a result of any modification of the wildtype poliovirus nucleic acid including, but not limited to, deletions, insertions, and substitutions, including an insertion of a nucleic acid encoding a Brachyury protein. In some embodiments, poliovirus replicons lack a wild type poliovirus nucleic acid that encodes at least a portion of a protein that is required for encapsidation. Proteins necessary for replicon encapsidation include proteins that are part of the capsid structure. Examples of such proteins are those encoded by the VP1, VP2, VP3, and VP4 genes of the poliovirus P1 capsid precursor region, the Vpg protein, and those proteins that are necessary for proper processing of structural proteins of the capsid structure, such as the proteases responsible for cleaving the viral polyprotein. Thus, in some embodiments, the poliovirus vector lacks nucleic acid sequences encoding one or more of VP1, VP2, VP3, and VP4, genes of the poliovirus P1 capsid precursor region, the Vpg protein, and encodes a Brachyury protein or Brachyury polypeptide.

Replicons are typically introduced into a cell in an RNA form. Encapsidated replicons are able to enter cells via interaction of the capsid proteins with poliovirus receptor. Replicons are fully capable of RNA replication (amplification) upon introduction into cells and translation, in the correct reading frame, of the single polyprotein through which expression of the entire replicon genome occurs. Translation of replicon sequences may be transient, usually lasting only about 24-48 hours. High levels of replicon-encoded proteins can accumulate during the translation period. Encapsidated replicons are able to enter cells via interaction of the capsid proteins with the hPVR protein.

In some embodiments, replicons comprise RNA, including sequences encoding Brachyury protein, and are encapsidated. In some examples, the replicons have a deletion of the capsid (P1) gene and are derived from the RNA genome of poliovirus type 1, type 2, type 3 or combinations thereof. Further, a nucleic acid encoding a Brachyury protein or Brachyury polypeptide can be substituted for part or all of the capsid (P1) gene such that the portion of the capsid (P1) gene which remains, if any, is insufficient to support encapsidation in vivo. Generally, the term "P1 replicons" refers to replicons in which the entire nucleic acid encoding the P1 capsid precursor protein has been deleted or altered such that the proteins which are normally encoded by this nucleic acid are not expressed or are expressed in a non-functional form. The proteins that are normally encoded by the P1 capsid precursor region of the poliovirus genome include the proteins encoded by the VP1, VP2, VP3, and VP4 genes. P1 replicons, therefore, lack the VP1, VP2, VP3, and VP4 genes or comprise unexpressible or non-functional forms of the VP1, VP2, VP3, and VP4 genes. P1 replicons can include a nucleic acid encoding a Brachyury protein or Brachyury polypeptide substituted for the VP1, VP2, VP3, and VP4 genes.

In some embodiments, encapsidated replicons may be produced by introducing both a replicon and a complementing expression vector that provides the missing nucleic acid necessary for encapsidation in trans to a host cell. A "replicon encapsidation vector" refers to a non-poliovirus-based vector that comprises a nucleic acid required for replicon encapsidation and provides the required nucleic acid (or encoded protein) in trans. Replicon encapsidation vectors can be introduced into a host cell prior to, concurrently with, or subsequent to replicon introduction. Suitable methods for encapsidation are disclosed in U.S. Pat. No. 6,680,169, which is incorporated by reference herein. Methods which can be used to prepare encapsidated replicons have been described Porter D C et al., J. Virol. 67:3712-3719, 1993; Porter D C et al., 1995, J. Virol. 69:1548-1555, 1995; PCT Publication No. WO 96/25173; U.S. Pat. Nos. 5,614,413, 5,817,512; 6,063,384; and 6,680,169.

Nonencapsidated replicons can be delivered directly to target cells, for example by direct injection into, for example, muscle cells (see, for example, Acsadi G et al., Nature 352(6338):815-818, 1991; Wolff J A et al., Science 247:1465-1468, 1990), or by electroporation, transfection mediated by calcium phosphate, transfection mediated by DEAE-dextran, liposome-mediated transfection or receptor-mediated nucleic acid uptake (see for example Wu G et al., J. Biol. Chem. 263:14621-14624, 1988; Wilson J M et al., J. Biol. Chem. 267:963-967, 1992; and U.S. Pat. No. 5,166,320), or other methods of delivering naked nucleic acids to target cells.

Retroviral Vectors

Retroviral vectors, including lentiviral vectors encoding a Brachyury protein and/or Brachyury polypeptide are provided and are of use in the methods disclosed herein. Retroviral vectors have been tested and found to be suitable delivery vehicles for the stable introduction of a variety of genes of interest into the genomic DNA of a broad range of target cells. Without being bound by theory, the ability of retroviral vectors to deliver unrearranged, single copy transgenes into cells makes retroviral vectors well suited for transferring genes into cells. Further, retroviruses enter host cells by the binding of retroviral envelope glycoproteins to specific cell surface receptors on the host cells. Consequently, pseudotyped retroviral vectors in which the encoded native envelope protein is replaced by a heterologous envelope protein that has a different cellular specificity than the native envelope protein (e.g., binds to a different cell-surface receptor as compared to the native envelope protein) can also be used.

Generally, retroviruses contain three major coding domains, gag, pol, env, which code for essential virion proteins. Retroviral vectors are of use wherein gag, pol and/or env are absent or not functional. Retroviral vectors are disclosed, for example, in U.S. Published Patent Application No. 20060286634, which is incorporated herein by reference herein.

Thus retroviral vectors are provided which include, for example, retroviral transfer vectors comprising a nucleic acid encoding a Brachyury protein and retroviral packaging vectors comprising one or more packaging elements. In some embodiments, pseudotyped retroviral vectors are provided encoding a heterologous or functionally modified envelope protein for producing pseudotyped retrovirus.

There are many retroviruses and examples include: murine leukemia virus (MLV), lentivirus such as human immunodeficiency virus (HIV), equine infectious anaemia virus (EIAV), mouse mammary tumor virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV). Other retroviruses suitable for use include, but are not limited to, Avian Leukosis Virus, Bovine Leukemia Virus, Mink-Cell Focus-Inducing Virus. The core sequence of the retroviral vectors can be derived from a wide variety of retroviruses, including for example, B, C, and D type retroviruses as well as spumaviruses and lentiviruses (see RNA Tumor Viruses, Second Edition, Cold Spring Harbor Laboratory, 1985). An example of a retrovirus suitable for use in the compositions and methods disclosed herein, includes, but is not limited to, lentivirus.

One lentivirus is a human immunodeficiency virus (HIV), for example, type 1 or 2 (i.e., HIV-1 or HIV-2). Other lentivirus vectors include sheep Visna/maedi virus, feline immunodeficiency virus (FIV), bovine lentivirus, simian immunodeficiency virus (SIV), an equine infectious anemia virus (EIAV), and a caprine arthritis-encephalitis virus (CAEV).

Lentiviruses share several structural virion proteins in common, including the envelope glycoproteins SU (gp120) and TM (gp41), which are encoded by the env gene; CA (p24), MA (p117) and NC (p7-11), which are encoded by the gag gene; and RT, PR and IN encoded by the pol gene. HIV-1 and HIV-2 contain accessory and other proteins involved in regulation of synthesis and processing virus RNA and other replicative functions. The accessory proteins, encoded by the vif, vpr, vpu/vpx, and nef genes, can be omitted (or inactivated) from the recombinant system. In addition, tat and rev can be omitted or inactivated, such as by mutation or deletion.

Without being bound by theory, the use of lentivirus-based gene transfer techniques generally relies on the in vitro production of recombinant lentiviral particles carrying a highly deleted viral genome in which a gene of interest, such as a nucleic acid encoding a Brachyury protein or Brachyury polypeptide, is accommodated. In particular, the recombinant lentivirus are recovered through the in trans co-expression in a permissive cell line of (1) the packaging constructs, i.e., a vector expressing the Gag-Pol precursors together with Rev (alternatively expressed in trans); (2) a vector expressing an envelope receptor, generally of an heterologous nature, and (3) the transfer vector, consisting in the viral cDNA deprived of all open reading frames, but maintaining the sequences required for replication, incapsidation, and expression, in which the sequences to be expressed are inserted. In one embodiment the lentigen lentiviral vector described in Lu, X. et al. Journal of gene medicine 6:963-973, 2004 is used to express the Brachyury protein or Brachyury polypeptide. Suitable lentiviral vectors are also disclosed, for example, in U.S. Published Patent Application No. 20100062524, which is incorporated herein by reference.

Retroviral packaging systems for generating producer cells and producer cell lines that produce retroviruses, and methods of making such packaging systems are known in the art. Generally, the retroviral packaging systems include at least two packaging vectors: a first packaging vector which includes a first nucleotide sequence comprising a gag, a pol, or gag and pol genes; and a second packaging vector which includes a second nucleotide sequence comprising a heterologous or functionally modified envelope gene. In some embodiments, the retroviral elements are derived from a lentivirus, such as HIV. These vectors can lack a functional tat gene and/or functional accessory genes (vif, vpr, vpu, vpx, nef). In other embodiments, the system further comprises a third packaging vector that comprises a nucleotide sequence comprising a rev gene. The packaging system can be provided in the form of a packaging cell that contains the first, second, and, optionally, third nucleotide sequences.

First generation lentiviral vector packaging systems provide separate packaging constructs for gag/pol and env, and typically employ a heterologous or functionally modified envelope protein for safety reasons. In second generation lentiviral vector systems, the accessory genes, vif, vpr, vpu and nef, are deleted or inactivated. Third generation lentiviral vector systems are those from which the tat gene has been deleted or otherwise inactivated (e.g., via mutation). Compensation for the regulation of transcription normally provided by tat can be provided by the use of a strong constitutive promoter, such as the human cytomegalovirus immediate early (HCMV-IE) enhancer/promoter. Other promoters/enhancers can be selected based on strength of constitutive promoter activity, specificity for target tissue (e.g., liver-specific promoter), or other factors relating to desired control over expression, as is understood in the art. For example, in some embodiments, an inducible promoter such as tet can be used to achieve controlled expression. The gene encoding rev can be provided on a separate expression construct, such that a typical third generation lentiviral vector system will involve four plasmids: one each for gagpol, rev, envelope and the transfer vector. Regardless of the generation of packaging system employed, gag and pol can be provided on a single construct or on separate constructs.

Typically, the packaging vectors are included in a packaging cell, and are introduced into the cell via transfection, transduction or infection. Methods for transfection, transduction or infection are well known by those of skill in the art. A retroviral vector of the present invention can be introduced into a packaging cell line, via transfection, transduction or infection, to generate a producer cell or cell line. The packaging vectors can be introduced into human cells or cell lines by standard methods including, for example, calcium phosphate transfection, lipofection or electroporation. In some embodiments, the packaging vectors are introduced into the cells together with a dominant selectable marker, such as neo, DHFR, Gln synthetase or ADA, followed by selection in the presence of the appropriate drug and isolation of clones. A selectable marker gene can be linked physically to genes encoding by the packaging vector.

Stable cell lines, wherein the packaging functions are configured to be expressed by a suitable packaging cell, are known. For example, see U.S. Pat. No. 5,686,279; and Ory et al., Proc. Natl. Acad. Sci. 93:11400-11406, 1996, which describe packaging cells. Zufferey et al., Nature Biotechnology 15:871-875, 1997 disclose a lentiviral packaging plasmid wherein sequences 3' of pol including the HIV-1 envelope gene are deleted. The construct contains tat and rev sequences and the 3' LTR is replaced with poly A sequences. The 5' LTR and psi sequences are replaced by another promoter, such as one which is inducible. For example, a CMV promoter can be used.

The packaging vectors can include additional changes to the packaging functions to enhance lentiviral protein expression and to enhance safety. For example, all of the HIV sequences upstream of gag can be removed. Also, sequences downstream of envelope can be removed. Moreover, steps can be taken to modify the vector to enhance the splicing and translation of the RNA.

A self-inactivating vector (SIN) can be used, which improves the biosafety of the vector by deletion of the HIV-1 long terminal repeat (LTR) as described, for example, by Zufferey et al., J. Virology 72(12):9873-9880, 1998. Inducible vectors can also be used, such as through a tet-inducible LTR.

Host Cells

DNA sequences encoding a Brachyury protein and/or Brachyury polypeptide can be expressed from a vector in vitro by DNA transfer into a suitable host cell. The term "host cell" also includes any progeny of the subject host cell. It is understood that all progeny may not be identical to the parental cell since there may be mutations that occur during replication. Methods of stable transfer, meaning that the foreign DNA is continuously maintained in the host, are known in the art.

Hosts cells can include microbial, insect and mammalian host cells. Methods of expressing DNA sequences having eukaryotic or viral sequences in prokaryotes are well known in the art. Non-limiting examples of suitable host cells include animal cells (for example, mammalian cells, such as human). Techniques for the propagation of mammalian cells in culture are well-known (see, Jakoby and Pastan (eds), 1979, Cell Culture. Methods in Enzymology, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although cell lines may be used, such as cells designed to provide higher expression desirable glycosylation patterns, or other features.

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or infection with the poxvirus vectors can be used. Eukaryotic cells can also be co-transformed with polynucleotide sequences encoding a Brachyury protein or Brachyury polypeptide, and a second foreign DNA molecule encoding a selectable phenotype, such as the herpes simplex thymidine kinase gene. Methods for using viral vectors to transform eukaryotic cells are known, (see for example, *Eukaryotic Viral Vectors*, Cold Spring Harbor Laboratory, Gluzman ed., 1982).

A nucleic acid encoding a Brachyury protein is expressed in the host cell, such as a *Salmonella* host cell, for example *S. typhimurium* host cell, or a *Listeria*, such as a *L. monocytogenes* host cell. A host cell-compatible promoter is any promoter or promoter/enhancer that is able to initiate sufficient transcription of the Brachyury protein or Brachyury polypeptide, such as in amounts sufficient to induce a Brachyury specific CD4+ T cell response when the host cell is introduced into the subject. Some examples of expression control sequences are a promoter/enhancer from the cytomegalovirus (CMV) immediate early gene 1 or the Rous sarcoma virus (RSV) long terminal repeat or the simian virus 40 promoter or the adenovirus 2 major late promoter or the mouse mammary tumor virus promoter (MMTV). These host cells can be used in attenuated and/or heat-killed forms. These host cells can be administered multiple times without eliciting host neutralizing activity.

In some embodiments the host cell are utilized with an adjuvant. Specific non-limiting examples of adjuvants of use are GM-CSF, *Bacillus*-Calmette-Guerin adjuvant or CD40 ligand (CD40L).

Attenuated Bacteria: *Listeria* and *Salmonella*

Prokaryotic host cells include *Listeria* and *Salmonella*, which can be used directly to provide a Brachyury protein and/or Brachyury polypeptide, such as for use in the methods disclosed herein. Thus, in some embodiments, an attenuated invasive intracellular bacterium capable of infecting a mammalian host or cell thereof, but having a decreased ability in intra- and intercellular movement in the host as compared to a wild type bacterium is utilized. In some embodiments, the bactium is transformed with (a) a promoter activated when said bacterium is present in the cytosol of a host cell, operably linked to a structural gene or fragment thereof, encoding a polypeptide which is lethal to the bacterium, (b) a host cell-compatible promoter, operably linked to a structural gene or fragment thereof, encoding a Brachyury protein, wherein (a) and (b) can be on the same plasmid or different plasmids or (a) can be integrated into the bacterial chromosome. The attenuated bacteria include a number of intracellular bacteria, such as *Salmonella, Yersinia, Renibacterium* and *Listeria* capable of intracellular growth (Coynault et al., Molecular Microbiology 22, 149-160, 1996; Hohmann et al., Vaccine 14, 19-14, 1996; Karem et al., Infection and Immunity 63, 4557-4563, 1995; O'Callaghan et al., Infection and Immunity 56, 419-423, 1988; Sigwart et al., Infection and Immunity 57, 1858-61, 1989; and Sinha et al., Infection and Immunity 65, 1566-1569, 1997).

The disclosed attenuated invasive bacteria can still invade a host, or cells thereof, but are not pathogenic. In some embodiments, attenuation can be achieved by mutation (see T. Maniatis, et al. Molecular Cloning: A Laboratory Manual, Second Edition, Cold Spring Harbor, N.Y., 1989). In specific non-limiting examples, attenuation can be caused by mutating the bacterial genes which encode for pathogenic and/or toxic polypeptides. Such a mutation can be achieved randomly, such as by chemical modification and selected later, for example, for loss of function, or it can be site directed. Thus in some embodiments, the bacterium is attenuated by deletion, insertion or point mutations, to eliminate the function of certain genes that encode polypeptides which lead to pathogenesis. In some embodiments, the bacterium is attenuated by deletion of an entire operon by chromosomal deletion, such as the attenuated *L. monocytogenes* mutant strain DELTA2 that is a derivative of the fully virulent wild-type strain EGD, and lacks the entire lecithinase operon consisting of the genes mpl, actA and plcB due to a chromosomal deletion. Due to the deletion of this operon the inflammatory response caused by *L. monocytogenes* during infection of a mammalian host is significantly reduced. Suitable bacteria are disclosed for example, in U.S. Pat. No. 6,143,551, which is incorporated by reference herein.

A variety of potential live *Salmonella* strains with different attenuation levels, which subsequently serve as platforms for the development of recombinant live *Salmonella* carrier strains that express heterologous antigens. Such recombinant live *Salmonella* vaccine carriers are equipped with modules comprising variable gene cassettes that regulate the expression of heterologous antigens in *Salmonella* and determine presentation of the heterologous antigens to the host immune system. By combinations of both systems, differently attenuated live *Salmonella* vaccine strains and variable gene cassettes, a variety of recombinant live carrier strains can be generated that have broad application.

*S. typhimurium* contains two type III secretion systems for virulence determinants. The first controls bacterial invasion of epithelial cells, and is encoded by genes within a 40 kb pathogenicity island (SPI1). The other is encoded by genes within a second 40 kb pathogenicity island (SPI2) and is required for systemic growth of this pathogen within its host. The genes located on pathogenicity island SPI1 are mainly responsible for early steps of the infection process, the invasion of non-phagocytic host cells by the bacterium. For most of the SPI1 genes, mutations result in a reduced invasiveness in vitro. However, mutants that are defective in invasion are not necessarily avirulent. In comparison, virulence studies of SPI2 mutants have shown them to be attenuated by at least five orders of magnitude compared with the wild-type strain after both oral and intraperitoneal inoculation of mice.

Many of the genes encoding components of the SPI2 secretion system are located in a 25 kb segment of SPI2. SPI2 contains genes for a type III secretion apparatus (ssa) and a two component regulatory system (ssr), as well as candidate genes for a set of secreted effectors (sse) and their specific chaperones (ssc). On the basis of similarities with genes present in other bacterial pathogens, the first 13 genes within the ssaK/U operon and ssaJ encode components of the secretion system apparatus. A number of additional genes, including ssaC, which encode a secretion system apparatus protein and a two component regulatory protein, respectively, are found in a region approximately 8 kb from ssaJ.

Thus, an attenuated gram-negative cell can have inactivated at least one gene selected from effector (sse) gene secretion apparatus (ssa) genes, chaperon (ssc) genes and regulation (ssr) genes. With regard to the sse genes are affected by the inactivation, the inactivated gene is preferably sseC, sseD, sseE or a combination thereof. As far as the ssr genes are affected by the inactivation, preferably at least ssrB is inactivated. As far as the ssc genes are affected by the inactivation, preferably at least sscB is inactivated.

Attenuation can be the result of original mutations in SPI2 gene locus. Combination of the individual mutations in the SPI2 gene locus with each other, and with other known attenuating gene mutations, such as aroA, results in a broad repertoire of attenuation and immunogenicity. Different expression cassettes can be introduced on these platforms, allowing further modulation of the immune response directed against the heterologous antigens.

Pathogenic *Salmonella* or *Listeria* serve as a basis for the construction of a panel of different live *Salmonella* vaccine prototypes generated by gradual attenuations accomplished through the introduction of defined SPI2 gene locus mutations. Each resulting individual live *Salmonella* vaccine prototype is further transformed into a multivalent recombinant vaccine by the introduction of exchangeable DNA modules carrying (1) a nucleic acid encoding a Brachyury protein or polypeptide and (2) adequate expression systems executing efficacious antigen presentation to the host immune system. In concert, these features elicit a specific immune response, such as a Brachyury specific T cell response.

The inactivation of the gene of the SPI2 locus (or functional homologue thereof in cells other than *Salmonella*) is effected by a mutation which may comprise deletion. In some embodiments, the deletion is cause by insertion of a heterologous nucleic acid, such as a nucleic acid encoding Brachyury into the gene to be inactivated. With regard to *Salmonella*, pathogenic *Salmonella* species are gradually attenuated by mutations in individual virulence genes that are part of the SPI2 gene locus, for example an sse gene coding for an effector protein, such as sseC, ssed or sseE, or an ssc gene, such as sscB, coding for a chaperone, or an ssr gene, such as ssrB, coding for a regulator. Individual mutation of each of these genes leads to a unique individual grade of attenuation, which, in turn, effects a characteristic immune response at the mucosal, humoral and cellular levels. The individual grade of attenuation can be moderately increased by combinations of at least two gene mutations within the SPI2 gene locus or by combination with a mutation in another Salmonella gene known to attenuate virulence, such as an aro gene, for example aroA. A stronger grade of attenuation is achieved by mutation of a virulence gene that is part of a polycistronic gene cluster encoding several virulence factors, such as the transcriptional unit comprising the sseC, sseD, sseE and sscB genes, such that the mutation exerts a polar effect, disrupting expression of the following genes. The grade of attenuation may directly depend on the number of virulence genes that are affected by the polar mutation as well as their individual characteristics. Finally, the strongest attenuation is achieved when regulatory genes, such as ssrB, are mutated. Again, each mode of attenuation of Salmonella leads to the generation of a live Salmonella strain that evokes an immune response, see U.S. Pat. No. 7,700,104, which is incorporated herein by reference.

With regard to Listeria, L. monocytogenes is a Gram-positive, facultative intracellular bacterium that lacks lipopolysaccharide (LPS) and is also able to invade a wider range of mammalian cells where it replicates in the cytosol as well (Portnoy et al., Infect. Immun. 60, 1263, 1992). Since it invades its host through the intestinal mucosal surface, L. monocytogenes is also a candidate for oral vaccination. Shortly after infection, bacteria are found in the spleen where professional APC are abundant. Delivery of DNA to those cells is therefore significantly enhanced by the use of suitably constructed L. monocytogenes. Attenuated L. monocytogenes cells are lysed in the cytosol of the host cell by the production of a $P_{actA}$-dependent phage lysin releasing plasmid DNA which carries a heterologous gene, such as a nucleic acid encoding Brachyury protein, under the control of a promoter, such as, but not limited to, the human cytomegalovirus major immediate-early promoter/enhancer region. Beside the advantages of avoiding the use of antibiotics, lysin-mediated plasmid release is an efficient method comparable to eliminating the bacteria by antibiotic treatment.

The attenuated bacterium can be a mutant of wild-type Listeria which invades host cells and is released into the cytosol of the infected cells with similar efficiencies as the wild-type strain, but is impaired in intra- and intercellular movement. For example, the mutant L. monocytogenes strain DELTA2 is unable to polymerise host cell actin in the cytosol which L. monocytogenes wild type strain uses for its movement inside the host cell. Furthermore, due to the deletion of plcB, the bacterium is unable to lyse the host cell membranes which the wild type strain lyses upon entering neighboring cells. Mutant bacteria are therefore unable to move from one infected cell into a neighboring cell (cell-to-cell spread). This illustrates a decreased ability as compared to wild type strains in intra- and inter-cellular movement. In some embodiments the attenuated bacterium is a mutant of L. monocytogenes which invades the host and is released into the cytosol of the infected cells with similar efficiencies as the wild-type strain, but it is not pathogenic, i.e., it doesn't cause a disease. In specific non-limiting examples, the bacterium is L. monocytogenes that lacks the entire lecithinase operon containing the genes mpl, actA and plcB, and encodes a Brachyury protein or a Brachyury polypeptide.

In some embodiments, a structural gene or fragment thereof is also included, such as encoding a polypeptide which is lethal to the bacterium is any polypeptide which when expressed in the bacterium will result in the release of plasmid DNA and death of the bacterium, for example by lysis of the bacterium. In some embodiments, the polypeptide can be a bacteriophage lysin, preferable the gene product of ply 118 or other Listeria-phage-encoded lysins, for example the mureinhydrolase encoded by the iap gene of L. monocytogenes or other iap-related genes especially iap of L. grayi. The lysis protein PLY 118 is a late gene product of the Listeria bacteriophage A118 necessary for the release of progeny phages. PLY 118 is a highly active, cell wall-hydrolyzing enzyme specific for Listeria (Loessner et al., Mol. Microbiol. 16, 1231, 1995). By a promoter activated when it is present in an invasive bacterium which is in the cytosol of a host cell, it is meant any promoter which, when the bacteria is inside the infected cell, is (under the control of a transcription activator which is) preferentially turned on, driving its transcription. For example, the L. monocytogenes promoter $P_{actA}$ can be used. The $P_{actA}$ promoter is controlled by the transcription activator PrfA which regulates most of the known virulence genes of L. monocytogenes and is specifically activated in the cytosol of the infected host cells to interact with the actA promoter. Other promoters which can be used are other promoters of L. monocytogenes, such as those controlling the expression of inlC and other genes for small internalins (Engelbrecht et al., Mol. Microbiol. 21:823-837, 1996).

Therapeutic Methods and Pharmaceutical Compositions

The Brachyury proteins and Brachyury polypeptides disclosed herein, nucleic acids encoding the Brachyury proteins or Brachyury polypeptides, or host cells including these nucleic acids can be used to generate an immune response in a subject, such as, but not limited to, a Brachyury specific CD4+ T cell response and/or a Brachyury CD8+ T cells response. In several examples, the subject has a cancer that expresses Brachyury. In other embodiments, the method is a method for preventing cancer in the subject. The subject can be at risk of developing cancer. In specific non-limiting examples, the subject has high grade prostatic intraepithelial neoplasia, familial adenomatous polyposis, or atypia of the breast. The methods include administering to a subject a therapeutically effective amount of one or more of the Brachyury proteins and/or polypeptides disclosed herein, nucleic acids encoding these Brachyury proteins or Brachyury polypeptides, host cells, such as Listeria or Salmonella host cells, dendritic cells presenting epitopes of the protein or polypeptide, and/or vectors including these nucleic acids, in order to generate an immune response.

The methods can include selecting a subject in need of treatment, such as a subject with a cancer that expresses Brachyury or a cancer with the potential to express Brachyury. In several examples, the methods include selecting a subject with a cancer of the small intestine, stomach, kidney, bladder, uterus, ovaries, testes lung, colon, prostate, tumor of B cell origin (such as chronic lymphocytic leukemia (CLL), a B cell lymphoma, Burkitt's lymphoma or a Hodgkin's lymphoma) or breast cancer wherein the cancer expresses Brachyury or has the potential to express Brachyury. In some non-limiting examples, examples, the cancer is radiation resistant and/or chemotherapy resistant. In additional non-limiting examples, the subject has breast cancer, such as a ductal carcinoma, for example an infiltrating ductal carcinoma or an estrogen receptor negative and progesterone receptor negative breast cancer. In further examples, the subject has high-grade prostatic intraepithelial neoplasia, familial adenomatous polyposis, or atypia of the breast.

In exemplary applications, compositions are administered to a subject in an amount sufficient to raise an immune response to Brachyury-expressing cells, such as a CD4+ T cell response. A Brachyury specific CD8+ T cell response can also be induced using the methods disclosed herein. Administration induces a sufficient immune response to slow the proliferation of Brachyury-expressing cells, or to inhibit their growth, or to reduce a sign or a symptom of the cancer, or to prevent a cancer. Amounts effective for this use will depend upon the severity of the disease, the general state of the patient's health, and the robustness of the patient's immune system. In one example, a therapeutically effective amount of the composition is that which provides either subjective relief of a symptom(s) or an objectively identifiable improvement as noted by the clinician or other qualified observer. The composition can include a Brachyury protein and/or a Brachyury polypeptide, a nucleic acid encoding a Brachyury protein and/or a Brachyury polypeptide, a vector including the nucleic acid, or a host cell expressing the Brachyury protein and/or Brachyury polypeptide. It should be noted that these compositions can be used in combination.

The composition can be administered by any means known to one of skill in the art (see Banga, A., "Parenteral Controlled Delivery of Therapeutic Peptides and Proteins," in *Therapeutic Peptides and Proteins*, Technomic Publishing Co., Inc., Lancaster, Pa., 1995). Thus, the composition can be administered either locally or systemically, such as by intramuscular, subcutaneous, intraperitoneal or intravenous injection, but even oral, nasal, transdermal or anal administration is contemplated. In one embodiment, administration is by subcutaneous or intramuscular injection.

Use of Proteins, Polypeptides, Nucleic Acids and Host Cells

When the Brachyury protein and/or the Brachyury polypeptide is administered, to extend the time during which protein is available to stimulate a response, the protein and/or polypeptide can be provided as an implant, an oily injection, in a liposome, or as a particulate system. The particulate system can be a microparticle, a microcapsule, a microsphere, a nanocapsule, or similar particle. (see, e.g., Banga, supra). A particulate carrier based on a synthetic polymer has been shown to act as an adjuvant to enhance the immune response, in addition to providing a controlled release. Adjuvants can also be used in combination with the protein, including, for example, chitosan, aluminum salts, an immunostimulatory oligodeoxynucleotoide, liposomes and/or one or more cytokines. The Brachyury protein or polypeptide can be administered in a liposome.

In one specific, non-limiting example, the Brachyury protein is administered in a manner to direct the immune response to a cellular response (that is, a Brachyury specific CD4+ response and/or CD8+ response), rather than a humoral (antibody) response. The Brachyury polypeptide can induce both a Brachyury specific CD4+ T cell response and a Brachyury specific CD8+ T cell response. Methods for measuring a CD4+ and CD8+ T cell response are known in the art, and include biological assays, ELISPOT assays, and fluorescence activated cell sorting. An exemplary assay for measuring Brachyury specific CD4+ T cells is disclosed in the examples below.

In one specific, non-limiting example, a pharmaceutical composition for intravenous administration would include about 0.1 μg to 10 mg of immunogenic Brachyury protein and/or Brachyury polypeptide per patient per day. Dosages from 0.1 up to about 100 mg per patient per day can be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remingtons Pharmaceutical Sciences*, 19$^{th}$ Ed., Mack Publishing Company, Easton, Pa., 1995.

Optionally, one or more immunostimulatory molecules, such as IL-2, IL-6, IL-12, LFA (for example, LFA-1, LFA-2 and/or LFA-3), CD72, RANTES, G-CSF, GM-CSF, TNF-α, IFN-γ, ICAM-1, B7-1, B7-2, other B7 related molecules, OX-40L and/or or 41 BBL, or combinations of these molecules, can be used as biological adjuvants (see, for example, Salgaller et al., 1998, J. Surg. Oncol. 68(2):122-38; Lotze et al., 2000, Cancer J Sci. Am. 6(Suppl 1):S61-6; Cao et al., 1998, Stem Cells 16(Suppl 1):251-60; Kuiper et al., 2000, Adv. Exp. Med. Biol. 465:381-90). These molecules can be administered systemically (or locally) to the host. In several examples, IL-2, RANTES, GM-CSF, TNF-α, IFN-γ, G-CSF, LFA-3, CD72, B7-1, B7-2, B7-1, B7-2, OX-40L, 41 BBL and/or ICAM-1 are administered. IL-15 or an IL-15/IL-15 receptor complex can be administered.

A number of means for inducing cellular responses, both in vitro and in vivo, are known. Lipids have been identified as agents capable of assisting in priming T cells in vivo against various antigens. For example, as described in U.S. Pat. No. 5,662,907, palmitic acid residues can be attached to the alpha and epsilon amino groups of a lysine residue and then linked (for example, via one or more linking residues, such as glycine, glycine-glycine, serine, serine-serine, or the like) to an immunogenic peptide or protein. The lipidated peptide can then be injected directly in a micellar form, incorporated in a liposome, or emulsified in an adjuvant. As another example, *E. coli* lipoproteins, such as tripalmitoyl-S-glycerylcysteinlyseryl-serine can be used to prime tumor specific T cells when covalently attached to an appropriate peptide or protein (see, Deres et al., Nature 342:561, 1989). Further, as the induction of neutralizing antibodies can also be primed with the same molecule conjugated to a protein which displays an appropriate epitope, two compositions can be combined to elicit both humoral and cell-mediated responses where that is deemed desirable.

A pharmaceutical composition including a Brachyury protein and/or Brachyury polypeptide is thus provided. These compositions are used to generate an immune response, such as for immunotherapy.

In one embodiment, the Brachyury protein and/or the Brachyury polypeptide is mixed with an adjuvant containing two or more of a stabilizing detergent, a micelle-forming agent, and an oil. Suitable stabilizing detergents, micelle-forming agents, and oils are detailed in U.S. Pat. Nos. 5,585,103; 5,709,860; 5,270,202; and 5,695,770, all of which are incorporated by reference. A stabilizing detergent is any detergent that allows the components of the emulsion to remain as a stable emulsion. Such detergents include polysorbate, 80 (TWEEN) (Sorbitan-mono-9-octadeceno-ate-poly(oxy-1,2-ethanediyl; manufactured by ICI Americas, Wilmington, Del.), TWEEN 40™, TWEEN 20™, TWEEN 60™, Zwittergent™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, e.g., Schmolka, *J. Am. Oil. Chem. Soc.* 54:110, 1977, and Hunter et al., *J. Immunol* 129:1244, 1981, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, *J. Immun.* 133:3167, 1984. The agent can be provided in an effective amount, for example between 0.5 and 10%, or in an amount between 1.25 and 5%.

The oil included in the composition is chosen to promote the retention of the antigen in oil-in-water emulsion, such as to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, Squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse affects, such as granulomas, are evident upon use of the oil.

In one embodiment, the adjuvant is a mixture of stabilizing detergents, micelle-forming agent, and oil available under the name PROVAX® (IDEC Pharmaceuticals, San Diego, Calif.). In other embodiments, the Brachyury protein and/or Brachyury polypeptide are included in a liposome.

Adjuvants can also be administered with the Brachyury protein and/or Brachyury polypeptide. An adjuvant can be any immunostimulatory molecule, such as a cytokine, immunostimulatory nucleic acid, or a biological adjuvant (see above). The adjuvant can be chitosan. Chitosan is a linear polysaccharide formed from repeating beta (1-4 linked) N-acetyl-D-glucosamine and D-glucosamine units, and is derived from the partial deacetylation of chitin obtained from the shells of crustaceans. Chitosan can be made commercially by a heterogeneous alkaline hydrolysis of chitin to give a product which possesses a random distribution of remaining acetyl moieties. The properties of chitosans depend upon inter alia the degree of deacetylation, and the molecular weight. Most commercially available chitosans contain a population of chitosan molecules of varying molecular weights and varying concentrations of the component N-acetyl-D-glucosamine and D-glucosamine groups. The immunological properties of chitosans are known to be linked to the ratio between the N-acetyl-D-glucosamine and D-glucosamine groups. The efficacy of chitosans as adjuvants depends to a considerable extent on the extent of the level of deacetylation. Thus, in some embodiments, the chitosan is at least 80% deacetylated, see U.S. Pat. No. 6,534,065, which is incorporated herein by reference.

Controlled release parenteral formulations can be made as implants, oily injections, or as particulate systems. For a broad overview of protein delivery systems, see Banga, *Therapeutic Peptides and Proteins: Formulation, Processing, and Delivery Systems*, Technomic Publishing Company, Inc., Lancaster, Pa., 1995. Particulate systems include microspheres, microparticles, microcapsules, nanocapsules, nanospheres, and nanoparticles. Microcapsules contain the therapeutic protein as a central core. In microspheres, the therapeutic agent is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly (see Kreuter, *Colloidal Drug Delivery Systems*, J. Kreuter, ed., Marcel Dekker, Inc., New York, N.Y., pp. 219-342, 1994; Tice & Tabibi, *Treatise on Controlled Drug Delivery*, A. Kydonieus, ed., Marcel Dekker, Inc. New York, N.Y., pp. 315-339, 1992).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec. *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (e.g., U.S. Pat. Nos. 5,055,303; 5,188,837; 4,235,871; 4,501,728; 4,837,028; 4,957,735; and 5,019,369; 5,055,303; 5,514,670; 5,413,797; 5,268,164; 5,004,697; 4,902,505; 5,506,206; 5,271,961; 5,254,342; and 5,534,496).

In another embodiment, the composition includes a nucleic acid encoding a Brachyury protein and/or a Brachyury polypeptide. A therapeutically effective amount of the polynucleotide encoding the Brachyury protein and/or the Brachyury polypeptide can be administered to a subject in order to generate an immune response. In one specific, non-limiting example, a therapeutically effective amount of the polynucleotide encoding the Brachyury protein and/or Brachyury polypeptide is administered to a subject to treat or prevent cancer.

Optionally, one or more immunostimulatory molecules and/or costimulatory molecules, such as IL-2, IL-6, IL-12, LFA (for example, LFA-1, LFA-2 and/or LFA-3), CD72, RANTES, G-CSF, GM-CSF, TNF-α, IFN-γ ICAM-1, B7-1, B7-2, other B7 related molecules, OX-40L or 41 BBL, or combinations of these molecules, can be used as biological adjuvants (see, for example, Salgaller et al., 1998, J. Surg. Oncol. 68(2):122-38; Lotze et al., 2000. Cancer J Sci. Am. 6(Suppl 1):S61-6; Cao et al., 1998, Stem Cells 16(Suppl 1):251-60; Kuiper et al., 2000, Adv. Exp. Med. Biol. 465: 381-90). These molecules can be administered systemically (or locally) to the host. In several examples, IL-2, RANTES, GM-CSF, TNF-α, IFN-γ, G-CSF, LFA-3, CD72, B7-1, B7-2, B7-1, B7-2, OX-40L, 41 BBL and/or ICAM-1 are administered. L-15 or an IL-15/IL-15 receptor complex can be administered.

Optionally, a non-pox non-yeast vector is administered that encodes one or more immunostimulatory or costimulatory molecules, such as IL-2, IL-6, IL-12, IL-15, LFA (for example, LFA-1, LFA-2 and/or LFA-3), CD72, RANTES, G-CSF, GM-CSF, TNF-α, IFN-γ, ICAM-1, B7-1, B7-2, other B7 related molecules, OX-40L or 41 BBL, or combinations of these molecules (see, for example, Salgaller et al., 1998, J. Surg. Oncol. 68(2):122-38; Lotze et al., 2000, Cancer J Sci. Am. 6(Suppl 1):S61-6; Cao et al., 1998, Stem Cells 16(Suppl 1):251-60; Kuiper et al., 2000, Adv. Exp. Med. Biol. 465:381-90). In several examples, the vector can encode IL-2, RANTES, GM-CSF, TNF-α, IFN-γ, G-CSF, LFA-3, CD72, B7-1, B7-2, B7-1, B7-2, OX-40L, 41 BBL and/or ICAM-1. In various embodiments, the nucleic acid encoding the biological adjuvant can be cloned into same vector as the Brachyury protein or Brachyury polypeptide coding sequence, or the nucleic acid can be cloned into one or more separate vectors for co-administration. In addition, nonspecific immunomodulating factors such as *Bacillus* Cahnette-Guerin (BCG) and levamisole can be co-administered.

One approach to administration of nucleic acids is direct immunization with plasmid DNA, such as with a mammalian expression plasmid. As described above, the nucleotide sequence encoding a Brachyury protein or polypeptide can be placed under the control of a promoter to increase expression of the molecule.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 μg encapsulated in ISCOMS™ have been found to produce Class I mediated CTL responses (Takahashi et al., *Nature* 344:873, 1990). In other embodiments, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites, including tissues in proximity to metastases. Dosages for injection are usually around 0.5 μg/kg to about 50 mg/kg, and typically are about 0.005 mg/kg to about 5 mg/kg (see, for example, U.S. Pat. No. 5,589,466).

In another approach to using nucleic acids for immunization, a Brachyury protein or Brachyury polypeptide can also be expressed by attenuated host cells or non-pox non-yeast viral vectors. These vectors and host cells are disclosed above. Suitable non-pox non-yeast viral vector, include an adenovirus, an alphavirus, a lentivirus, a measles virus or a poliovirus vector. Suitable host cell include an attenuated bacterium, such as *Listeria* or *Salmonella* host cells.

A first recombinant non-pox virus encoding a Brachyury protein can be used in conjunction with a second recombinant non-pox virus which has incorporated into a viral genome or infectable portion thereof one or more genes or DNA sequences encoding B7-1, B7-2, or B7-1 and B7-2, wherein the composition is able to coinfect a host cell resulting in coexpression of the polypeptide and the B7-1, B7-2, or B7-1 and B7-2 encoding genes or DNA sequences (see U.S. Pat. Nos. 6,893,869, and 6,045,908, which are incorporated by reference herein). The expression of the B7 gene family has been shown to be an important mechanism of anti-tumor responses in both mice and humans.

When a non-pox viral vector is utilized, it is desirable to provide the recipient with a dosage of each recombinant virus in the composition in the range of from about $10^5$ to about $10^{10}$ plaque forming units/mg mammal, although a lower or higher dose can be administered. The composition of recombinant viral vectors can be introduced into a mammal either prior to any evidence of a cancer, or to mediate regression of the disease in a mammal afflicted with the cancer. Examples of methods for administering the composition into mammals include, but are not limited to, exposure of cells to the recombinant virus ex vivo, or injection of the composition into the affected tissue or intravenous, subcutaneous, intradermal or intramuscular administration of the virus. Alternatively the recombinant viral vector or combination of recombinant viral vectors may be administered locally by direct injection into the cancerous lesion in a pharmaceutically acceptable carrier. Generally, the quantity of recombinant non-pox viral vector, carrying the nucleic acid sequence of a Brachyury protein or Brachyury polypeptide to be administered is based on the titer of virus particles. An exemplary range of the immunogen to be administered is $10^5$ to $10^{10}$ virus particles per mammal, such as a human.

In the embodiment where a combination of a first recombinant viral vector carrying a nucleic acid sequence of a Brachyury protein or Brachyury polypeptide and a second recombinant viral vector carrying the nucleic acid sequence of one or more costimulatory or immunostimulatory molecules is used, the mammal can be immunized with different ratios of the first and second recombinant viral vector. In one embodiment the ratio of the first vector to the second vector is about 1:1, or about 1:3, or about 1:5. Optimal ratios of the first vector to the second vector may easily be titered using the methods known in the art (see, for example, U.S. Pat. No. 6,893,869, incorporated herein by reference). Simultaneous production of an immunostimulatory molecule and the Brachyury protein or Brachyury polypeptide enhances the generation of specific effectors. Without being bound by theory, dependent upon the specific immunostimulatory molecules, different mechanisms might be responsible for the enhanced immunogenicity: augmentation of help signal (IL-2), recruitment of professional APC (GM-CSF), increase in CTL frequency (IL-2), effect on antigen processing pathway and MHC expression (IFNγ and TNFα) and the like. For example, IL-2, IL-6, IL-15, interferon, tumor necrosis factor, or a nucleic acid encoding these molecules, can be administered in conjunction with a Brachyury protein, or a nucleic acid encoding a Brachyury protein or Brachyury polypeptide. The co-expression of a Brachyury protein or Brachyury polypeptide together with at least one immunostimulatory molecule can be effective in an animal model to show anti-tumor effects.

Single or multiple administrations of the compositions are administered depending on the dosage and frequency as required and tolerated by the subject. In one embodiment, the dosage is administered once as a bolus, but in another embodiment can be applied periodically until a therapeutic result is achieved. Generally, the dose is sufficient to induce an immune response to Brachyury, to treat or ameliorate symptoms or signs of disease, without producing unacceptable toxicity to the subject. Systemic or local administration can be utilized.

Use of Antigen Presenting Cells

In another method, antigen presenting cells (APCs), such as dendritic cells, are pulsed or co-incubated with a Brachyury protein and/or Brachyury polypeptide in vitro. In one specific, non-limiting example, the antigen presenting cells can be autologous cells. A therapeutically effective amount of the antigen presenting cells, such as dendritic cells presenting epitopes of the protein or polypeptide can then be administered to a subject. In some embodiments, the method is a method of treating and/or preventing cancer in a subject.

The Brachyury protein and/or Brachyury polypeptide can be delivered to the dendritic cells or to dendritic cell precursors via any method known in the art, including, but not limited to, pulsing dendritic cells directly with antigen, or utilizing a broad variety of antigen delivery vehicles, such as, for example, liposomes, or other vectors known to deliver antigen to cells. In one specific, non-limiting example an antigenic formulation includes about 0.1 µg to about 1,000 µg, or about 1 to about 100 µg of a selected Brachyury protein. The Brachyury protein can also be administered with agents that promote dendritic cell maturation. Specific, non-limiting examples of agents of use are interleukin-4 (IL-4) and granulocyte/macrophage colony stimulating factor (GM-CSF), or flt-3 ligand (flt-3L). The preparation can also contain buffers, excipients, and preservatives, amongst other ingredients.

In one embodiment, mature antigen presenting cells are generated to present the Brachyury protein and/or Brachyury polypeptide epitopes. These dendritic cells are then administered alone (or in combination with another agent) to a subject with a cancer that expresses Brachyury, or has the potential to express Brachyury, such as a small intestine, stomach, kidney, bladder, uterus, ovary, testis, lung colon, prostate cancer, a tumor of B cell origin (such as chronic lymphocytic leukemia (CLL), a B cell lymphoma, Burkitt's lymphoma or a Hodgkin's lymphoma) or breast cancer, such as an infiltrating ductal carcinoma or an estrogen receptor negative and progesterone receptor negative breast cancer. In some examples, the cancer is radiation resistant and/or chemotherapy resistant. The antigen presenting cells can also be administered to prevent these cancers. The subject can have high grade prostatic intraepithelial neoplasia, familial adenomatous polyposis, or atypia of the breast.

The cells can be administered to a subject to inhibit the growth of cells of Brachyury expressing cancer or a cancer that has the potential to express Brachyury. In these applications, a therapeutically effective amount of activated antigen presenting cells are administered to a subject suffering from a disease, in an amount sufficient to raise an immune response to Brachyury-expressing cells. The resulting immune response is sufficient to slow the proliferation of such cells or to inhibit their growth, or to reduce a sign or a symptom of the tumor.

In a supplemental method, any of these immunotherapies is augmented by administering a cytokine, such as interleukin (IL)-2, IL-3, IL-6, IL-10, IL-12, IL-15, GM-CSF, or interferons. In another embodiment, the mature dendritic cells are administered in conjunction with a chemotherapeutic agent.

Combination Therapy

In some embodiments, the subject is administered a Brachyury protein, a Brachyury polypeptide, a nucleic acid encoding a Brachyury protein, a host cell expressing the Brachyury protein, and/or dendritic cells, and is administered an additional agent. In one example, this administration is sequential. However, the administration can be simultaneous.

In some embodiments the subject has cancer. The cancer can express Brachyury or have the potential to express Brachyury. Thus, the additional agent can be a chemotherapeutic agent. Additional agents include radiation, small molecule targeted therapies, monoclonal antibodies, and/or checkpoint inhibitors, such as anti-PD-1, anti-PD-L1, anti-CTLA-4, and others. In some embodiments, the subject is administered an epithelial growth factor receptor inhibitor, a transforming growth factor (TGF)-β inhibitor, or a tyrosine kinase inhibitor.

In some embodiments, the additional chemotherapeutic agent is an epithelial growth factor receptor (EGFR) inhibitor. Numerous compounds are known that inhibit EGFR, see for example, U.S. Pat. Nos. 5,196,446; 5,217,999; 5,459,061; 7,049,410; 6,355,678, which are incorporated herein by reference. A number of EGFR inhibitors are in clinical development, such as for the treatment of lung cancer. These include tustuzumab, lapatinib, pertuzumab, panitumumab, genfitinib (IRESSA®), erlotinib (TARCEVA®), cetuximab (ERTIBUX®), afatinib, necitumumab, nimotuzumab, PF299804 (Pfizer), RO5083945 (Roche), ABT-806 (Abbott) and AP2113 (Ariad). In other embodiments, the additional chemotherapeutic agent is a tyrosine kinase inhibitor. These include, but are not limited to avastin and termsirolimus.

Examples of additional agents of use are alkylating agents, antimetabolites, natural products, or hormones and their antagonists. Examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine). Examples of antimetabolites include folic acid analogs (such as methotrexate), pyrimidine analogs (such as 5-FU or cytarabine), and purine analogs, such as mercaptopurine or thioguanine. Examples of natural products include *vinca* alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase). Examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocortical suppressants (such as mitotane and aminoglutethimide). Examples of hormones and antagonists include adrenocorticosteroids (such as prednisone), progestins (such as hydroxyprogesterone caproate, medroxyprogesterone acetate, and megestrol acetate), estrogens (such as diethylstilbestrol and ethinyl estradiol), antiestrogens (such as tamoxifen), and androgens (such as testosterone proprionate and fluoxymesterone). Examples of the most commonly used chemotherapy drugs that can be concurrently administered with the disclosed immunotherapy include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere. Topotecan (Hycamtin). Xeloda (Capecitabine), Zevelin and calcitriol. Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor, Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

The additional agent can be a small molecule, a vaccine, or a biologic. For example, when the additional agent is a vaccine, the vaccine can be a yeast-based or viral-based (e.g., poxviral-based) vaccine. Examples of viral vectors include poxvirus, retrovirus, adenovirus, adeno-associated virus, herpes virus, polio virus, alphavirus, baculorvirus, and Sindbis virus. In one embodiment, the viral vector is a poxvirus selected from the group consisting of orthopox, avipox, fowlpox, raccoon pox, rabbit pox, capripox (e.g., sheep pox), leporipox, and suipox (e.g., swinepox). Examples of avipox viruses include fowlpox, pigeonpox, and canarypox, such as ALVAC. Examples of orthopox viruses include vaccinia, modified vaccinia Ankara (MVA), Wyeth, NYVAC, TROYVAC, Dry-Vax, POXVAC-TC (Schering-Plough Corporation), and derivatives thereof. For example, derivatives of the Wyeth strain include, but are not limited to, derivatives which lack a functional K1L gene.

The vaccine can encode any suitable antigen, such as the Brachyury protein or Brachyury polypeptide described herein, 5-α-reductase, α-fetoprotein ("AFP"), AM-1, APC, April, B melanoma antigen gene ("BAGE"), β-catenin, Bcl12, bcr-abl, Brachyury, CA-125, caspase-8 ("CASP-8", also known as "FLICE"), Cathepsins, CD19, CD20, CD21/ complement receptor 2 ("CR2"), CD22/BL-CAM, CD23/ $F_c\epsilon RII$, CD33, CD35/complement receptor 1 ("CR1"), CD44/PGP-1, CD45/leucocyte common antigen ("LCA"), CD46/membrane cofactor protein ("MCP"), CD52/CAMPATH-1, CD55/decay accelerating factor ("DAF"), CD59/ protectin, CDC27, CDK4, carcinoembryonic antigen ("CEA"), c-myc, cyclooxygenase-2 ("cox-2"), deleted in colorectal cancer gene ("DCC"), DcR3, E6/E7, CGFR, EMBP, Dna78, farnesyl transferase, fibroblast growth factor-8a ("FGF8a"), fibroblast growth factor-8b ("FGF8b"), FLK-1/KDR, folic acid receptor, G250, G melanoma antigen gene family ("GAGE-family"), gastrin 17, gastrin-releasing hormone, ganglioside 2 ("GD2")/ganglioside 3 ("GD3")/ganglioside-monosialic acid-2 ("GM2"), gonadotropin releasing hormone ("GnRH"), UDP-GlcNAc:$R_1$Man ($\alpha$1-6)$R_2$ [GlcNAc to Man($\alpha$1-6)]$\beta$1,6-N-acetylglucosaminyltransferase V ("GnT V"), GP1, gp100/Pme 17, gp-100-in4, gp15, gp75/tyrosine-related protein-1 ("gp75/TRP-1"), human chorionic gonadotropin ("hCG"), heparanase, Her2/ neu, human mammary tumor virus ("HMTV"), 70 kiloDalton heat-shock protein ("HSP70"), human telomerase reverse transcriptase ("hTERT"), insulin-like growth factor receptor-1 ("IGFR-1"), interleukin-13 receptor ("IL-13R"), inducible nitric oxide synthase ("iNOS"), Ki67, KIAA0205, K-ras, H-ras, N-ras, KSA, LKLR-FUT, melanoma antigen-encoding family ("MAGE-family", including at least MAGE-1, MAGE-2, MAGE-3, and MAGE-4), mammaglobin, MAP17, Melan-A/melanoma antigen recognized by T-cells-1 ("MART-1"), mesothelin, MIC A/B, MT-MMPs, mucin, testes-specific antigen NY-ESO-1, osteonectin, p15, P170/MDR1, p53, p97/melanotransferrin, PAI-1, platelet-derived growth factor ("PDGF"), µPA, PRAME, probasin, progenipoietin, prostate-specific antigen ("PSA"), prostate-specific membrane antigen ("PSMA"), RAGE-1, Rb, RCAS1, SART-1, SSX-family, STAT3, STn, TAG-72, transforming growth factor-alpha ("TGF-α"), transforming growth factor-beta ("TGF-β"), Thymosin-beta-15, tumor necrosis factor-alpha ("TNF-α"), TP1, TRP-2, tyrosinase, vascular endothelial growth factor ("VEGF"), ZAG, p16INK4, and/or glutathione-S-transferase ("GST").

In one embodiment, the vaccine is PROSTVAC™, which is a sequentially dosed combination of two different poxviruses each encoding prostate specific antigen (PSA) plus three immune enhancing co-stimulatory molecules, B7.1, ICAM-1, and LFA-3 (TRICOM). The first poxvirus is Vaccinia-PSA-TRICOM, and the second poxvirus is Fowlpox-PSA-TRICOM.

Thus, the invention provides a method for treating or preventing cancer in a subject comprising administering to the subject a combination therapy comprising:

(1) (a) a protein comprising an amino acid sequence at least 90% identical to the amino acid sequence set forth as SEQ ID NO: 1; (b) a polypeptide comprising at least 15 consecutive amino acids of the amino acid sequence set forth at SEQ ID NO: 1; (c) a nucleic acid encoding the protein or the polypeptide; (d) a host cell expressing the protein or the polypeptide; or (e) a non-pox non-yeast vector encoding the protein or the polypeptide, and (2) a small molecule, a vaccine (e.g., a pox-viral or yeast vaccine as described above), or a biologic, thereby treating or preventing cancer in the subject.

EXAMPLES

Example 1: Induction of CD4+ Cells Using Brachyury Protein or Brachyury Polypeptide FIGS. 1 and 2 show the induction of CD4+ cells using Brachyury protein and a Brachyury polypeptide.

I. FIG. 1

Methods:

Dendritic cells (DCs) from 2 normal donors were prepared from the adherent cell fraction of peripheral blood mononuclear cells (PBMCs) by culture in the presence of GM-CSF and IL-4. On day 5, a purified, recombinant full length Brachyury protein was added to the cultures (10 µg/ml) for 48 hours. For donor 2, an additional culture was set up using purified HSA (human serum albumin) control protein (10 µg/ml). On day 7, protein-pulsed DCs were harvested, irradiated (20 Gy) and used as antigen-presenting cells (APCs) to stimulate autologous PBMCs (ratio DC:PBMCs equal to 1:10). On days 3 and 5, IL-2 (20 U/ml) was added to the cultures. Cells were harvested on day 7 and CD4+ T cells were isolated by negative selection utilizing CD4 purification magnetic beads (Miltenyi Biotec). CD4+ T cells were subsequently stimulated in a similar manner for an additional 7-day cycle. On day 7, CD4+ T cells were re-purified by using CD4 purification magnetic beads, and evaluated for IFN-gamma production in response to autologous, irradiated PBMCs (ratio PBMCs:CD4+ T cells equal to 3:1) alone or pulsed with control HSA protein vs. Brachyury protein (10 µg/ml). Culture supernatants were collected at 96 hours and evaluated for IFN-gamma by ELISA.

Summary of Findings:

As shown in FIG. 1, Brachyury-specific CD4+ T cells can be expanded from the blood of normal donors by culture of PBMCs in the presence of autologous DCs pulsed with a purified, full length Brachyury protein. After 2 rounds of in vitro stimulation, Brachyury-specific CD4+ T cells specifically released IFN-gamma in response to stimulation with autologous PBMCs pulsed with purified Brachyury protein (full length, recombinant) but not with a control, irrelevant protein (HAS).

II. FIG. 2

Methods:

A CD4+ Brachyury-specific T-cell line (T-BRA) was generated from a prostate patient vaccinated with a PSA-based vaccine. CD40L-matured autologous DCs were used as antigen-presenting cells (APCs). PBMCs obtained on day 90 post-vaccination were added to the APCs and pulsed with 10 µg/mL of Brachyury 9-mer agonist peptide (WLLPGTSTV) at an effector:APC ratio of 10:1. The culture was then incubated for 3 days at 37° C. in a humidified atmosphere containing 5% $CO_2$. The culture was then supplemented with recombinant human IL-7 and IL-15 at a concentration of 10 ng/ml for 5 days. The 3-day incubation with peptide and 5-day IL-7 and IL-15 supplement constituted one in vitro stimulation (IVS) cycle. Autologous DCs were used as APCs for 3 in vitro stimulation (IVS) cycles. Irradiated (23,000 rads) autologous EBV-transformed B cells were used as APCs after the third IVS cycle. For re-stimulation with EBV-transformed B cells, peptides at a concentration of 10 µg/mL were used to pulse the autologous EBV-transformed B cells at an effector:APC ratio of 1:3. CD4+ T cells were then isolated from the cell culture at the end of the 4th IVS and stimulated with a Brachyury class II 15-mer peptide (Brachyury class IIB)(QWGWLLPGTSTL). The cultures were then supplemented with recombinant human IL-7 and IL-15 at a concentration of 10 ng/mL for 5 days. The CD4+ T cell line was then assayed for specificity to the Brachyury class IIB epitope by stimulation with APCs pulsed with the Brachyury class IIB or a control Brachyury class IIA epitope.

Example 2: Brachyury in Carcinoma

FIGS. 3-7 show the results achieved.

TABLE 1

Expression of Brachyury in primary breast carcinoma tissues by immunohistochemistry utilizing a murine monoclonal anti-brachyury Ab

| | Tumor | | Adjacent | Distal |
|---|---|---|---|---|
| Pt # | % Positivity | Intensity | tissue | tissue |
| 1 | 80 | ++ | pos | neg |
| 2 | 80 | ++ | pos | neg |
| 3 | 90 | ++ | pos | neg |
| 4 | 90 | + | neg | neg |
| 5 | 90 | + | pos | neg |
| 6 | 30 | + | neg | neg |
| 7 | 15 | +++ | neg | neg |
| 8 | 60 | + | neg | neg |
| 9 | focal | + | neg | neg |
| 10 | 70 | + | neg | neg |
| 11 | 40 | + | neg | neg |
| 12 | 30 | + | neg | neg |
| 13 | focal | + | neg | neg |
| 14 | 90 | +++ | neg | neg |
| 15 | 90 | −/+ | pos | neg |
| 16 | 30 | + | neg | neg |
| 17 | neg | neg | neg | neg |
| 18 | 50 | ++ | neg | neg |
| 19 | neg | neg | neg | neg |
| 20 | neg | neg | neg | neg |
| 21 | 40 | ++ | pos | neg |
| 22 | 30 | ++ | pos | neg |

TABLE 1-continued

Expression of Brachyury in primary breast carcinoma tissues by immunohistochemistry utilizing a murine monoclonal anti-brachyury Ab

| | Tumor | | Adjacent | Distal |
|---|---|---|---|---|
| Pt # | % Positivity | Intensity | tissue | tissue |
| 23 | 85 | ++ | pos | neg |
| 24 | 80 | +++ | pos | neg |
| 25 | 30 | + | pos | neg |
| 26 | 50 | ++ | pos | neg |
| 27 | 65 | ++ | pos | NA |
| 28 | 40 | +++ | pos | neg |
| 29 | 25 | ++ | pos | NA |
| 30 | 15 | + | pos | NA |

Pos = positive;
neg = negative;
NA = not available

TABLE 2

Brachyury expression in primary breast carcinoma tissues by immunohistochemistry by lymph node status, tumor grade, and hormone receptor expression

| Tumor tissue sample | Number of tumors positive for Brachyury |
|---|---|
| Lymph node status: | |
| Node-negative | 13/15 (86.7%)* |
| Node-positive | 10/11 (93.3%) |
| Grade: | |
| G1 | 2/3 (66.7%) |
| G2 | — |
| G3 | 25/27 (92.6%) |
| ER/PR expression: | |
| ER+ PR+ | 4/6 (66.7%) |
| ER− PR− | 21/22 (95.5%) |
| ER/PR/HER2 expression: | |
| ER+ PR+ HER2+ | 1/2 (50.0%) |
| ER+ PR+ HER2− | 3/4 (75.0%) |
| ER− PR− HER2+ | 12/12 (100.0%) |
| ER− PR− HER2− | 9/10 (90.0%) |

Statistical analysis was performed, comparing node-positive vs. node-negative, grade 3 vs. grade 1, and ER− PR− vs. ER+ PR+ samples.
*Numbers in parentheses indicate percentage.

TABLE 3

Expression of Brachyury in metastatic breast carcinoma lesions by immunohistochemistry using a murine monoclonal anti-brachyury Ab

| | | Brachyury | |
|---|---|---|---|
| Pt # | Site | % Positivity | Intensity |
| 6 | Breast primary tumor | 30 | + |
| 6 | Met+ lymph node (a) | 90 | + |
| 6 | Met+ lymph node (b) | 90 | + |
| 6 | Non-met lymph node | neg | neg |
| 9 | Breast primary tumor | focal | + |
| 9 | Met+ lymph node (a) | 60 | ++ |
| 9 | Met+ lymph node (b) | 60 | ++ |
| 9 | Non-met lymph node | neg | neg |
| 31 | Pleura | 90 | + |
| 32 | Bone | 90 | ++ |
| 33 | Bone | 90 | + |
| 34 | Brain | 70 | ++ |

Human matched breast primary tumor tissues and metastatic lymph nodes from two patients were analyzed for Brachyury expression by immunohistochemistry. The breast primary tumor tissue samples were from infiltrating ductal adenocarcinomas. Two lymph nodes positive for metastasis from each patient (a, b) and 1 lymph node negative for metastasis from same patient (c) were assayed. Metastatic lesions from additional patients were also analyzed for Brachyury expression by immunohistochemistry. Adjacent and distal breast tissues in the samples were negative for Brachyury expression.

The breast primary tumor tissue samples were from 30 infiltrating ductal adenocarcinomas. Brachyury expression for each sample is reported as staining in tumor cells (% positivity, intensity), staining in breast adjacent tissue, and staining in breast distal tissue.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for inducing a Brachyury specific CD4+ T cell response, the method comprising
    administering to a subject an effective amount of an adenoviral vector encoding (i) a polypeptide comprising SEQ ID NO: 5 or (ii) a polypeptide consisting of SEQ ID NO: 6, and
    measuring the Brachyury specific CD4+ T cell response.

2. The method of claim 1, further comprising measuring a Brachyury specific CD8+ T cell response.

3. The method of claim 1, wherein the subject is human.

4. The method of claim 1, wherein the subject has cancer.

5. The method of claim 4, wherein the cancer is a breast cancer, small intestine cancer, stomach cancer, kidney cancer, bladder cancer, uterus cancer, ovarian cancer, testes cancer, lung cancer, colon cancer, prostate cancer, chronic lymphocytic leukemia (CLL), a B cell lymphoma, a Burkitt's lymphoma or a Hodgkin's lymphoma.

6. The method of claim 1, comprising administering to the subject an effective amount of the adenoviral vector encoding the protein-sufficient to induce Brachyury specific CD4+ T cells and/or CD8+ T cells.

7. The method of claim 1, wherein the adenoviral vector encodes a costimulatory molecule.

8. The method of claim 7, wherein the costimulatory molecule is one or more of B7-1, B7-2, LFA-3 or ICAM-1.

9. The method of claim 1, wherein the adenoviral vector comprises a DNA sequence encoding an immunostimulatory molecule, wherein the immunostimulatory molecule is selected from the group consisting of IL-2, ICAM-1, LFA-3, CD72, GM-CSF, TNF-α, IFN-γ, IL-12, and IL-6.

10. The method of claim 1, further comprising administering to the subject an effective amount of an adjuvant.

11. The method of claim 10, wherein the adjuvant is chitosan.

12. The method of claim 1, further comprising administering to the subject a therapeutically effective amount of an agent selected from the group consisting of a chemotherapeutic agent, radiation, a small molecule targeted therapeutic, and monoclonal antibodies.

13. The method of claim 12, wherein the agent is an epithelial growth factor receptor inhibitor, a transforming growth factor (TGF)-β inhibitor, or a tyrosine kinase inhibitor.

14. The method of claim 1, wherein the subject has cancer, and wherein the cancer is a chemotherapy resistant cancer or a radiation resistant cancer.

15. The method of claim 1, wherein the adenoviral vector encodes the polypeptide comprising SEQ ID NO: 5.

16. The method of claim 1, wherein the adenoviral vector encodes the polypeptide consisting of SEQ ID NO: 6.

* * * * *

SEQUENCE LISTING

```
<160> NUMBER OF SEQ ID NOS: 6

<210> SEQ ID NO 1
<211> LENGTH: 435
<212> TYPE: PRT
<213> ORGANISM: Homo sampiens

<400> SEQUENCE: 1

Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
            20                  25                  30

Glu Lys Gly Asp Pro Thr Glu Arg Glu Leu Arg Val Gly Leu Glu Glu
        35                  40                  45

Ser Glu Leu Trp Leu Arg Phe Lys Glu Leu Thr Asn Glu Met Ile Val
    50                  55                  60

Thr Lys Asn Gly Arg Arg Met Phe Pro Val Leu Lys Val Asn Val Ser
65                  70                  75                  80

Gly Leu Asp Pro Asn Ala Met Tyr Ser Phe Leu Leu Asp Phe Val Ala
                85                  90                  95

Ala Asp Asn His Arg Trp Lys Tyr Val Asn Gly Glu Trp Val Pro Gly
            100                 105                 110

Gly Lys Pro Glu Pro Gln Ala Pro Ser Cys Val Tyr Ile His Pro Asp
        115                 120                 125

Ser Pro Asn Phe Gly Ala His Trp Met Lys Ala Pro Val Ser Phe Ser
    130                 135                 140

Lys Val Lys Leu Thr Asn Lys Leu Asn Gly Gly Gly Gln Ile Met Leu
145                 150                 155                 160

Asn Ser Leu His Lys Tyr Glu Pro Arg Ile His Ile Val Arg Val Gly
                165                 170                 175

Gly Pro Gln Arg Met Ile Thr Ser His Cys Phe Pro Glu Thr Gln Phe
            180                 185                 190

Ile Ala Val Thr Ala Tyr Gln Asn Glu Glu Ile Thr Ala Leu Lys Ile
        195                 200                 205

Lys Tyr Asn Pro Phe Ala Lys Ala Phe Leu Asp Ala Lys Glu Arg Ser
    210                 215                 220

Asp His Lys Glu Met Met Glu Glu Pro Gly Asp Ser Gln Gln Pro Gly
225                 230                 235                 240

Tyr Ser Gln Trp Gly Trp Leu Leu Pro Gly Thr Ser Thr Leu Cys Pro
                245                 250                 255

Pro Ala Asn Pro His Pro Gln Phe Gly Gly Ala Leu Ser Leu Pro Ser
            260                 265                 270

Thr His Ser Cys Asp Arg Tyr Pro Thr Leu Arg Ser His Arg Ser Ser
```

```
                275                 280                 285
    Pro Tyr Pro Ser Pro Tyr Ala His Arg Asn Asn Ser Pro Thr Tyr Ser
        290                 295                 300
    Asp Asn Ser Pro Ala Cys Leu Ser Met Leu Gln Ser His Asp Asn Trp
    305                 310                 315                 320
    Ser Ser Leu Gly Met Pro Ala His Pro Ser Met Leu Pro Val Ser His
                    325                 330                 335
    Asn Ala Ser Pro Pro Thr Ser Ser Ser Gln Tyr Pro Ser Leu Trp Ser
                340                 345                 350
    Val Ser Asn Gly Ala Val Thr Pro Gly Ser Gln Ala Ala Val Ser
                355                 360                 365
    Asn Gly Leu Gly Ala Gln Phe Phe Arg Gly Ser Pro Ala His Tyr Thr
        370                 375                 380
    Pro Leu Thr His Pro Val Ser Ala Pro Ser Ser Gly Ser Pro Leu
    385                 390                 395                 400
    Tyr Glu Gly Ala Ala Ala Thr Asp Ile Val Asp Ser Gln Tyr Asp
                    405                 410                 415
    Ala Ala Ala Gln Gly Arg Leu Ile Ala Ser Trp Thr Pro Val Ser Pro
                420                 425                 430
    Pro Ser Met
            435

<210> SEQ ID NO 2
<211> LENGTH: 2518
<212> TYPE: DNA
<213> ORGANISM: Homo sapiens

<400> SEQUENCE: 2
tttgcttttg cttatttccg tccatttccc tctctgcgcg cggaccttcc ttttccagat     60
ggtgagagcc gcgggacac  ccgacgccgg ggcaggctga tccacgatcc tgggtgtgcg    120
taacgccgcc tggggctccg tgggcgaggg acgtgtgggg acaggtgcac cggaaactgc    180
cagactggag agttgaggca tcggaggcgc gagaacagca ctactactgc ggcgagacga    240
gcgcggcgca tcccaaagcc cggccaaatg cgctcgtccc tgggagggga gggaggcgcg    300
cctggagcgg ggacagtctt ggtccgcgcc ctcctcccgg gtctgtgccg ggacccggga    360
cccgggagcc gtcgcaggtc tcggtccaag gggccccttt tctcggaagg gcggcggcca    420
agagcaggga aggtggatct caggtagcga gtctgggctt cggggacggc ggggagggga    480
gccggacggg aggatgagct cccctggcac cgagagcgcg ggaaagagcc tgcagtaccg    540
agtggaccac ctgctgagcg ccgtggagaa tgagctgcag gcgggcagcg agaagggcga    600
ccccacagag cgcgaactgc gcgtgggcct ggaggagagc gagctgtggc tgcgcttcaa    660
ggagctcacc aatgagatga tcgtgaccaa gaacggcagg aggatgtttc cggtgctgaa    720
ggtgaacgtg tctggcctgg accccaacgc catgtactcc ttcctgctgg acttcgtggc    780
ggcggacaac caccgctgga agtacgtgaa cggggaatgg gtgccggggg gcaagccgga    840
gccgcaggcg cccagctgcg tctacatcca ccccgactcg cccaacttcg ggcccactg     900 gatgaaggct cccgtctcct tcagcaaagt caagctcacc aacaagctca cggaggggg     960 ccagatcatg ctgaactcct tgcataagta tgagcctcga atccacatag tgagagttgg   1020
gggtccacag cgcatgatca ccagccactg cttccctgag acccagttca tagcggtgac   1080
tgcttatcag aacgaggaga tcacagctct taaaattaag tacaatccat ttgcaaaagc   1140
tttccttgat gcaaaggaaa gaagtgatca caaagagatg atggaggaac ccggagacag   1200
```

```
ccagcaacct gggtactccc aatgggggtg gcttcttcct ggaaccagca ccctgtgtcc   1260
acctgcaaat cctcatcctc agtttggagg tgccctctcc ctcccctcca cgcacagctg   1320
tgacaggtac ccaaccctga ggagccaccg gtcctcaccc taccccagcc ctatgctca    1380 tcggaacaat tctccaacct attctgacaa ctcacctgca tgtttatcca tgctgcaatc   1440
ccatgacaat tggtccagcc ttggaatgcc tgcccatccc agcatgctcc ccgtgagcca   1500
caatgccagc ccacctacca gctccagtca gtaccccagc ctgtggtctg tgagcaacgg   1560
cgccgtcacc ccgggctccc aggcagcagc cgtgtccaac gggctggggg cccagttctt   1620
ccggggctcc cccgcgcact acacacccct cacccatccg gtctcggcgc cctcttcctc   1680
gggatcccca ctgtacgaag gggcggccgc ggccacagac atcgtggaca gccagtacga   1740
cgccgcagcc caaggccgcc tcatagcctc atggacacct gtgtcgccac cttccatgtg   1800
aagcagcaag gcccaggtcc cgaaagatgc agtgactttt tgtcgtggca gccagtggtg   1860
actggattga cctactaggt acccagtggc agtctcaggt taagaaggaa atgcagcctc   1920
agtaacttcc ttttcaaagc agtggaggag cacacggcac ctttccccag agccccagca   1980
tcccttgctc acacctgcag tagcggtgct gtcccaggtg gcttacagat gaacccaact   2040
gtggagatga tgcagttggc ccaacctcac tgacggtgaa aaaatgtttg ccagggtcca   2100 gaaactttt ttggtttatt tctcatacag tgtattggca actttggcac accagaattt    2160
gtaaactcca ccagtcctac tttagtgaga taaaaagcac actcttaatc ttcttccttg   2220
ttgctttcaa gtagttagag ttgagctgtt aaggacagaa taaaatcata gttgaggaca   2280
gcaggtttta gttgaattga aaatttgact gctctgcccc ctagaatgtg tgtattttaa   2340
gcatatgtag ctaatctctt gtgttgttaa actataactg tttcatattt ttctttttgac  2400 aaagtagcca aagacaatca gcagaaagca ttttctgcaa aataaacgca atatgcaaaa   2460
tgtgattcgt ccagttatta gtgaagcccc tccttttgtg agtatttact gtttattg     2518
```

<210> SEQ ID NO 3
<211> LENGTH: 436
<212> TYPE: PRT
<213> ORGANISM: Mus musculus

<400> SEQUENCE: 3

```
Met Ser Ser Pro Gly Thr Glu Ser Ala Gly Lys Ser Leu Gln Tyr Arg
1               5                   10                  15

Val Asp His Leu Leu Ser Ala Val Glu Ser Glu Leu Gln Ala Gly Ser
            20                  25                  30

Glu Lys Gly Asp Pro Thr Glu Arg Glu Leu Arg Val Gly Leu Glu Glu
        35                  40                  45

Ser Glu Leu Trp Leu Arg Phe Lys Glu Leu Thr Asn Glu Met Ile Val
    50                  55                  60

Thr Lys Asn Gly Arg Arg Met Phe Pro Val Leu Lys Val Asn Val Ser
65                  70                  75                  80

Gly Leu Asp Pro Asn Ala Met Tyr Ser Phe Leu Leu Asp Phe Val Thr
                85                  90                  95

Ala Asp Asn His Arg Trp Lys Tyr Val Asn Gly Glu Trp Val Pro Gly
            100                 105                 110

Gly Lys Pro Glu Pro Gln Ala Pro Ser Cys Val Tyr Ile His Pro Asp
        115                 120                 125

Ser Pro Asn Phe Gly Ala His Trp Met Lys Ala Pro Val Ser Phe Ser
    130                 135                 140
```

Lys Val Lys Leu Thr Asn Lys Leu Asn Gly Gly Gln Ile Met Leu
145                 150                 155                 160

Asn Ser Leu His Lys Tyr Glu Pro Arg Ile His Ile Val Arg Val Gly
                165                 170                 175

Gly Pro Gln Arg Met Ile Thr Ser His Cys Phe Pro Gly Thr Gln Phe
            180                 185                 190

Ile Ala Val Thr Ala Tyr Gln Asn Glu Glu Ile Thr Ala Leu Lys Ile
            195                 200                 205

Lys Tyr Asn Pro Phe Ala Lys Ala Phe Leu Asp Ala Lys Glu Arg Asn
        210                 215                 220

Asp His Lys Asp Val Met Glu Glu Pro Gly Asp Cys Gln Gln Pro Gly
225                 230                 235                 240

Tyr Ser Gln Trp Gly Trp Leu Val Pro Gly Ala Gly Thr Leu Cys Pro
                245                 250                 255

Pro Ala Ser Ser His Pro Gln Phe Gly Gly Ser Leu Ser Leu Pro Ser
                260                 265                 270

Thr His Gly Cys Glu Arg Tyr Pro Ala Leu Arg Asn His Arg Ser Ser
            275                 280                 285

Pro Tyr Pro Ser Pro Tyr Ala His Arg Asn Ser Ser Pro Thr Tyr Ala
        290                 295                 300

Asp Asn Ser Ser Ala Cys Leu Ser Met Leu Gln Ser His Asp Asn Trp
305                 310                 315                 320

Ser Ser Leu Gly Val Pro Gly His Thr Ser Met Leu Pro Val Ser His
                325                 330                 335

Asn Ala Ser Pro Pro Thr Gly Ser Ser Gln Tyr Pro Ser Leu Trp Ser
                340                 345                 350

Val Ser Asn Gly Thr Ile Thr Pro Gly Ser Gln Thr Ala Gly Val Ser
            355                 360                 365

Asn Gly Leu Gly Ala Gln Phe Phe Arg Gly Ser Pro Ala His Tyr Thr
        370                 375                 380

Pro Leu Thr His Thr Val Ser Ala Ala Thr Ser Ser Ser Ser Gly Ser
385                 390                 395                 400

Pro Met Tyr Glu Gly Ala Ala Thr Val Thr Asp Ile Ser Asp Ser Gln
                405                 410                 415

Tyr Asp Thr Ala Gln Ser Leu Leu Ile Ala Ser Trp Thr Pro Val Ser
            420                 425                 430

Pro Pro Ser Met
        435

<210> SEQ ID NO 4
<211> LENGTH: 2046
<212> TYPE: DNA
<213> ORGANISM: Mus musculus

<400> SEQUENCE: 4
ggctccgcag agtgacccett tttcttggaa aagcggtggc gagagaagtg aaggtggctg      60
ttgggtaggg agtcaagact cctggaaggt ggagagggtg gcgggaggat gagctcgccg     120
ggcacagaga gcgcagggaa gagcctgcag taccgagtgg accacctgct cagcgccgtg     180
gagagcgagc tgcaggcggg cagcgagaag ggagaccccca ccgaacgcga actgcgagtg     240
ggcctggagg agagcgagct gtggctgcgc ttcaaggagc taactaacga gatgattgtg     300
accaagaacg gcaggaggat gttcccggtg ctgaaggtaa atgtgtcagg cctgaccccc     360
aatgccatgt actctttctt gctggacttc gtgacggctg acaaccaccg ctggaaatat     420

-continued

```
gtgaacgggg agtgggtacc tgggggcaaa ccagagcctc aggcgcccag ctgcgtctac    480
atccacccag actcgcccaa ttttggggcc cactggatga aggcgcctgt gtctttcagc    540
aaagtcaaac tcaccaacaa gctcaatgga gggggacaga tcatgttaaa ctccttgcat    600
aagtatgaac tcggattca catcgtgaga gttgggggcc cgcaacgcat gatcaccagc    660
cactgctttc ccgagaccca gttcatagct gtgactgcct accagaatga ggagattaca    720
gcccttaaaa ttaaatacaa cccatttgct aaagccttcc ttgatgccaa agaaagaaac    780
gaccacaaag atgtaatgga ggaaccgggg gactgccagc agccggggta ttcccaatgg    840
gggtggcttg ttcctggtgc tggcaccctc tgcccgcctg ccagctccca ccctcagttt    900
ggaggctcgc tctctctccc ctccacacac ggctgtgaga ggtacccagc tctaaggaac    960
caccggtcat cgccctaccc cagccccta tgctcatcgga acagctctcc aacctatgcg   1020
gacaattcat ctgcttgtct gtccatgctg cagtcccatg ataactggtc tagcctcgga   1080
gtgcctggcc acaccagcat gctgcctgtg agtcataacg ccagcccacc tactggctct   1140
agccagtatc ccagtctctg gtctgtgagc aatggtacca tcaccccagg ctcccagaca   1200
gctggggtgt ccaacgggct gggagctcag ttctttcgag gctcccctgc acattacaca   1260
ccactgacgc acacggtctc agctgccacg tcctcgtctt ctggttctcc gatgtatgaa   1320
ggggctgcta cagtcacaga catttctgac agccagtatg acacggccca agcctcctc   1380 atagcctcgt ggacacctgt gtcaccccca tctatgtgaa ttgaactttc ctccatgtgc   1440
tgagacttgt aacaaccggt gtcaactgga tcttctaggc tcaaagtggc aggctcttgg   1500
gacaagggaa aaataaataa ataaaagcta gatactaaca actccattt caaataagag   1560 caataataca tgtcctataa tcatgttcta cagcctcttg tttgatacct acagtagtga   1620
tatgtgtcct acattatgaa gccaaggaca gagagacggc tgtggtccag tttttttgtga  1680 ctggcagtta atcagagtcc tttgctaggt agggtcctat atcttgtgtt tctctacaac   1740
atatatgtga ctttgaaatc ctggaattcg tccacccct gtcctacttt agtgagacac    1800
aaggtacacc tctaatgtcc tcccttgttg ccttagagta gttaactttg aggacagaaa   1860
aaagcatagc cagaagattg taactgaacc gtcaactgtt ctgcccttgg aacatgccta   1920
ctttaagcac acgtagcttt ttgtgttggg aagtcaactg tatggatact tttctgttga   1980
caaagtagcc aaagacaatc tgcagaaagt gttttctgca caataaaggc aatatatagc   2040
acctgg                                                              2046
```

<210> SEQ ID NO 5
<211> LENGTH: 15
<212> TYPE: PRT
<213> ORGANISM: Artificial Sequence
<220> FEATURE:
<223> OTHER INFORMATION: Synthetic

<400> SEQUENCE: 5

Arg Pro Met Phe Pro Val Leu Lys Val Asn Val Ser Gly Leu Asp
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic

<400> SEQUENCE: 6

-continued

```
Gln Trp Gly Trp Leu Leu Pro Gly Thr Ser Thr Leu Cys Pro Pro
1               5                   10                  15
```